United States Patent
Gao et al.

(10) Patent No.: US 12,004,876 B2
(45) Date of Patent: Jun. 11, 2024

(54) AUTO-POWERED SYNTHETIC SKIN

(71) Applicant: California Institute of Technology, Pasadena, CA (US)

(72) Inventors: Wei Gao, Pasadena, CA (US); You Yu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 545 days.

(21) Appl. No.: 17/237,925

(22) Filed: Apr. 22, 2021

(65) Prior Publication Data
US 2022/0110588 A1   Apr. 14, 2022

Related U.S. Application Data

(60) Provisional application No. 63/091,385, filed on Oct. 14, 2020.

(51) Int. Cl.
| | |
|---|---|
| *A61B 5/145* | (2006.01) |
| *A61B 5/00* | (2006.01) |
| *A61B 5/1486* | (2006.01) |
| *H01M 8/16* | (2006.01) |
| *A61B 10/00* | (2006.01) |

(52) U.S. Cl.
CPC .......... *A61B 5/6832* (2013.01); *A61B 5/0004* (2013.01); *A61B 5/002* (2013.01); *A61B 5/14517* (2013.01); *A61B 5/1486* (2013.01); *H01M 8/16* (2013.01); *A61B 10/0051* (2013.01); *A61B 10/0064* (2013.01); *A61B 2010/0067* (2013.01); *A61B 10/007* (2013.01); *A61B 2560/0214* (2013.01)

(58) Field of Classification Search
CPC ............ A61B 10/0051; A61B 10/0064; A61B 10/007; A61B 2010/0067; A61B 2560/0214; A61B 5/0004; A61B 5/002; A61B 5/0053; A61B 5/14517; A61B 5/14546; A61B 5/1477; A61B 5/1486; A61B 5/6832; A61B 5/6833; Y02E 60/50; H01M 8/16
See application file for complete search history.

(56) References Cited

U.S. PATENT DOCUMENTS

| | | | | |
|---|---|---|---|---|
| 2009/0171413 | A1* | 7/2009 | Zenati ................ | A61N 1/36585 607/35 |
| 2009/0305089 | A1* | 12/2009 | Minteer ................ | C12N 11/00 435/317.1 |
| 2010/0178572 | A1* | 7/2010 | Kato ...................... | C12Q 1/006 429/401 |
| 2016/0178567 | A1* | 6/2016 | Lee ........................ | C12Q 1/005 435/14 |
| 2017/0325724 | A1* | 11/2017 | Wang .................. | A61B 5/14532 |
| 2018/0233761 | A1* | 8/2018 | Slaughter ............. | A61B 5/0031 |
| 2019/0117083 | A1* | 4/2019 | Wang .................... | A61B 5/6833 |
| 2019/0307372 | A1* | 10/2019 | Ocampo .............. | A61B 5/0002 |

(Continued)

*Primary Examiner* — Eric J Messersmith
(74) *Attorney, Agent, or Firm* — Sheppard Mullin Richter & Hampton LLP

(57) ABSTRACT

An auto-powered biosensor capable detecting a target molecule, and a method of powering the same, wherein the biosensor is fabricated with a microfluidics layer, a multimodal sensing layer comprising a biofuel cell and an electrode, and a logic circuit that may include a processor and non-transitory memory with computer executable instructions embedded thereon.

19 Claims, 76 Drawing Sheets

(56) References Cited

U.S. PATENT DOCUMENTS

2020/0253520 A1\* 8/2020 Wang .................... A61B 5/002
2020/0337641 A1\* 10/2020 Wang ................... A61B 5/1486
2021/0401346 A1\* 12/2021 Visweswara ....... A61B 5/14507

\* cited by examiner

3001

3002

AUTO-POWERED SYNTHETIC SKIN

CROSS-REFERENCE TO RELATED APPLICATIONS

This application claims priority to U.S. provisional application No. 63/091,385 titled "Biofuel Powered Electronic Skin" and filed Oct. 14, 2020, the contents of which are incorporated herein by reference in its entirety.

GOVERNMENT LICENSE RIGHTS

This invention was made with government support under Grant No. NR018271 awarded by the National Institutes of Health. The government has certain rights in the invention.

BACKGROUND

In addition to mimicking and recreating properties of human skin, synthetic skin provides mechanical durability, elasticity, and enhanced sensory capability beyond that of the human nervous system, including the ability to sense micro-climate and pressure variances. With numerous advanced technologies incorporated into synthetic skin, providing sufficient power in a reasonably small footprint has become a critical challenge. Existing battery technology suffers from inadequate long-term continuous usability, and often breakdown faster due to prolonged exposure to heat and moisture. Further, battery cells are relatively large, cumbersome, and present safety concerns to the wearer.

SUMMARY

Technology disclosed herein provides solutions to power sensors and devices onboard a wearable device using accessible biofuel instead of battery cell technology. For example, the biofuel may include perspiration from the wearer of the device. More specifically, embodiments of the present disclosure are directed to multiplexed vital sign monitoring using an auto-powered biosensor. In some examples, a wearable synthetic skin biosensor and related methods of use enable synchronous and/or asynchronous data collection and monitoring of physiological responses and vital signs of a user. In some examples, the data collection and monitoring may be obtained continuously or semi-continuously and transmitted to a remote device or stored locally.

In an example embodiment, an auto-powered biosensor capable of detecting a target molecule in a biological sample includes a microfluidics layer, a multimodal sensing layer comprising an electrode and a biofuel cell, and a logic circuit with a processor and a non-transitory memory with computer executable instructions embedded thereon. In some embodiments, the biosensor may also include a moisture resistant layer. In some examples, the microfluidics layer may comprise multiple microchannels transversely oriented to obtain a biological sample. The biological sample may include a target molecule and an energy molecule. The multimodal sensing layer may be fluidically coupled to the microfluidics layer to receive the biological sample from the microchannels. The electrode, for example, may be configured to detect a measurement of an electrical property corresponding to a target molecule being present in the biological sample. The biofuel cell, for example, may include a lactate oxidase immobilized anode and a platinum-alloy (Pt-alloy) nanoparticle decorated cathode configured to harvest energy from the energy molecule present in the biological sample to power the biosensor. In embodiments, the logic circuit may be electrically coupled to the electrode, and the computer executable instructions may cause the processor to identify the electrical property detected with the electrode when the target molecule is present in the biological sample. A target molecule, for example, may include a specific protein, peptide, vitamin, amino acid, hormone, antibody, or drug metabolite. An energy molecule, for example, may include lactate or oxygen.

In some embodiments, the biological sample may include sweat, blood, tears, urine, or saliva. In some embodiments, the lactate oxidase immobilized anode may include hierarchical Ni microstructures (h-Ni), reduced graphene oxide (rGO) films, and bimediator modified carbon nanotubes (CNTs). In embodiments, bimediator modified CNTs may include Meldola's Blur-tetrathiafulvalene modified CNTs (MDB-TTF-CNTs). In embodiments, the electrical property may be an electrical current, an electrical voltage, or an electrical impedance.

In some embodiments, the computer executable instructions may include causing the processor to generate an indication identifying the presence of the target molecule based on the electrical property detected with the electrode. In some embodiments, the computer executable instructions may include causing the processor to wirelessly transmit to the user the indication identifying the presence of the target molecule. In some embodiments, wireless transmission of the indication to the user identifying the presence of the target molecule may include Bluetooth® communication. In some embodiments, the auto-powered biosensor may also include a display, wherein the computer executable instructions may cause the processor to output the indication identifying the presence of the target molecule to the display.

In some embodiments, a method for powering an auto-powered biosensor includes receiving a biological sample with the biosensor, and harvesting energy from an energy molecule present in the biological sample. In embodiments, receiving a biological sample may include channeling the biological sample through the microfluidics layer to the multimodal sensing layer. In embodiments, harvesting energy from an energy molecule present in the biological sample may include using a biofuel cell to catalyze lactate to pyruvate. In some embodiments, harvesting energy with the biofuel cell may include reducing oxygen to water. The auto-powered biosensor, for example, may include a microfluidics layer, a multimodal sensing layer which includes a biofuel cell and an electrode configured to detect a measurement of an electrical property corresponding to a target molecule being present in a biological sample, and a logic circuit.

Other features and aspects of the disclosure will become apparent from the following detailed description, taken in conjunction with the accompanying drawings, which illustrate, by way of example, the features in accordance with various embodiments. The summary is not intended to limit the scope of the invention, which is defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION

Wearable biosensors, such as synthetic skin, offer tremendous potential for biomedical applications. Technology disclosed herein is directed to auto-powered biosensors capable of harvesting energy directly from a biological sample (e.g., sweat) and methods of powering the same.

Figure 1:
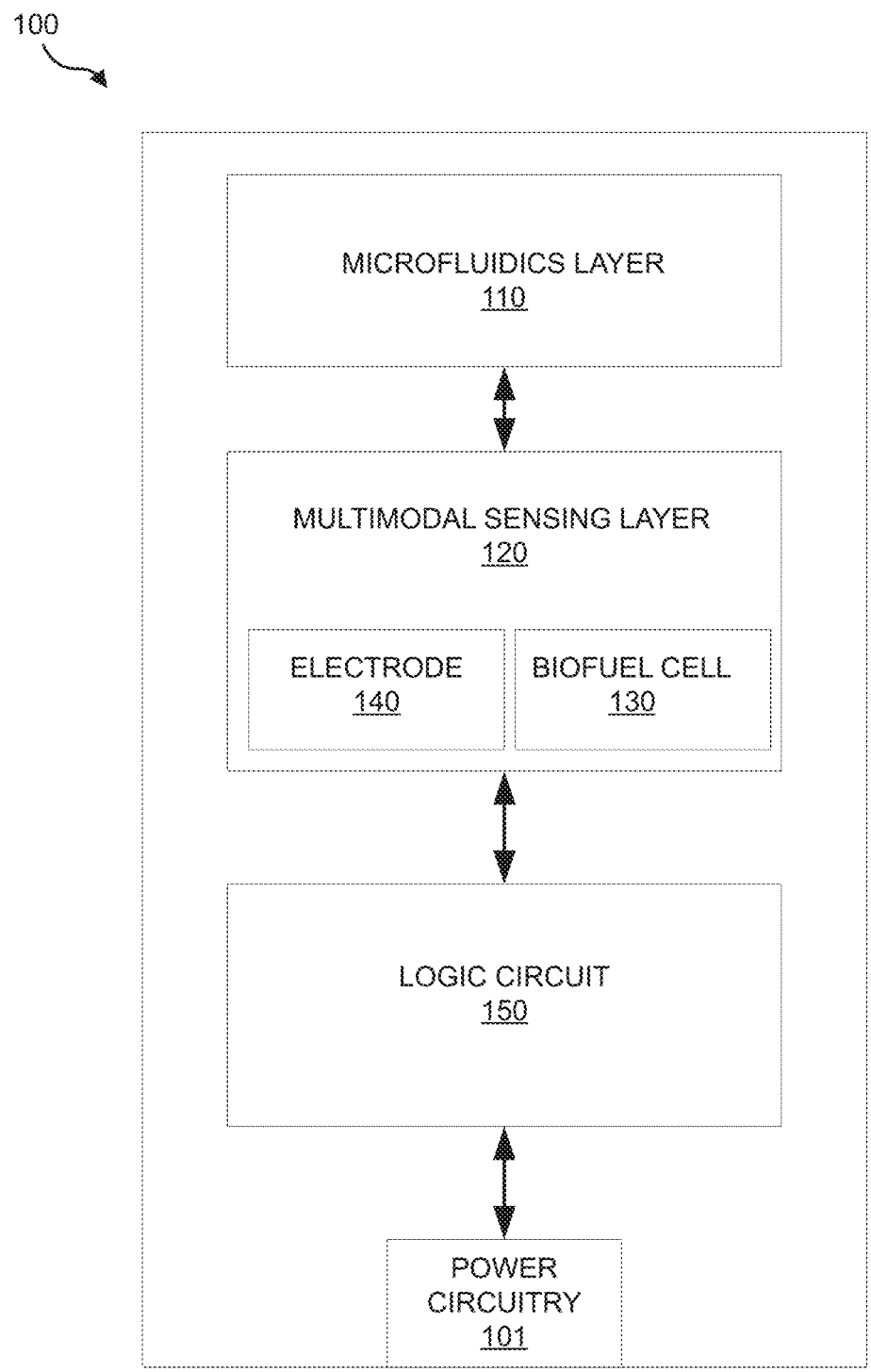
FIG. 1 is a block diagram illustrating some components of an auto-powered biosensor, in accordance with various embodiments of the disclosure.

FIG. 1 is a block diagram illustrating some components of an auto-powered biosensor, in accordance with various embodiments of the disclosure. Biosensor 100 may include, for example, a microfluidics layer 110, a multimodal sensing layer 120 comprising a biofuel cell 130 and an electrode 140, and a logic circuit 150. The electrical components of biosensor 100 may include power circuitry 101 for distributing power.

During operation, biosensor 100 may be introduced to a biological sample containing a target molecule and an energy molecule. Microfluidics layer 110 is shaped to receive a biological sample and channel it to the multimodal sensing layer 120. Multimodal sensing layer 120 may include an electrode 140 that detects the presence of a target molecule in the biological sample and a biofuel cell 130 that harvests energy from various energy molecules in the biological sample. Energy harvested by biofuel cell 130 may be used to power biosensor 100. If the target molecule is present in the biological sample, logic circuit 150, which is electrically coupled to electrode 140, may generate an indication that the target molecule is present in the biological sample. In embodiments, biosensor 100 may also include a moisture resistant layer that is adhesively attached to microfluidics layer 110 and configured to funnel the biological sample through an inlet on its surface. In some embodiments, biosensor 100 may also include a display to display the indication. In some embodiments, biosensor 100 may wirelessly communicate the indication to a mobile device, such as a cellular phone or other handheld computer. In examples, the indication may be communicated by biosensor 100 to the mobile device using Bluetooth® communication or other near-field communication (NFC) technology. As described herein, biosensor 100 allows for a fully-integrated platform with enhanced wearability and sensing accuracy. In embodiments, biosensor 100 may be ultrathin, transparent, and may use minimal power consumption.

In various embodiments, microfluidics layer 110 may be comprised of a material that may be shaped to have at least one microchannel or inlet through which a biological sample may flow. Such materials that may comprise microfluidics layer 110 include, for example, plastics (e.g., polyethylene film), ceramics, glass, metal, polymer, and/or wood (e.g., paper-based materials). In embodiments, microfluidics layer 110 may be adhesive such that it can attach to the user. In some embodiments, microfluidics layer 110 may be adhesive on both sides such that it can attach to the user and to other components of biosensor 100 simultaneously. For example, in some embodiments, microfluidics layer 110 may be double-sided adhesive medical tape. In some embodiments, microfluidics layer 110 may comprise an adhesive elastomer (e.g., PDMS, Ecoflex).

In embodiments, manufacturing microfluidics layer 110 may include laser engraving a microchannel, reservoir, and/or inlet using a laser cutter, for example, a $CO_2$ laser. Laser engraving offers a great alternative for rapid and bulk manufacturing of the microfluidics layer 110. In some embodiments, microfluidics layer 110 may be prepared using vector mode laser cutting. In some embodiments, raster mode laser cutting may be used. In some embodiments, at least one microchannel, reservoir, and/or inlet is laser-engraved into the surface of the microfluidics layer 110. In some embodiments, multiple microchannels, reservoirs, and/or inlets are engraved into the surface of microfluidics layer 110. In some embodiments, multiple microchannels, reservoirs, and/or inlets are laser engraved into and through microfluidics layer 110. In embodiments, laser engraving parameters for forming the microfluidics layer 110 may include: Power 1%, Speed 1.5%, PPI 1000 for reservoir outline and channels; and Power 2%, Speed 1%, PPI 1000 for inlet outlines, both in vector mode at focused height. It is to be understood that other laser engraving parameters may be used (e.g., power, speed, and/or PPI) depending on the application and material to be engraved.

The number of microchannels, reservoirs, and/or inlets of microfluidics layer 110 may vary in accordance with the use of the auto-powered biosensor. A person of ordinary skill in the art would appreciate that the flow rate of the biological sample may be impacted by the number of microchannels and/or inlets of microfluidics layer 110. Moreover, a person of ordinary skill would appreciate that the flow rate may also be impacted by the biological sample itself. In embodiments, between 1 to 10 microchannels and/or inlets may be engraved. In other embodiments, between 1-20 microchannels and/or inlets may be engraved. In still more embodiments, 1-100 microchannels and/or inlets may be engraved. The microchannels and/or inlets of microfluidics layer 110 may be transversely oriented to channel a biological sample to the microfluidics layer 110. In embodiments, microfluidics layer 110 significantly improves sweat refreshing and reduces interference between the biofuel cells and electrodes/sensors of the multimodal sensing layer.

For wearable on-body use, the integration of a microfluidics layer may greatly enhance biological sample sampling (e.g., sweat sampling) and lead to a higher temporal resolution for wearable sensing and more stable output from the biofuel cells. In embodiments, the laser-patterned microfluidics layer may be assembled in a sandwich structure (M-tape/PDMS/M-tape) ("PDMS" or polydimethylsiloxane) and may contain two reservoirs to minimize the influence of the biofuel cell byproducts on the sensing accuracy.

Biosensor 100 may also include multimodal sensing layer 120. Multimodal sensing layer 120 may be fluidically coupled to microfluidics layer 110 in order to receive a biological sample. In embodiments, multimodal sensing layer 120 is fluidically coupled to a surface of the microfluidics layer 110 to receive a biological sample from the microchannels, inlets, and/or reservoirs of microfluidics layer 110.

In embodiments, multimodal sensing layer 120 may include a biofuel cell 130 that is configured to harvest energy from an energy molecule present in the biological sample to power the biosensor. Biofuel cell 130 may employ use of enzymes, such as biocatalysts, to transform bioenergy into electricity. Among bioenergy resources, lactate, the main metabolic product of both muscle and brain exertion, is found abundantly in biological samples, including for example, sweat. Levels of lactate found in human sweat may vary depending on the individual, their weight, diet, and overall health. On average, the amount of lactate found in sweat is in the millimolar range.

In embodiments, biofuel cell 130 may include one or more anodes and/or cathodes. For example, biofuel cell 130 may include a lactate oxidase (LOx) immobilized anode and/or a platinum-alloy (Pt-alloy) nanoparticle decorated cathode. For example, the lactate immobilized anode may be used to catalyze the lactate found in the biological sample to pyruvate. Additionally, the Pt-alloy nanoparticle (e.g., Pt/Co-alloy nanoparticle) decorated cathode may be used to reduce oxygen to water. Such redox reactions on the biofuel cell 130 yields a stable current to power the electrical loads. In embodiments, monolithic integration of 0 dimensional (OD) to 3 dimensional (3D) nanomaterials may be employed on biofuel cell 130 to obtain optimal energy harvesting performance. For example, the lactate oxidase immobilized anode may include hierarchal Ni microstructures (h-Ni), reduced graphene oxide (rGO) films, and bimediator modified carbon nanotubes (CNTs). In some embodiments, bimediator modified CNTs may include Meldola's Blue-tetrathiafulvalene modified CNTs (MDB-TTF-CNT). Table 1, by way of example, depicts several anode and cathode arrays that may be used in various embodiments.

Figure 2A:
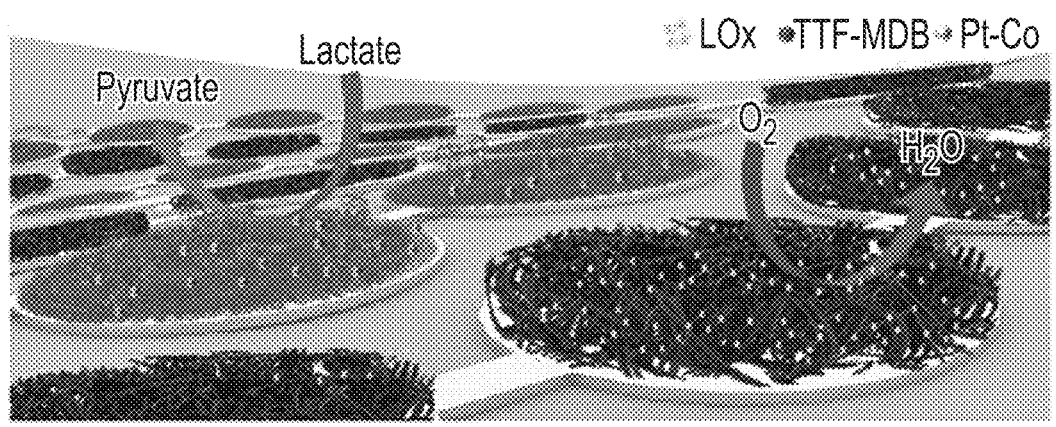
FIG. 2A illustrates by way of example, a biofuel cell array in accordance with various embodiments disclosed herein.
Figure 2B:
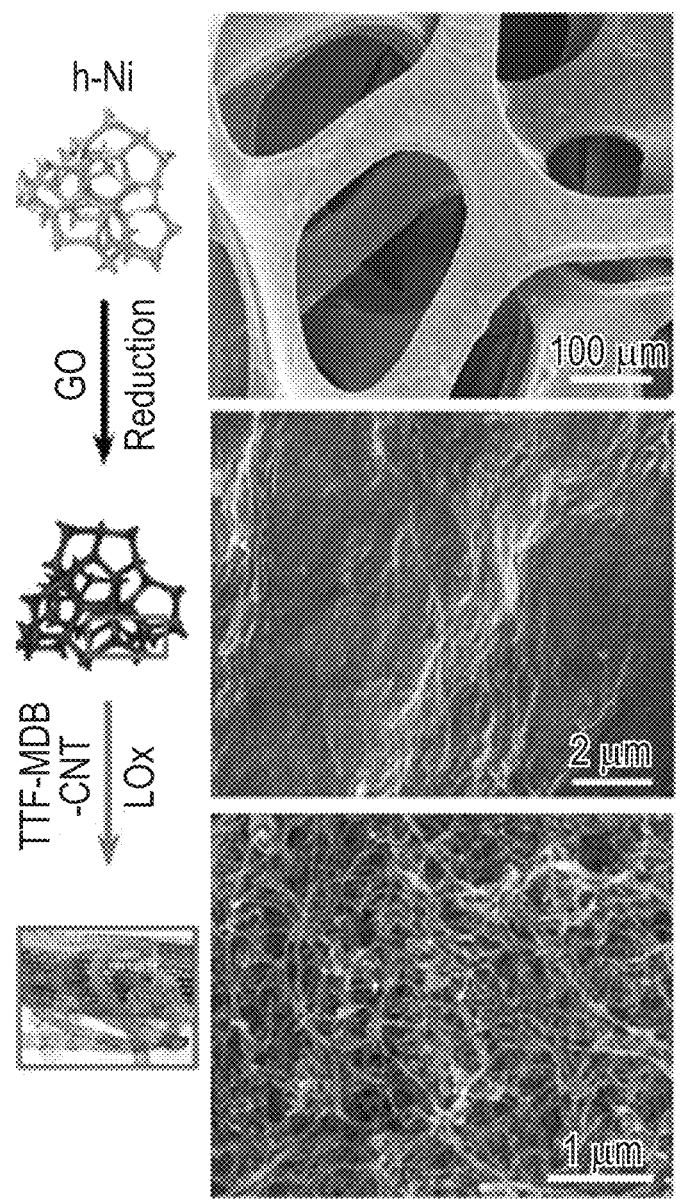
FIG. 2B illustrates by way of example, a biofuel cell array in accordance with various embodiments disclosed herein.
Figure 2C:
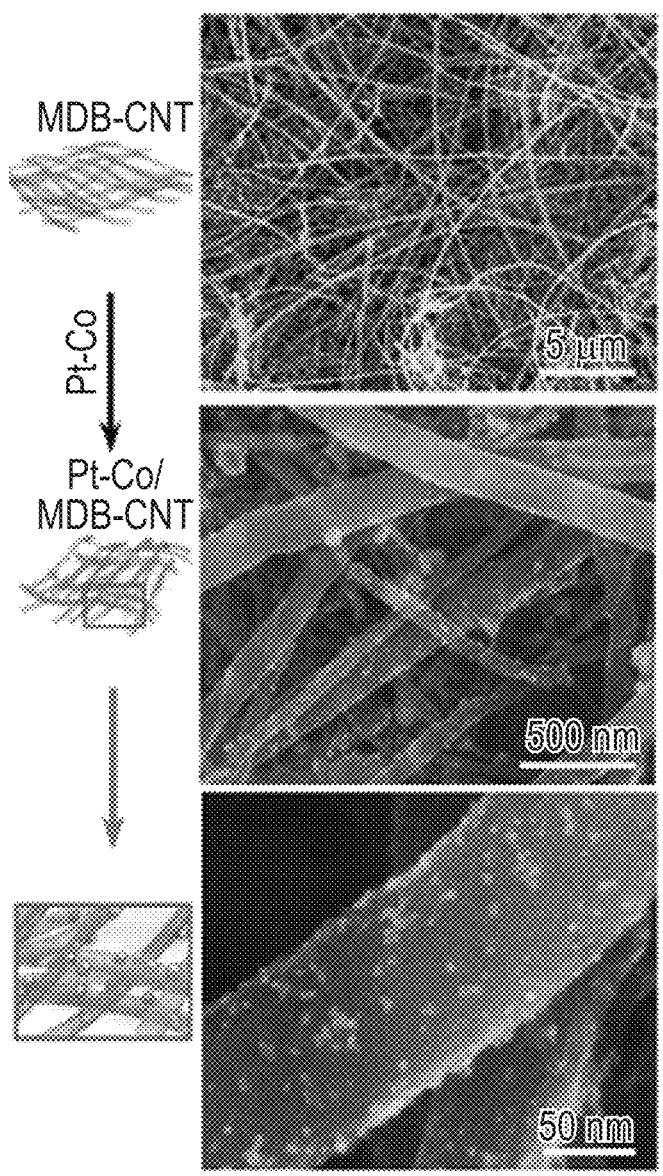
FIG. 2C illustrates by way of example, a biofuel cell array in accordance with various embodiments disclosed herein.

FIGS. 2A-2C illustrate by way of example, biofuel cell configurations in accordance with certain embodiments of the disclosure. For example, biofuel cell configuration of FIG. 2A includes lactate oxidase (LOx) immobilized anodes that may catalyze lactate to pyruvate and Pt-alloy nanoparticle decorated cathodes that may reduce oxygen to water. FIG. 2B illustrates, by way of example, preparation of the anode, wherein hierarchical Ni microstructures, reduced graphene oxide films, and Meldola Blue-tetrathiafulvalene modified carbon nanotubes are sequentially modified on an Au electrode array (MDB-TTF-CNT/rGO/h-Ni anode). FIG. 2C illustrates, preparation of the cathode, wherein Pt-based nanoparticles are decorated on an MDB-modified CNT network (MDB-CNT) through electroless plating.

Figure 3A:
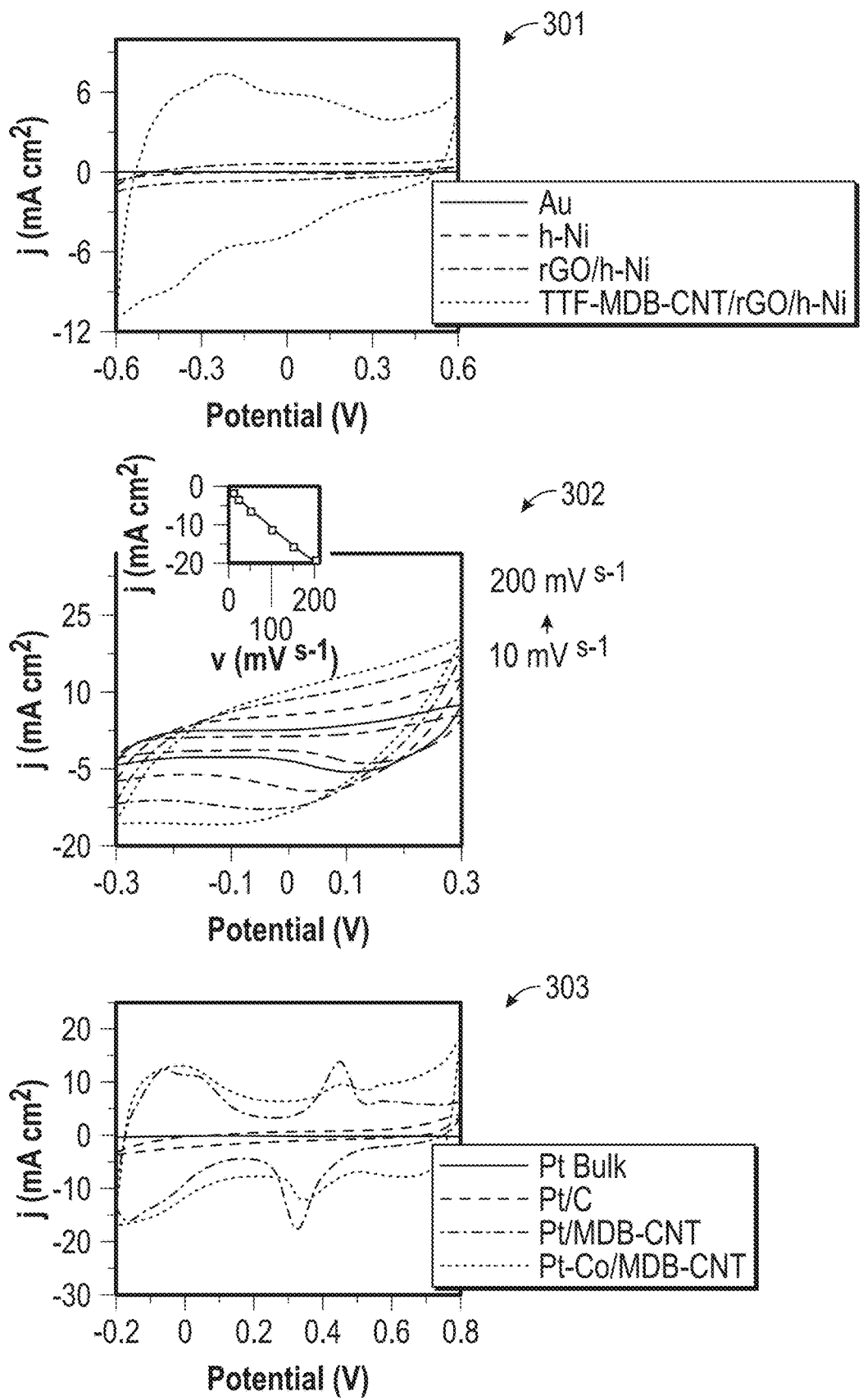
FIG. 3A illustrates by way of example, characterization and optimization of a biofuel cell array in accordance with various embodiments of the disclosure.
Figure 3B:
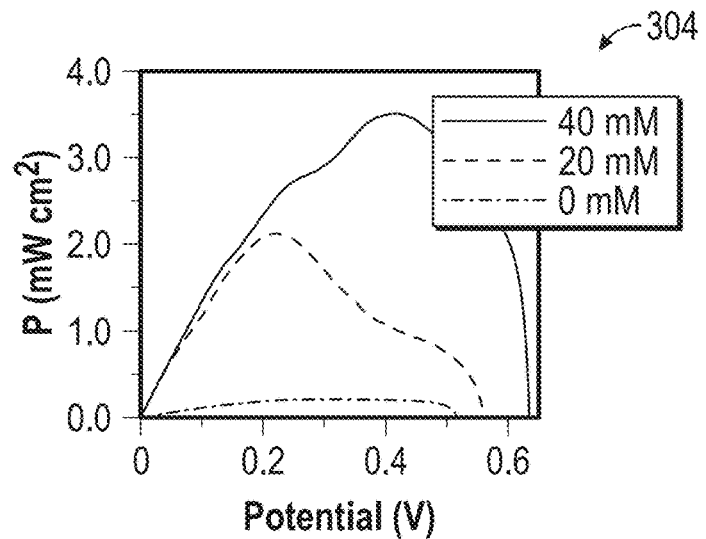
FIG. 3B illustrates by way of example, characterization and optimization of a biofuel cell array in accordance with various embodiments of the disclosure.
Figure 3B:
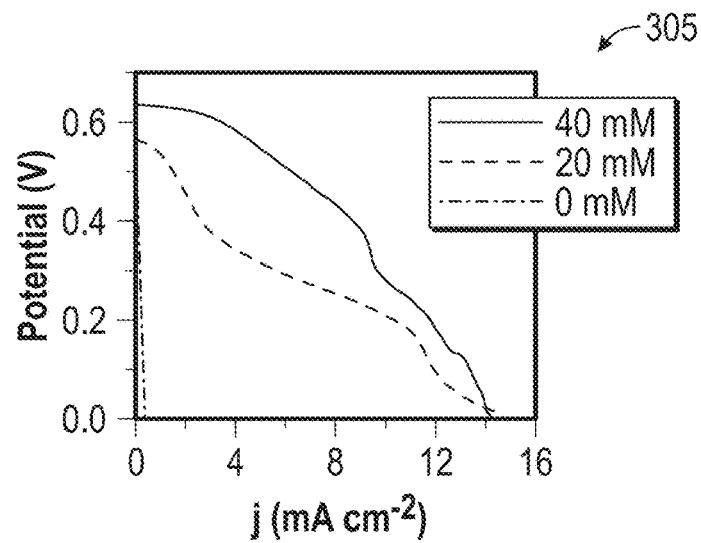
Figure 3B:
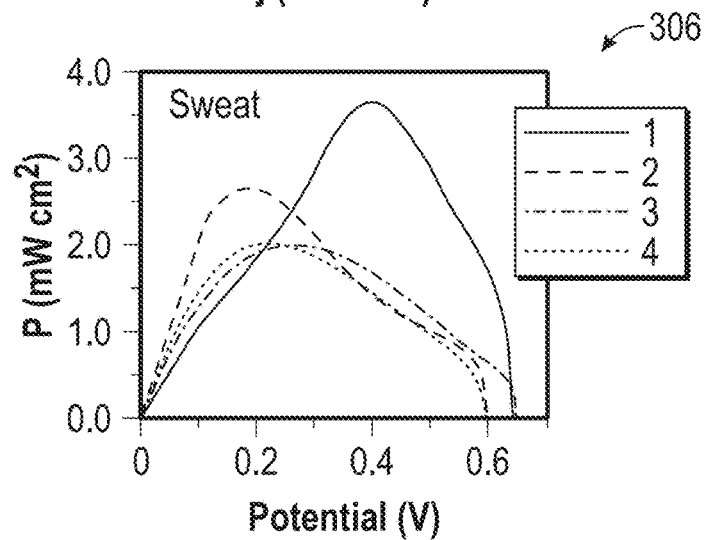

FIGS. 3A and 3B illustrate by way of example, characterization and optimization of a biofuel cell in accordance with certain embodiments of the disclosure. For example, frame 301 illustrates the cyclic voltammograms (CVs) of the Au, h-Ni, rGO/h-Ni, and MDB-CNT/rGO/h-Ni electrodes at 50 mV s$^{-1}$. In embodiments, the high current density and stability of the MDB-TTF-CNT/rGO/h-Ni anode may be attributed to (1) the high electrochemically active surface area that is increased by 3000 times after nanomaterial modification (e.g., frame 302); (2) the pi-pi interaction between the CNT's and rGO that significantly enhance the electron transfer rate between the Lox and electrodes; and (3) the TTF-MDB redox mediator that decreases the overall potential of the lactate oxidation reaction (e.g., Table 2).

Frame 302 illustrates CVs of the MDB-TTF-CNT/rGO/h-Ni with scan rates of 10 mV s$^{-1}$ to 200 mV s$^{-1}$ with inset being calibration curve. Frame 303 illustrates CVs of Pt—Co/MDB-CNT, Pt/MBD-CNT, commercial Pt/C (platinum carbon black), and bulk Pt electrodes recorded in N$_2$-purged 0.1 M H$_2$SO$_4$ solutions at a scan rate of 100 mV s$^{-1}$. In embodiments, the MDB modification allows for uniform nanoparticle distribution with controlled sizes. Compared to that of conventional bulk Pt electrode, Pt and Pt—Co nanoparticles coated MDB-CNT electrodes show significantly higher electrochemically active surface area (e.g., frame 303). Frames 304 and 305 illustrate power density (P) and polar curves of the biofuel cells recorded in 0 to 40 mM lactate, respectively. Indeed, in certain embodiments, an assembled biofuel cell array may achieve an open circuit potential (OCP) at 0.6 V and maximum power outputs of about 2.0 mW cm' and about 3.5 mW cm$^{-2}$ in 20 and 40 mM lactate solutions. Frame 306 illustrates the power density curves of a biofuel cell array in sweat samples from four healthy human subjects, where a power density as high as 3.6 mW cm' may be achieved in certain embodiments.

In embodiments, to enhance the long-term stability of the Pt based biofuel cell cathode, transition metal dopants (e.g., Cobalt, or Co) may be introduced through electroless Co-deposition. The Co dopants may enhance the cohesive energy and thus stabilize the nanoparticles, leading to a higher onset potential for oxygen reduction. Frame 307 illustrates the onset potentials of Pt/MDB-CNT, Pt—Co/IV1DB-CNT, and Nanfion/Pt-Co/MDB-CNT modified cathodes measured in sweat over a one hour period. As illustrated, the Pt—Co/CNT shows a relatively stable onset potential compared to that of the Pt/CNT. In embodiments, a permselective Nafion layer may be modified onto the Pt—Co/CNT. Frame 308 illustrates repetitive linear sweeping voltammograms (LSVs) of the cathodes obtained during 2000 CV cycles between −0.2 and 0.5 V. Frame 309 illustrates long-term stability of the Nafion Pt—Co/CNT cathode over 30 hours.

Returning again to FIG. 1, in embodiments, multimodal sensing layer 120 may include an electrode 140 that is configured to detect a measurement of an electrical property of a target molecule. In some embodiments, multimodal sensing layer 120 may include more than one electrode 140 allowing a user to monitor both chemical and physical properties (e.g., vital signs) of the biological sample and/or the user simultaneously or independently. In embodiments, multimodal sensing layer 120 may comprise a polymer, including, for example, polyimide (PI). Other materials may also be used to construct multimodal sensing layer 120 including metal and/or metal alloy. More than one electrode 140 may share a reference electrode.

In embodiments, electrode 140 may include a chemical sensor configured to detect a measurement of an electrical property of a target molecule. In some embodiments, electrode 140 may be a three-electrode chemical sensor designed to detect and measure various target molecules present in a biological sample, including for example, oxygen, hydrogen, urea, ammonium, glucose, etc. In some embodiments, electrode 140 may detect differences in pH in the biological sample. In some embodiments, detection of these molecules may include detection of ions, either NH$_4^+$ and/or H$^+$. In some embodiments, electrode 140 may be a resistive sensor, or strain senor, designed to detect various vital signs of the user. Vital signs that may be detected using electrode 140 include for example, body temperature, respiration rate, heartrate, etc. In some embodiments, electrode 140 may be a resistive temperature sensor and/or a piezoresistive sensor.

In embodiments, electrode 140 may include a catalytically active substrate. Several types of electrode materials may be used in accordance with the embodiments disclosed herein. Each electrode material has its own advantages and disadvantages. Traditional electrode materials include, for example, graphite, platinum, gold, rhodium, indium, tin, copper, zinc, lead, and/or silver. More contemporary electrode materials include, for example, metallic nanowires, carbon nanotubes (CNTs), conductive polymers, and graphene (including graphene film). Graphene, for example, represents a promising conducting material and may be used as an electrode in a number of different applications including in transistors, light-emitting diodes, liquid crystal displays, molecular junction devices, touch screens, solar cells, and flexible devices. Graphene's advantages include its high charge mobility, transparency, mechanical strength, and flexibility. In embodiments, electrode 140 may include a catalytically active substrate, for example, graphene. In some embodiments, electrode 140 may include platinum, gold, rhodium, indium, tin, copper, zinc, lead, and/or silver electrode. In some embodiments, other conductive materials may be used to form electrode 140, including for example, metallic nanowires, carbon nanotubes (CNTs), and/or conductive polymers. Such nanomaterials may also be used to increase the surface area and/or the signal response of the electrode. In some embodiments, electrode 140 may be gold patterned using photolithography, electron-beam evaporation and lift-off in acetone.

As depicted in FIG. 1, multimodal sensing layer 120 is fluidically coupled to microfluidics layer 110. In embodiments, multimodal sensing layer 120 comprises an electrode 140. Electrode 140 may be configured to detect a measurement of an electrical property of a target molecule in a biological sample that flows from the microfluidics layer 110. In embodiments, a measurement of an electrical property may become detectable by electrode 140 when the target molecule is present in the biological sample. In embodiments, electrode 140 may be configured to detect a measurement of an electrical property of a physical event (e.g., strain, pressure, resistance, and/or temperature).

In embodiments, the electrical property may include an electrical current. In some embodiments, the electrical property may include an electrical voltage. In some embodiments, the electrical property may include an electrical impedance. In embodiments, electrode 140 may be coupled to microfluidics layer 110 and may be configured to detect a measurement of an electrical property. In embodiments, a measurement of an electrical property may include reaching or meeting a threshold of an electrical property. In some embodiments, a measurement of an electrical property may include reaching or meeting a threshold on an electrical property such that when the threshold is reached or met, the measurement may be recorded and sent to the logic circuit for processing. In embodiments, a measurement may include a change in the electrical property. In some embodiments, a measurement may include a change in the electrical property such that when the change in electrical property may be detected, for example, from a baseline, the measurement may be sent to the logic circuit for processing. In some embodiments, a change in electrical property may include an increase or decrease in the electrical property from a certain baseline. In some embodiments, the change in the electrical current, electrical voltage, or electrical impedance, may include a change from a baseline level, or between two or more readings, depending on the assay performed.

In various embodiments disclosed herein, microfluidics layer 110 may be fluidically coupled to multimodal sensing layer 120, wherein multimodal sensing layer 120 comprises at least one electrode 140. In embodiments, multimodal sensing layer 120 comprises more than one electrode 140.

In some embodiments, electrode 140 is a chemical sensor that may detect a target molecule through differential pulse voltammetry (DPV) based on the amplitude of the oxidation current peak of the target molecule. In embodiments, electrode 140 may comprise a resistive sensor. In some embodiments wherein electrode 140 comprises a resistive sensor, the resistive sensor may comprise a resistive temperature sensor or a piezoresistive sensor. In some embodiments, electrode 140 may comprise a piezoresistive sensor that may detect external strain such as, for example, bending. In some embodiments, electrode 140 may comprise a resistive sensor.

In embodiments, multimodal sensing layer 120 allows for multiplexed sensing. Multiplexed sensing is attractive for wearable devices, and in particular for devices monitoring personal health. For example, many crucial biomarkers are present in an individual's sweat, including urea, glucose, pH (e.g., $H^+$ ions), and $NH_4^+$ (i.e., ammonium), all of which contain meaningful information about the individual's physiological status. Multiplexed sensing is crucial to achieve an accurate assessment of these specific analytes. In embodiments, more than one electrode 140 may be used to create sensor arrays that monitor such metabolites. For example, a sensor array may include a urea sensor coupled with a $NH_4^+$ sensor. In other examples, a sensor array may include a glucose sensor and a pH sensor. In embodiments, the $NH_4^+$ sensor may be designed on soft electrochemical patch based on a $NH_4^+$ ion selective electrode. In embodiments, compared to the $NH_4^+$ sensor, the urea sensor may contain an additional enzymatic layer where urease converts urea to carbon dioxide and ammonia ($NH_3$, and then $NH_4^+$); the fluctuation in ammonia may reflect the urea level. The glucose and pH sensor may be prepared using a similar potentiometric sensing approach.

In embodiments, electrode 140 may continuously sense a target molecule in the biological sample. For example, continuous sensing capabilities of electrode 140 may be achieved through continuous injection of a biological sample from the microfluidics layer 110. In embodiments, electrode 140 may continuously detect and measure the concentration of a target molecule through successive DPV scans over multiple cycle periods. In some embodiments, electrode 140 may continuously detect the body temperature of the user. In some embodiments, electrode 140 may continuously detect the heartrate and/or respiration rate of a user.

Figure 4A:
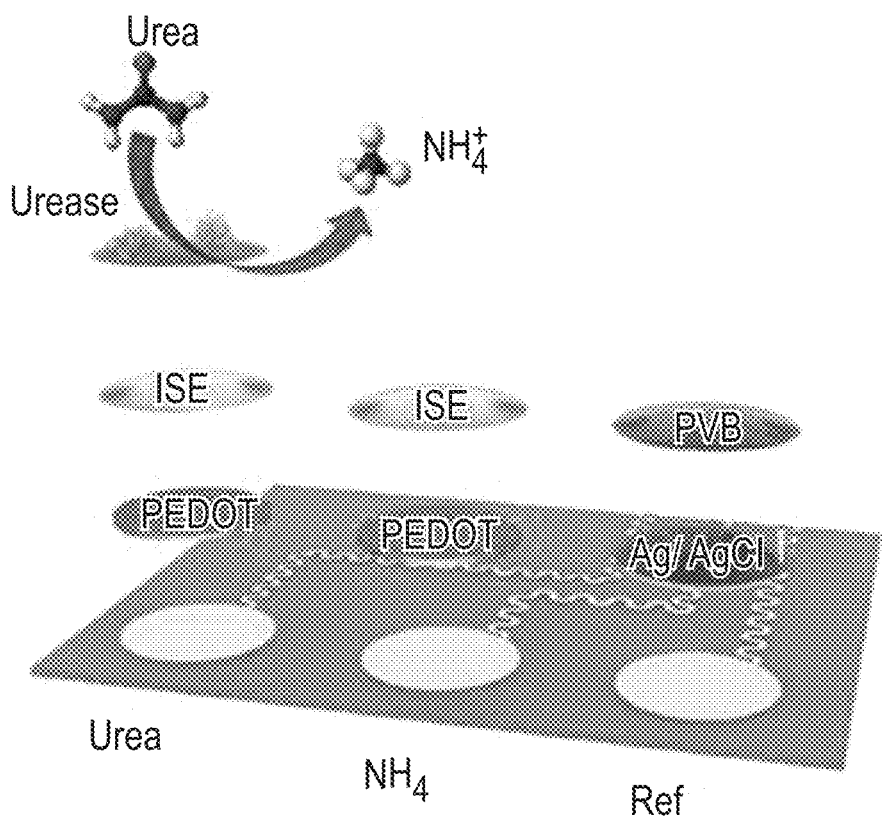
FIG. 4A illustrates, by way of example, characterization of a biofuel cell array accordance with various embodiments of the disclosure.
Figure 4B:
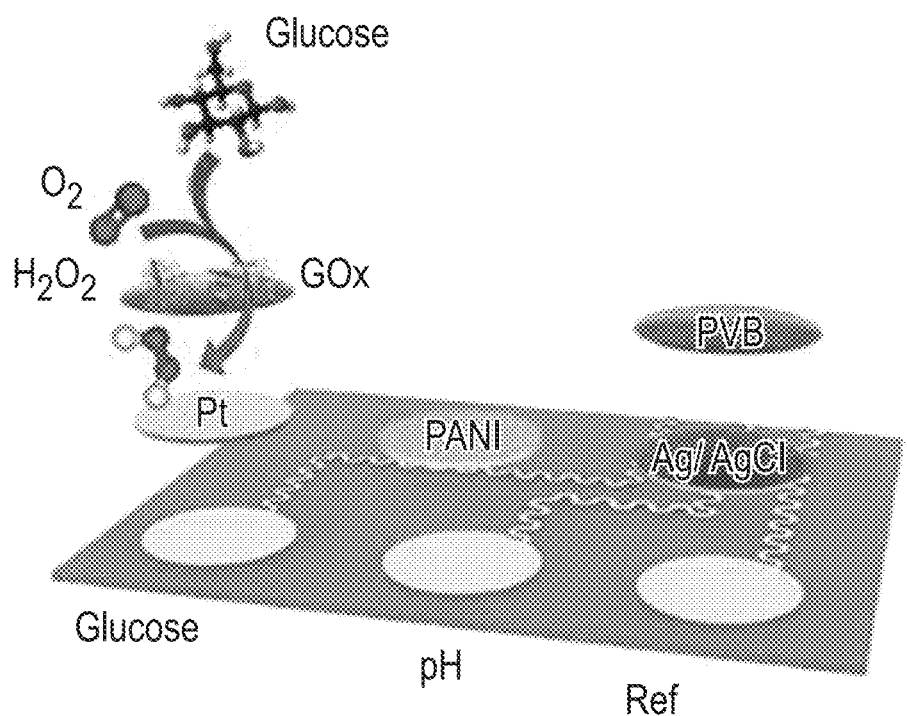
FIG. 4B illustrates, by way of example, characterization of a biofuel cell array accordance with various embodiments of the disclosure.

FIGS. 4A and 4B illustrate, by way of example, various implementations and sensing capabilities of a biosensor that includes at least one electrode 140. Sensors disclosed in various embodiments herein may include more than one electrode 140, which when compiled, create various sensor arrays for multiplexed sensing. For example, FIG. 4A depicts sensors for simultaneous monitoring of urea and $NH_4^+$ in a biological sample. In embodiments, a sensor array may be designed on the soft electrochemical patch based on the $NH_4^+$ ion selective electrodes (ISE). In embodiments, the urea sensor may contain an additional enzymatic layer where urease converts urea to carbon dioxide and ammonia. FIG. 4B depicts sensors for simultaneous monitoring of glucose and pH in a biological sample.

Figure 5A:
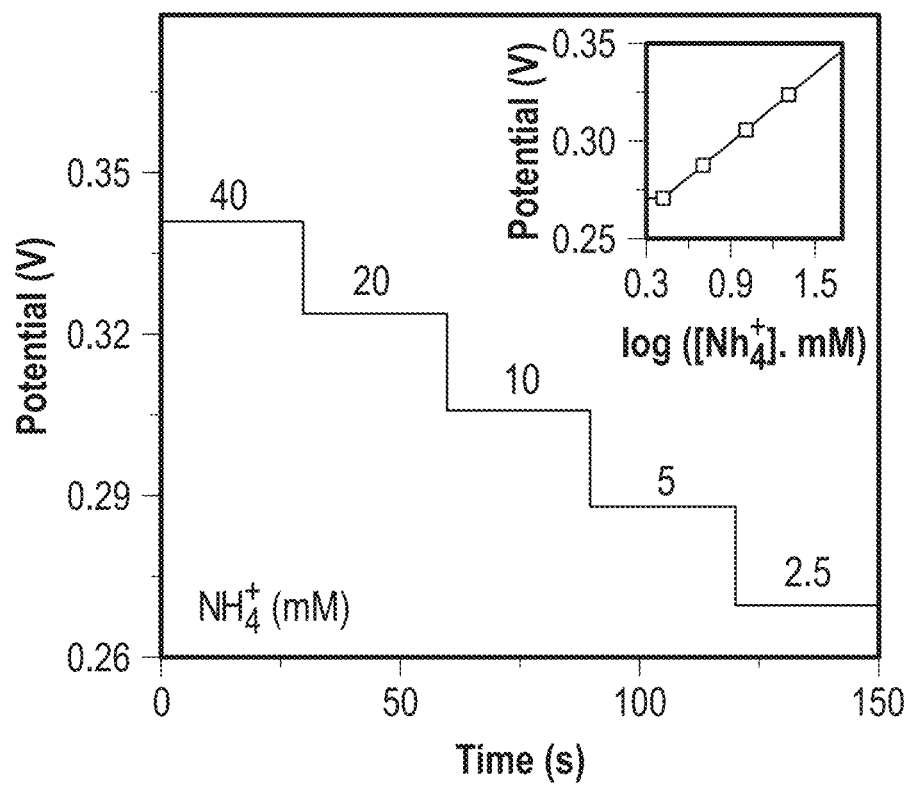
FIG. 5A illustrates, by way of example, target molecule detection and quantification in accordance with various embodiments of the disclosure.
Figure 5B:
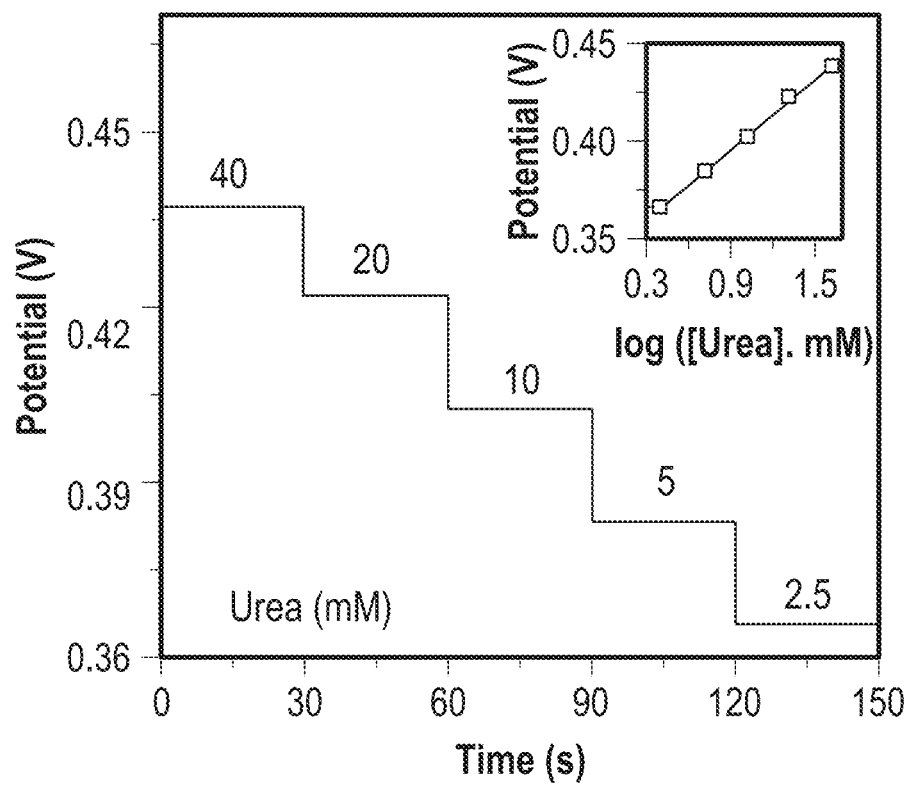
FIG. 5B illustrates, by way of example, target molecule detection and quantification in accordance with various embodiments of the disclosure.
Figure 5C:
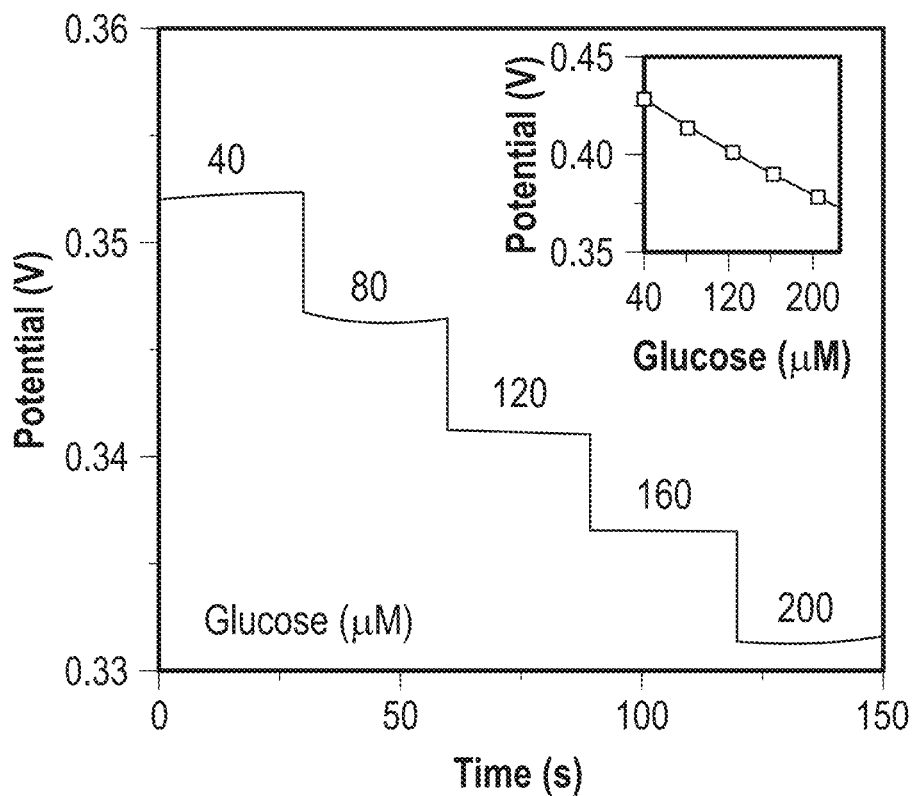
FIG. 5C illustrates, by way of example, target molecule detection and quantification in accordance with various embodiments of the disclosure.
Figure 5D:
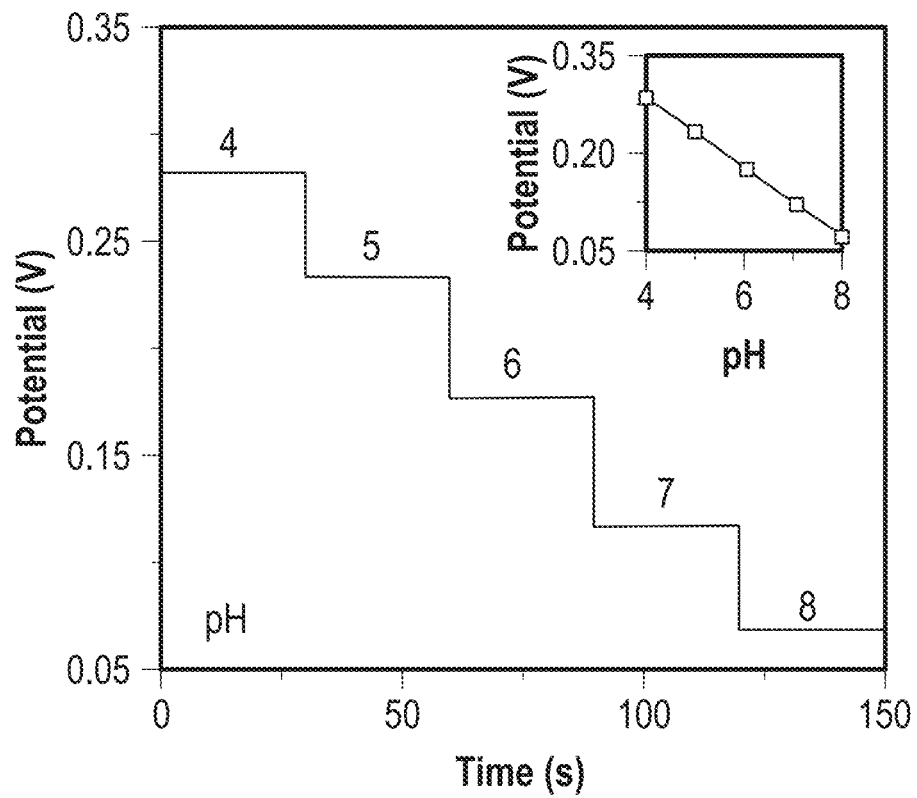
FIG. 5D illustrates, by way of example, target molecule detection and quantification in accordance with various embodiments of the disclosure.

FIGS. 5A-5D illustrate, by way of example, detection of a target molecule using systems and methods in accordance with various embodiments of the disclosure. FIGS. 5A and 5B, for example, depict the potentiometric responses (open circuit potential) of urea and $NH_4^+$ sensors, measured in 40 to 2.5 mM $NH_4^+$ solutions and 40 to 2.5 mM urea solutions, respectively. FIGS. 5C and 5D, for example, depict the potentiometric responses (open circuit potential) of glucose and pH sensors in 40 to 200 µM glucose and pH 4-8 solutions, respectively. In embodiments, a linear relationship between potential output and logarithmic concentrations of the target analytes may be obtained.

Figure 6A:
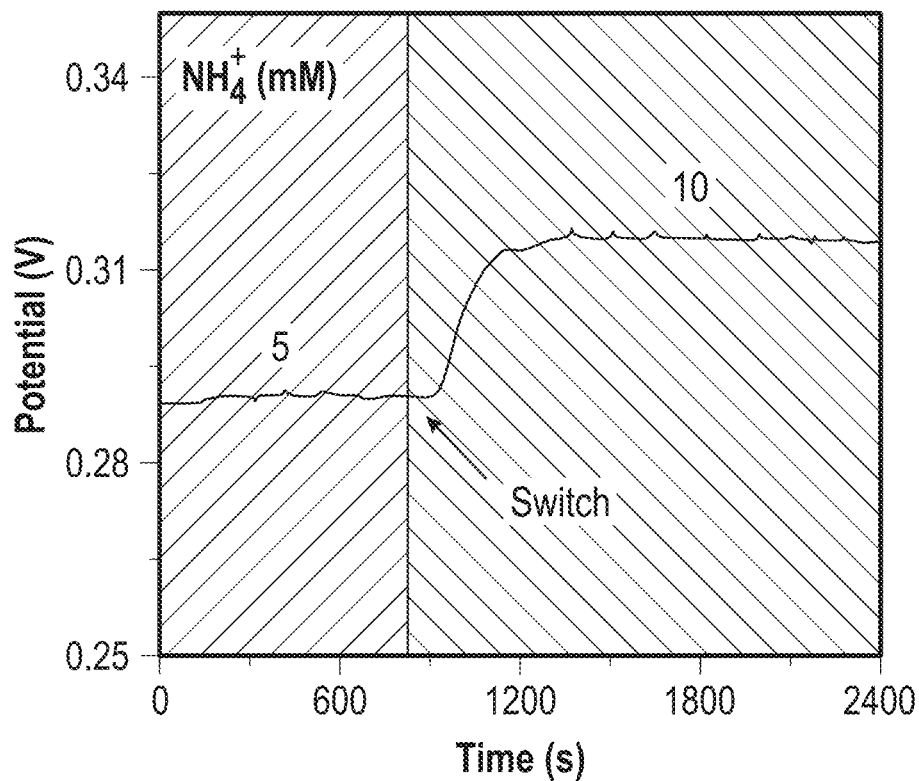
FIG. 6A illustrates, by way of example, target molecule detection and quantification in accordance with various embodiments of the disclosure.
Figure 6B:
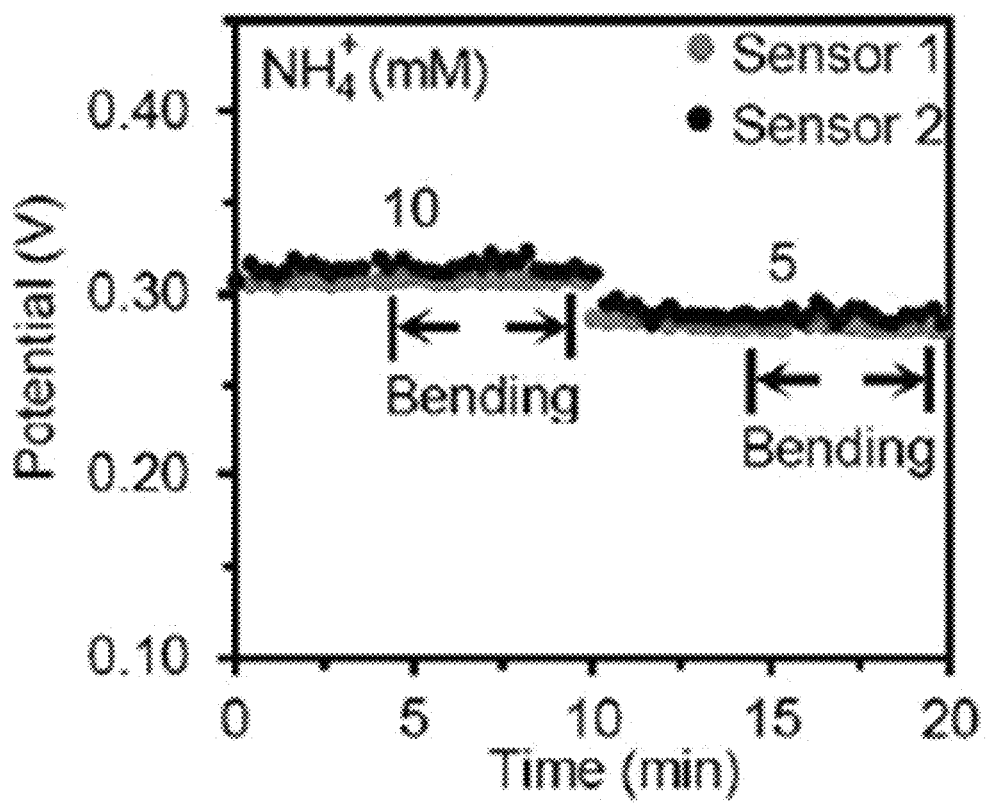
FIG. 6B illustrates, by way of example, target molecule detection and quantification in accordance with various embodiments of the disclosure.
Figure 6C:
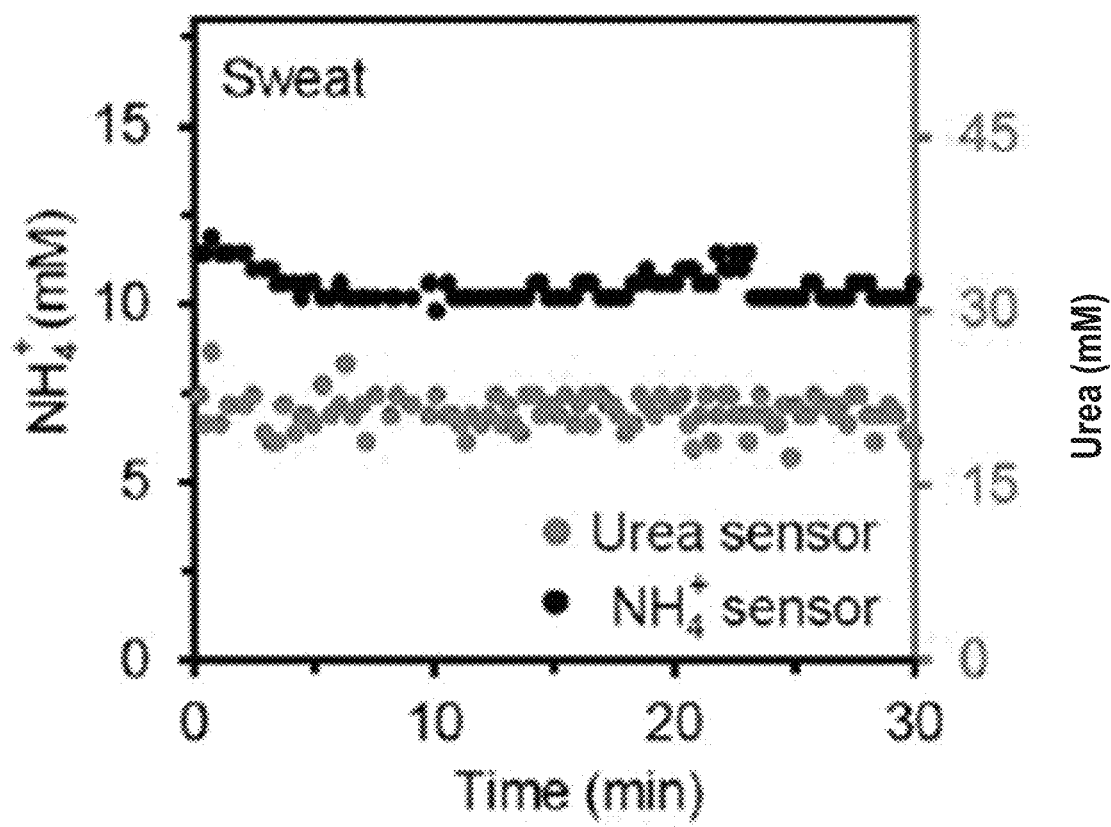
FIG. 6C illustrates, by way of example, target molecule detection and quantification in accordance with various embodiments of the disclosure.

FIGS. 6A-6C illustrate in-vitro validation of various systems and methods disclosed herein. FIG. 6A, for example, depicts an in-vitro flow test confirming that when the $NH_4^+$ level in the input solution is switched to a higher concentration (e.g., 50 to 10 mM) at a physiologically measured sweat rate of 0.05 ml $h^{-1}$, it takes around 4 minutes for the $NH_4^+$ sensor to reach stable reading, indicating minimal time delay for on-body monitoring. FIG. 6B, for example, depicts that even under mechanical deformation (e.g., bending curvature of 1.5 cm in radius) various sensors disclosed herein maintain consistent reading. FIG. 6C depicts stable performance in analyte monitoring over long periods of time.

Figure 7A:
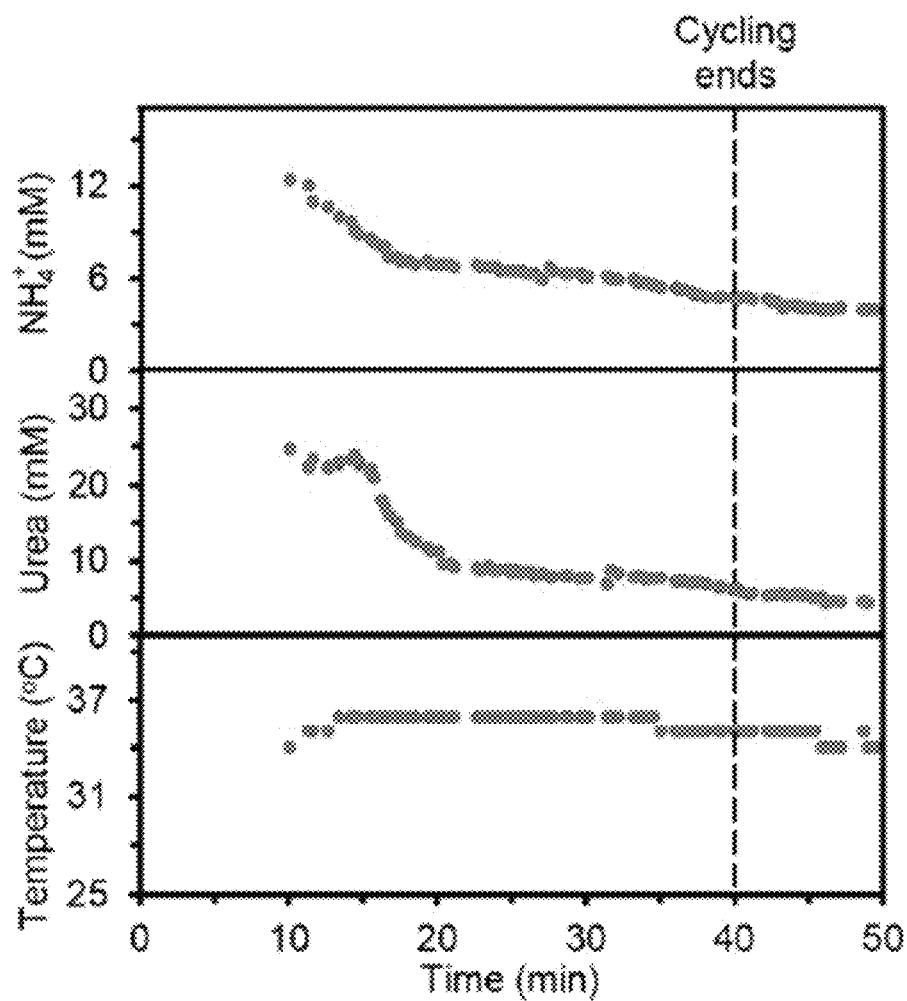
FIG. 7A illustrates, by way of example, on-body validation of an auto-powered biosensor in accordance with various embodiments of the disclosure.
Figure 7B:
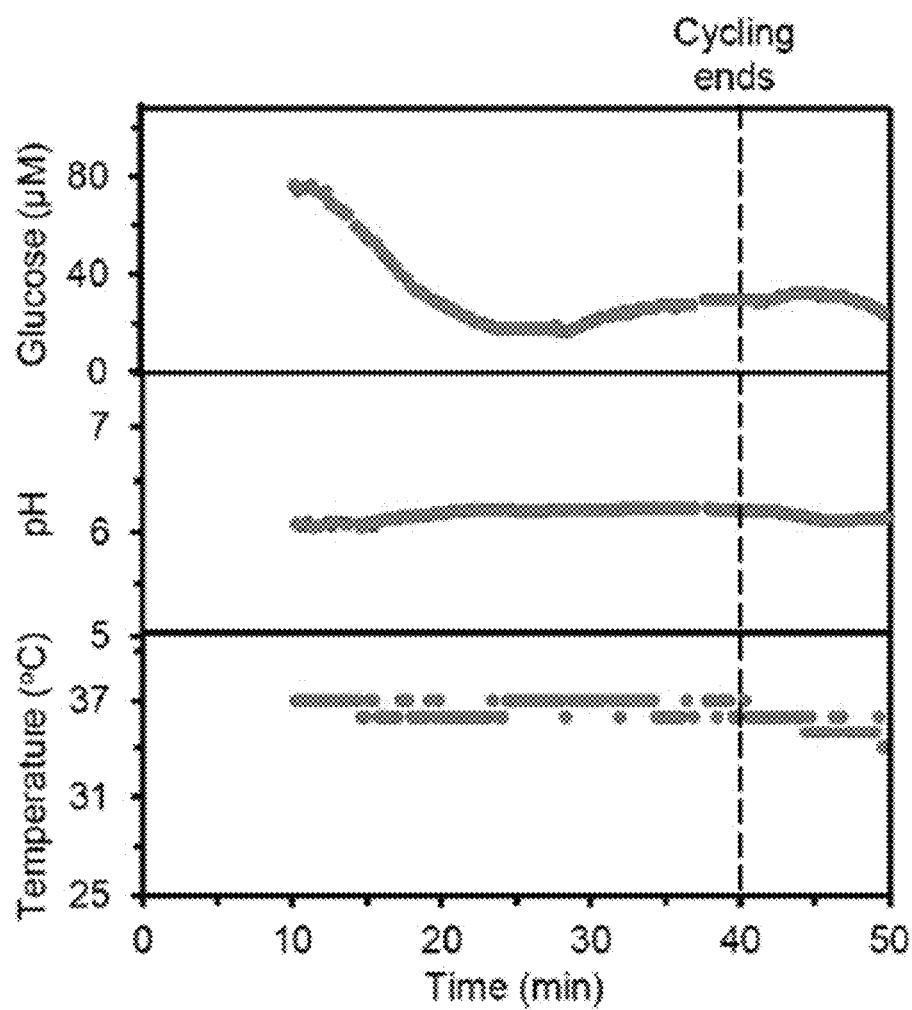
FIG. 7B illustrates, by way of example, on-body validation of an auto-powered biosensor in accordance with various embodiments of the disclosure.
Figure 7C:
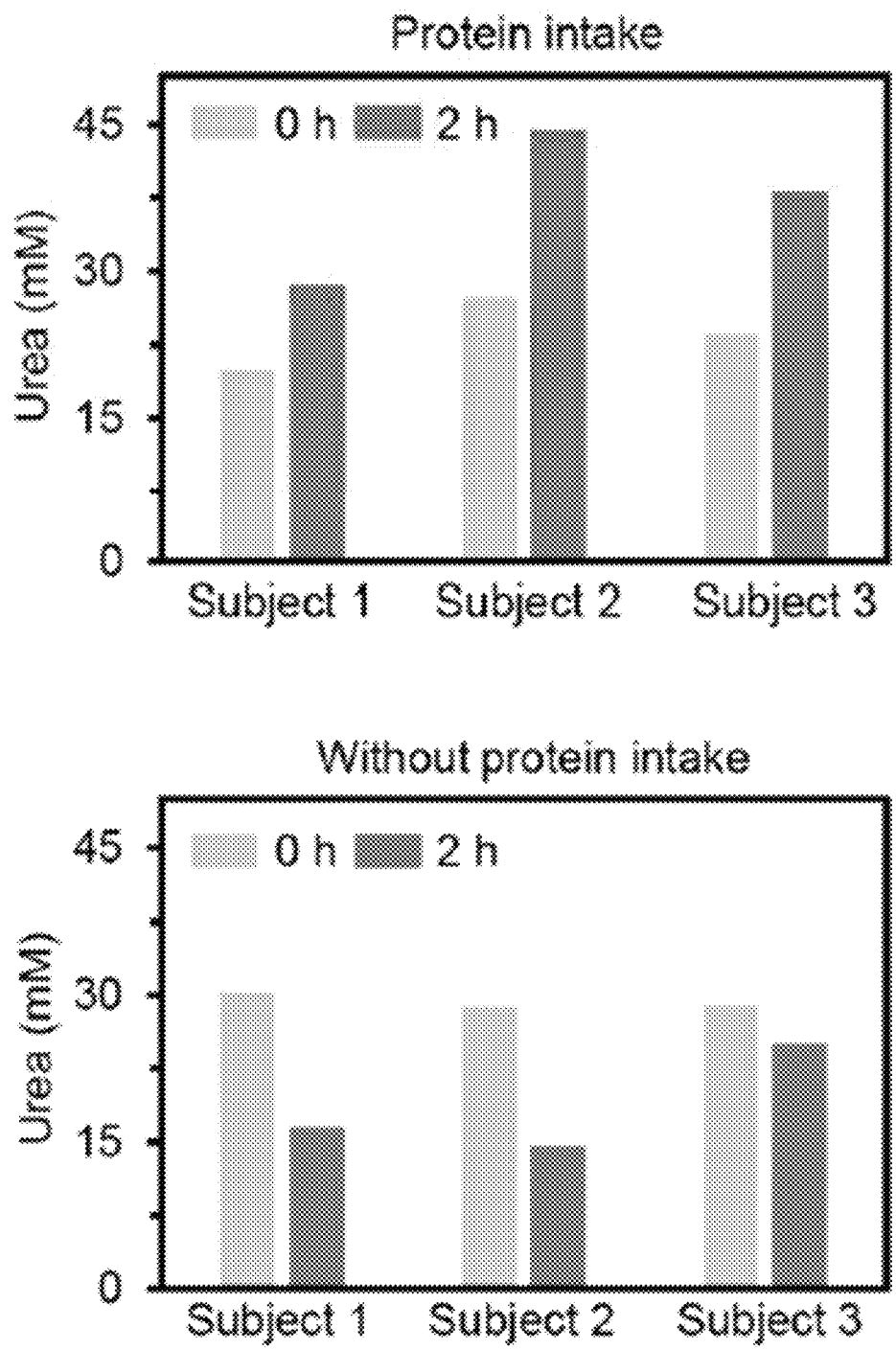
FIG. 7C illustrates, by way of example, on-body validation of an auto-powered biosensor in accordance with various embodiments of the disclosure.
Figure 7D:
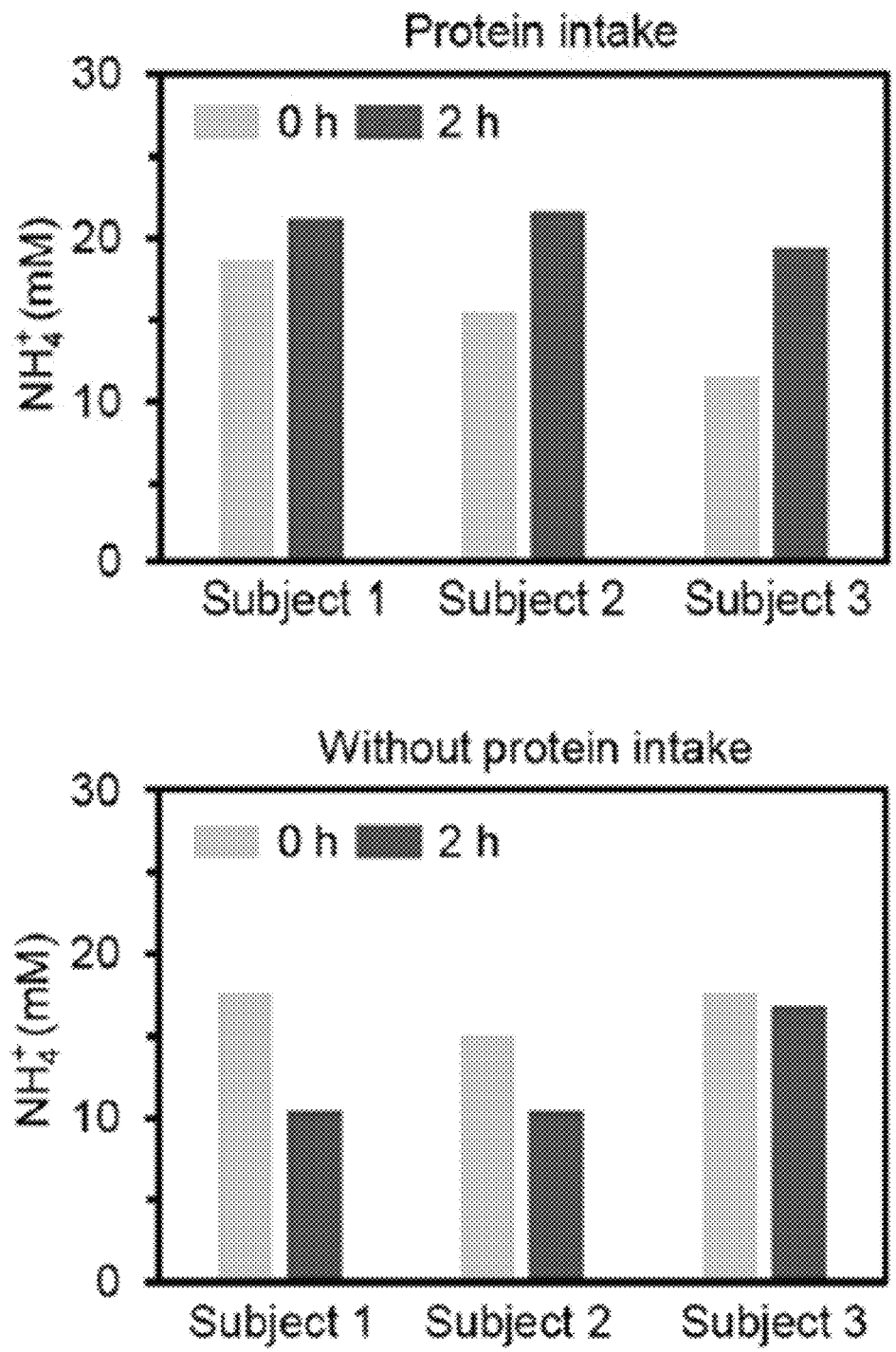
FIG. 7D illustrates, by way of example, on-body validation of an auto-powered biosensor in accordance with various embodiments of the disclosure.
Figure 7E:
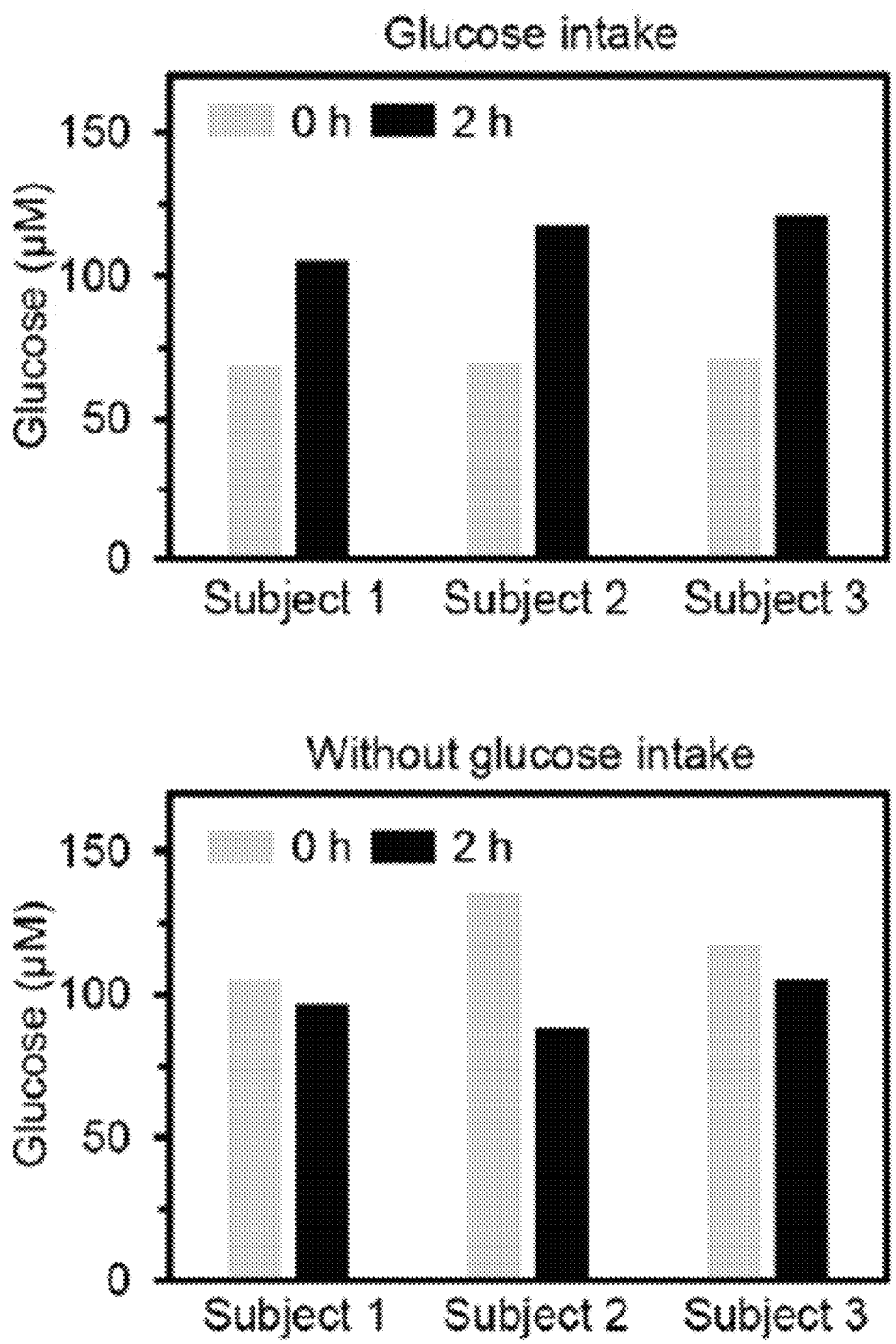
FIG. 7E illustrates, by way of example, on-body validation of an auto-powered biosensor in accordance with various embodiments of the disclosure.

FIGS. 7A-7E illustrate in-vivo validation of various systems and methods disclosed herein. For example, FIGS. 7A and 7B depict on-body validation of a biosensor placed on the forehead of a human subject in accordance with various embodiments of the disclosure. It is to be understood that the biosensor may be placed on different locations of the body, however. During exercise, physiological data may be continuously collected and analyzed for real-time multiplexed sensing of target molecules including, for example, urea, pH, $NH_4^+$, and glucose. Other physiological parameters may also be monitored by the biosensor, including for example, the temperature of the wearer. FIGS. 7C-7E illustrate active monitoring of target molecules after dietary challenges. For example, FIGS. 7C, 7D, and 7E depict changes in the subject's sweat urea, $NH_4^+$, and glucose levels after consuming protein or glucose, respectively.

Figure 8A:
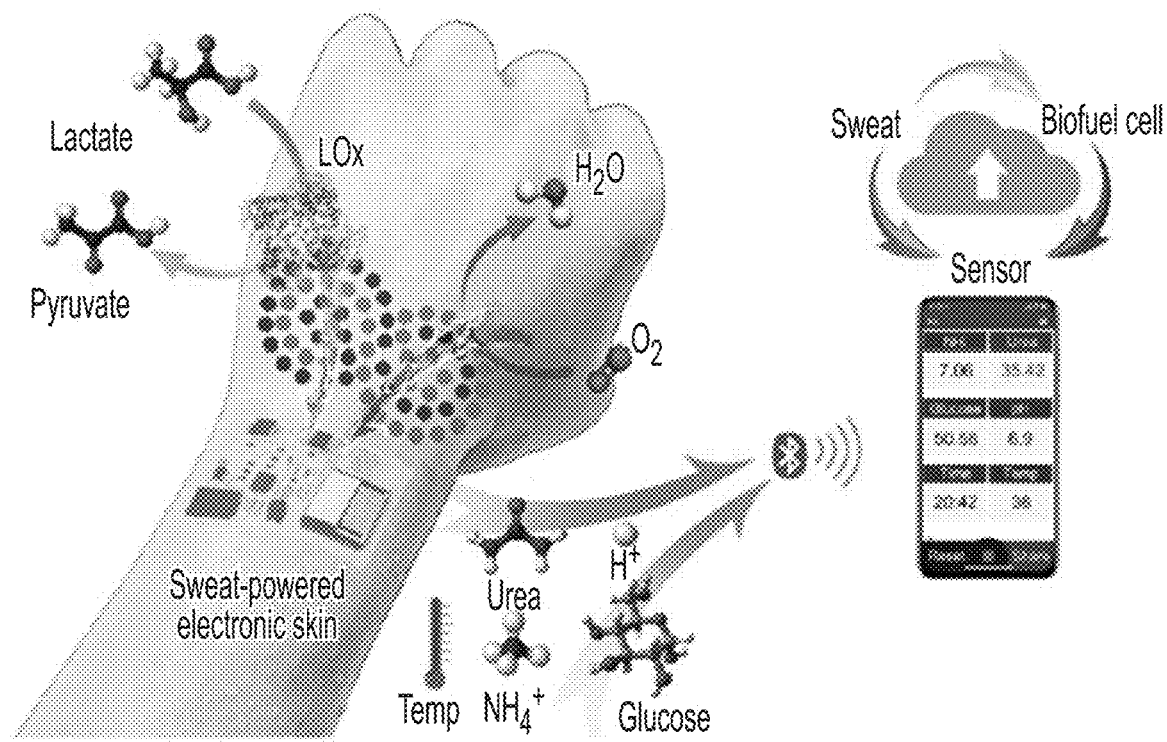
FIG. 8A illustrates, by way of example, implementations of an auto-powered biosensor in accordance with various embodiments of the disclosure.
Figure 8B:
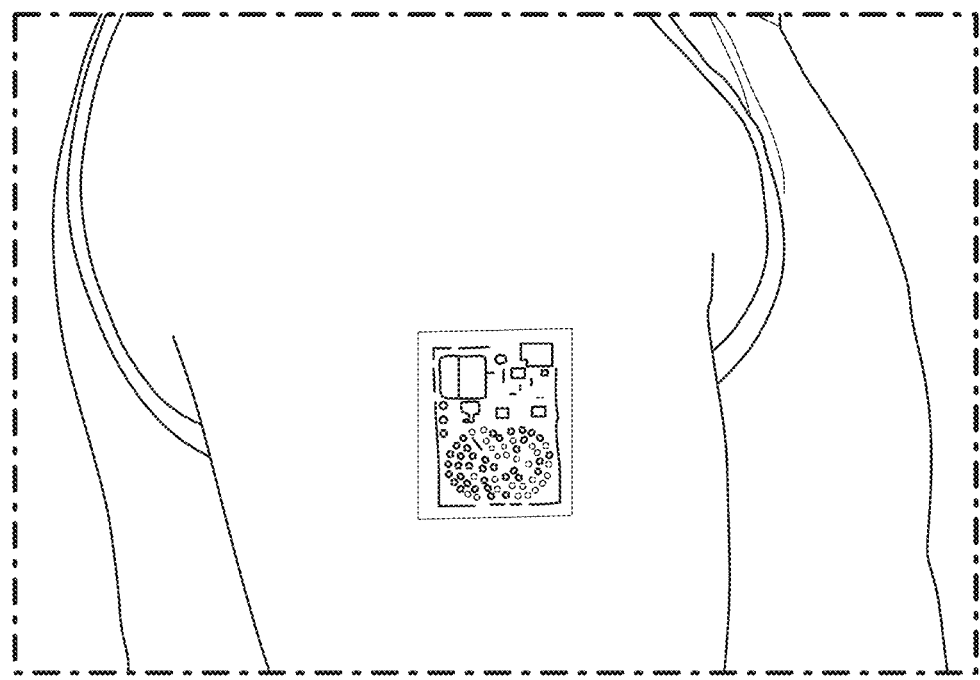
FIG. 8B illustrates, by way of example, implementations of an auto-powered biosensor in accordance with various embodiments of the disclosure.
Figure 8C:
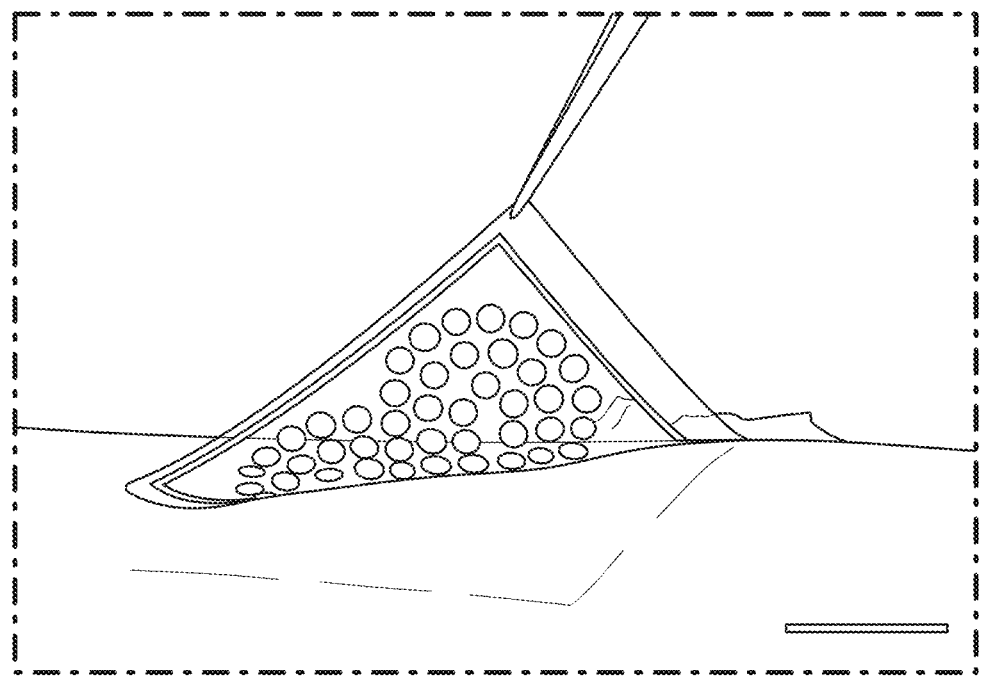
FIG. 8C illustrates, by way of example, implementations of an auto-powered biosensor in accordance with various embodiments of the disclosure.

FIGS. 8A-8C illustrate, by way of example, implementations of an auto-powered biosensor that may be used in accordance with the various systems and methods of the disclosure. FIG. 8A illustrates by way of example, an auto-powered biosensor. An auto-powered biosensor may include, for example, multiple electrodes including a chemical sensor, a resistance temperature sensor, and a piezoresistive sensor. The chemical sensor may be used to detect a target molecule, or multiple target molecules simultaneously, including for example, urea, $NH_4^+$, pH, and glucose; the resistance temperature sensor may be used to detect, for example, the body temperature of a user; and the piezoresistive sensor may be used to detect various vital signs of the user including, for example, heartrate and respiration rate. An auto-powered biosensor may also include one or more biofuel cells that may be used to continuously power the device through harvesting energy molecules found in a biological sample. Energy molecules may include, for example, lactate and oxygen. An auto-powered biosensor may also be capable of wirelessly transmitting data to a mobile device (e.g., a cellular phone) via Bluetooth® or other NFC technology. FIG. 8B illustrates how an auto-powered biosensor may be worn on various body parts of the user, including, for example, on the neck, arm, chest, back, and/or forehead of the user due to its compact, flexible, and lightweight structure. FIG. 8C illustrates how an auto-powered biosensor may be attached to a wearer's skin by one or more adhesives, including for example, medical tape (M-tape).

Referring again to FIG. 1, biosensor 100 may also include a logic circuit 150. In embodiments, logic circuit 150 may be electrically coupled to electrode 140 and may include a processor and a non-transitory memory with computer executable instructions embedded thereon. In various embodiments, logic circuit 150 may also include other circuits receiving, processing, and/or storing content, data, and other information. Logic circuit 150 may also, for example, facilitate the receipt of such content, data, or other information, as well as the generation of such content, data, or other information by the biosensor 100.

Figure 9A:
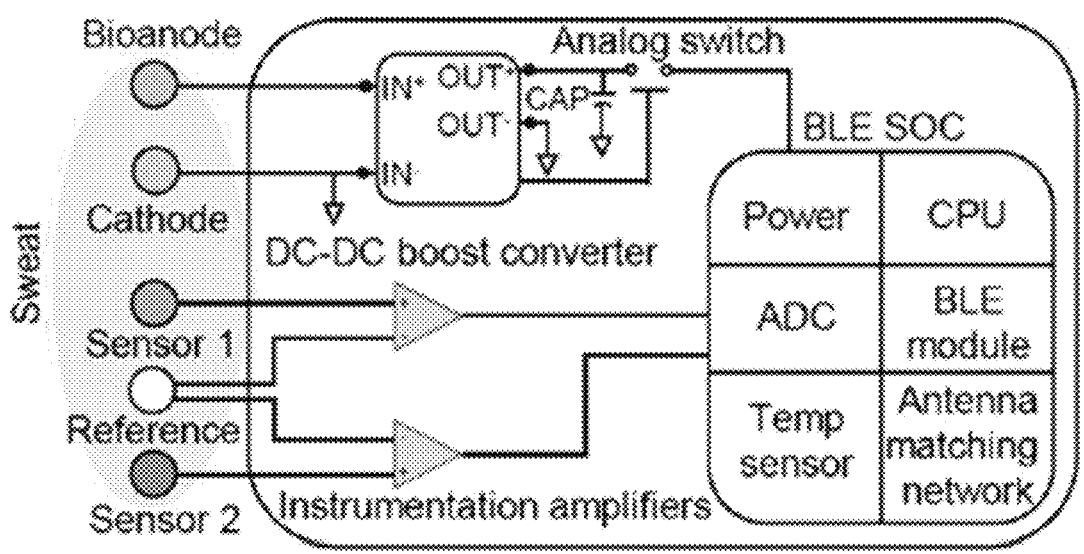
FIG. 9A illustrates, by way of example, circuitry that may be used by an auto-powered biosensor in accordance with various embodiments of the disclosure.
Figure 9B:
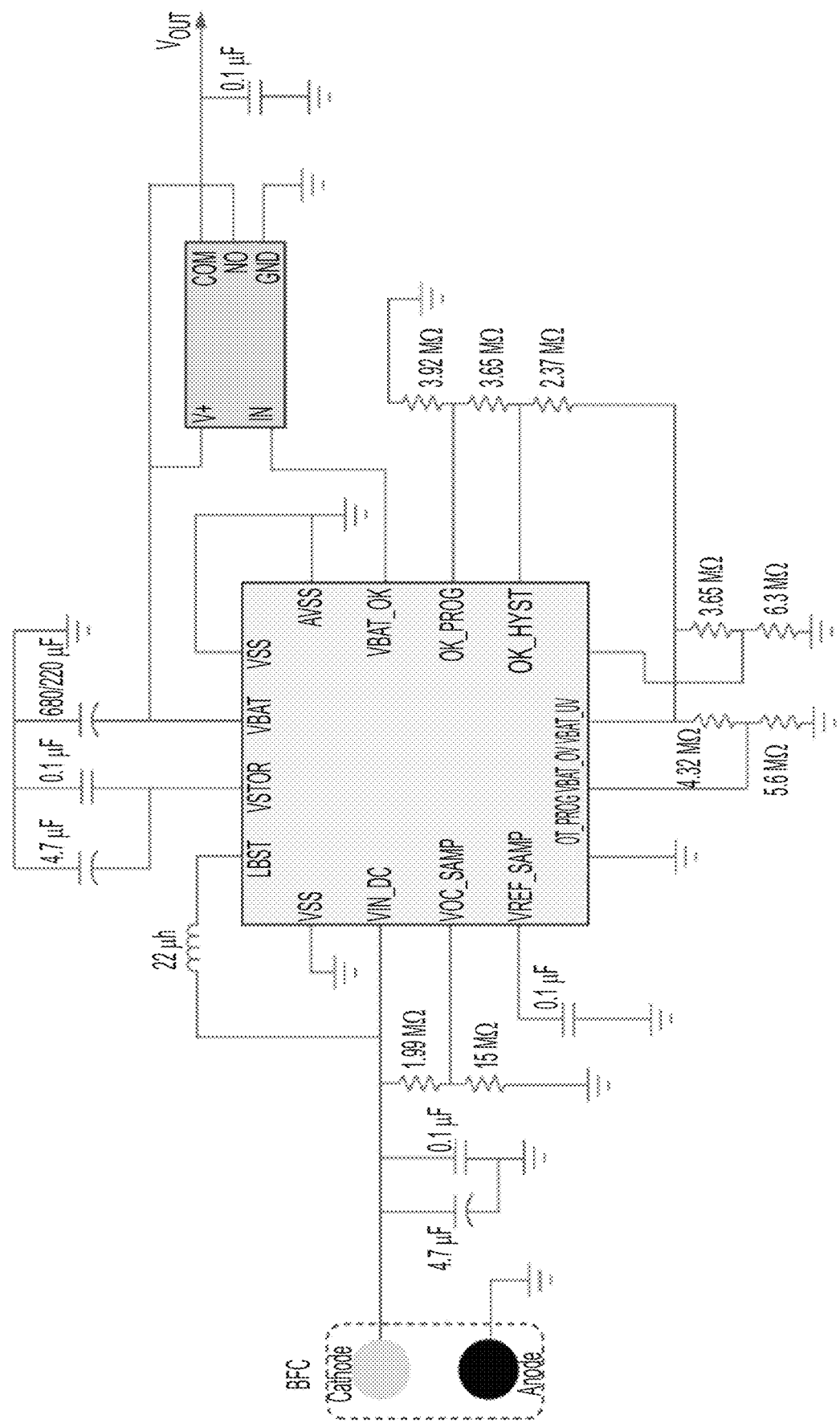
FIG. 9B illustrates, by way of example, circuitry that may be used by an auto-powered biosensor in accordance with various embodiments of the disclosure.

FIGS. 9A-9B illustrate, by way of example, circuitry that may be implemented by an auto-powered biosensor, in accordance with various embodiments of the disclosure. For example, FIG. 9A illustrates a circuit diagram that may be used by the systems and methods disclosed herein. A circuit diagram may include, for example, a biofuel cell array, an electrode sensor array, a boost converter, instrumentation amplifiers, and a Bluetooth® Low Energy (BLE) module. A more detailed circuitry for a biofuel cell array is depicted in FIG. 9B.

In embodiments, the computer executable instructions embedded within logic circuit 150 cause the processor to identify the electrical property detected with electrode 140. In some embodiments, the computer executable instructions embedded within logic circuit 150 cause the processor to identify the electrical property detected with electrode 140 when the target molecule is present in the biological sample. In some embodiments, the computer executable instructions embedded within logic circuit 150 cause the processor to identify the electrical property detected with electrode 140, wherein the electrical property is a change in temperature, strain, pressure, and/or resistance.

In some embodiments, the computer executable instructions embedded within logic circuit 150 cause the processor to generate an indication identifying the presence of the target molecule based on the electrical property detected by electrode 140. In some embodiments, the computer executable instructions embedded within logic circuit 150 cause the processor to generate an indication of a detected electrical property by electrode 140. In some embodiments, an electrical property may include, for example, voltage, amplitude, temperature, and/or resistance.

In embodiments, the indication generated by the processor may be transmitted electrically to a display to be identified visually. In some embodiments, the indication may be transmitted electrically to an LED, or a plurality of LEDs, to be identified visually. In embodiments, the indication generated may be stored on the non-transitory memory of logic circuit 150. In some embodiments, the indication generated may be transmitted wirelessly to another electronic device. For example, the indication generated may be transmitted wirelessly via Bluetooth® or over Wi-Fi.

In various embodiments, logic circuit 150 may output the indication identifying the presence of the target molecule in accordance with various embodiments of the disclosure. In some embodiments, upon the detection of the measurement of an electrical property of a target molecule with electrode 140, the computer executable instructions of logic circuit 150 further cause the processor to output the indication identifying the presence of the target molecule. The indication may be outputted to a mobile device. In some embodiments, upon the detection of the measurement of a vital sign of a user with electrode 140, the computer executable instructions of logic circuit 150 further cause the processor to output the indication identifying the measurement of the vital sign to a mobile device. In embodiments, a display of the mobile device may display visually the indication identifying the presence of the target molecule and/or the measurement of the vital sign. In some embodiments, the display may include an LCD screen. In some embodiments, the indication displayed may include a visual representation of the measurement of the electrical property, including, for example, an electrical current and/or an electrical voltage. In some embodiments, the indication displayed may include a measurement of a vital sign, including for example, heart-rate, respiration rate, and/or temperature of the user. In some embodiments, the indication displayed may include a visual representation of the measurement of the electrical property, including for example, a change in the electrical current and/or voltage. In some embodiments, the indication displayed may include a visual representation of the measurement of the electrical property, including for example, a change in the electrical impedance. In some embodiments, the visual representation may include, for example, a graph having an x and y-axis. In some embodiments, the indication may include a quantification of the amount of target molecule present in the biological sample. In some embodiments, the indication may include a change in measurement of a vital sign, including for example, change in temperature, change in respiration rate, and change in heartrate. In some embodiments, the quantification of target molecule present in a biological sample may include units of potential (e.g., voltage or "V"), current (e.g., amps or "A"), and/or impedance (e.g., ohms or "Z"). In some embodiments, the vital sign measurement may include, for example, units of degrees (e.g., ° F. and/or ° C.) oxygen consumption (VO2, in mL/kg/min), and beats per minute (bpm). In some embodiments, various amounts of each of these units may include nano-units, micro-units, milli-units, and/or liter-units.

Figure 10A:
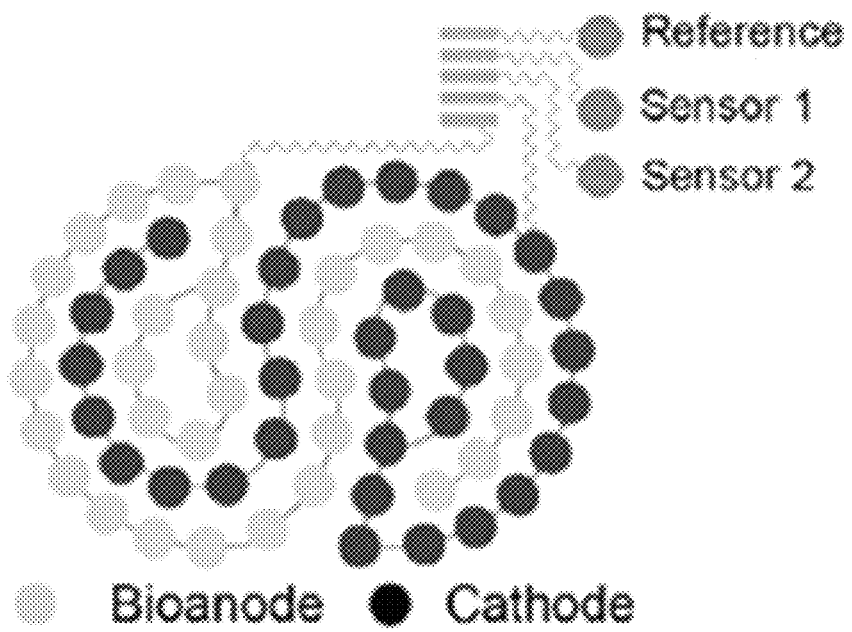
FIG. 10A illustrates by way of example, implementations of an auto-powered biosensor in accordance with various embodiments of the disclosure.
Figure 10B:
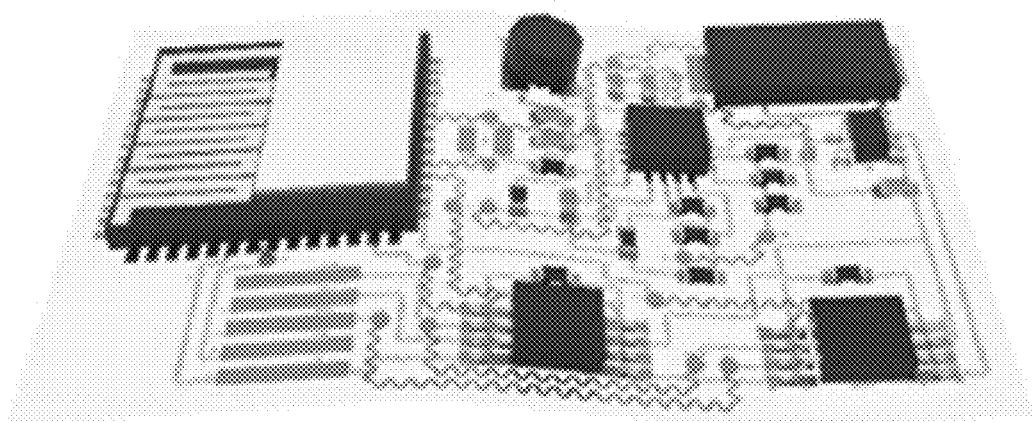
FIG. 10B illustrates by way of example, implementations of an auto-powered biosensor in accordance with various embodiments of the disclosure.
Figure 10C:
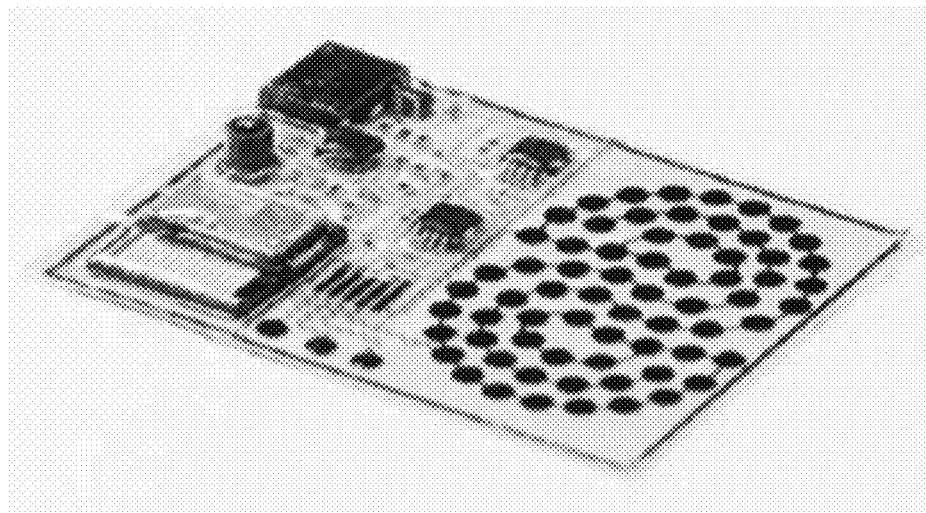
FIG. 10C illustrates by way of example, implementations of an auto-powered biosensor in accordance with various embodiments of the disclosure.

FIGS. 10A-10C illustrate, by way of example, various implementations of an auto-powered biosensor disclosed herein. For example, FIG. 10A illustrates a multimodal sensing layer array that includes a biofuel cell including a bioanode and a cathode, and one or more sensors. FIG. 10B illustrates, for example, a circuit that may be integrated to create an auto-powered biosensor capable of multiplexed sensing. FIG. 10C illustrates, for example, a fully integrated auto-powered biosensor wherein an indication generated may be wirelessly transmitted to a mobile device for viewing.

Figure 11:
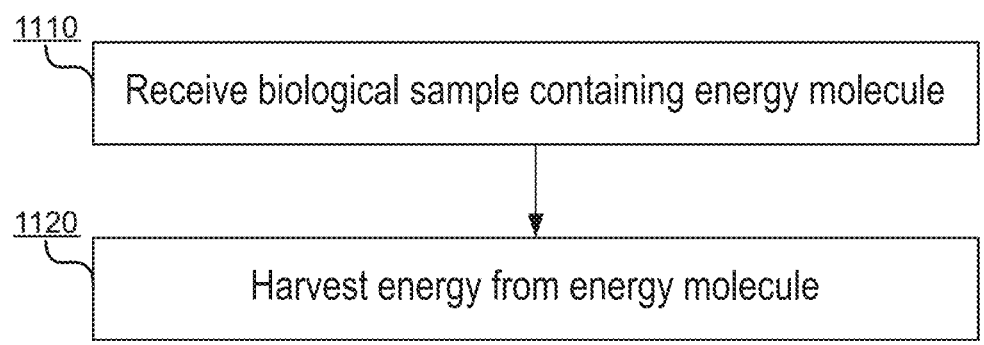
FIG. 11 is an operational flow diagram illustrating an example method for powering an auto-powered biosensor, in accordance with various implementations of the disclosure.

FIG. 11 is a flow diagram illustrating an example method in accordance with the technology disclosed. At a high level, method 1100 may be performed to power a biosensor in accordance with various embodiments of the disclosure. The operations of the various methods described herein are not necessarily limited to the order described or shown in the figures, and one of skill in the art will appreciate, upon studying the present disclosure, variations of the order of the operations described herein that are within the spirit and scope of the disclosure. Let it be appreciated that operations of method 1100 may be performed multiple times.

The operations and sub-operations of method 1100 may be carried out, in some cases, using one or more of the components, elements, devices, and sub-components of biosensor 100, as described with respect to at least FIGS. 1-10, as well as components, elements, devices, and sub-components, depicted therein and/or described with respect thereto.

In such instances, the description of method 1100 may or may not refer to a corresponding component and/or element, but regardless of whether an explicit reference is made, one of skill in the art will recognize, upon studying the present disclosure, when the corresponding component and/or element may be used. Further, it will be appreciated that such references do not necessarily limit the described method to the particular component and/or element referred to. Thus, it will be appreciated by one of skill in the art that aspects and features described above in connection with (sub-) components, elements, devices, and components, including variations thereof, may be applied to the various operations described in connection with method 1100 without departing from the scope of the present disclosure.

Referring now to FIG. 11, method 1100 may be used for powering biosensor 100, in accordance with implementations of the disclosure. At operation 1110, a biological sample that may include an energy molecule and a target molecule is received by biosensor 100. In embodiments, the biological sample may be received by biosensor 100 when the biological sample is collected by the microfluidics layer 110. For example, where the biological sample is sweat, the biological sample may be collected by microfluidics layer 110 directly from the skin of the wearer. Where the biological sample is saliva, for example, the biological sample may be collected from the wearer's mouth or through a tube or other device that funnels saliva to the microfluidics layer 110. Other, non-limiting ways the biological sample may be collected by microfluidics layer 110 include through pipetting, syringe injection, column feeding, micro-pumping, and various machine-automated methods. In embodiments, receiving a biological sample that includes an energy molecule further includes channeling the biological sample through the microfluidics layer 110 to the multimodal sensing layer 120. It is to be understood that the biological sample may contain more than one energy molecule and that more than one energy molecule may be channeled through the microfluidics layer to the multimodal sensing layer.

In embodiments, the energy molecule may be used to power the biosensor 100. Several different biological samples including, for example, blood, sweat, tears, urine, saliva, and/or breath condensation (e.g., condensed vapor) may be received by biosensor 100. Energy molecules present within the biological sample may vary depending on the biological sample. For example, energy molecules found commonly in sweat may include oxygen, hydrogen, magnesium, calcium, potassium, sodium, bicarbonate, ammonia, sulfate, lactate, amino acids, chloride, etc. The amount or concentration of the energy molecule in the biological sample may depend on the energy molecule, and the biological sample. More than one energy molecule may be used to power the various biosensors disclosed herein. A person of ordinary skill in the art would understand that various different energy molecules may be obtained from a biological sample, depending on the biological sample received by the biosensor.

At operation 1120, energy may be harvested from the energy molecule so that it may be used to power biosensor 100. In embodiments, harvesting energy from the energy molecule may be performed by biofuel cell 130. In embodiments, more than one biofuel cell 130 may be used to harvest energy from more than one energy molecule. In embodiments, harvesting energy from the energy molecule may include an enzymatic reaction, whereby certain enzymes are employed to catalyze the reaction. In embodiments, harvesting energy from the energy molecule may include a redox reaction (i.e., oxidation-reduction reaction), whereby one molecule loses or gains an electron. In embodiments, an enzymatic reaction and redox reaction may be performed simultaneously, depending on the energy molecule. For example, in certain embodiments where the biofuel cell includes a lactate oxidase (LOx) immobilized anode, harvesting energy from lactate may include using the enzyme lactate oxidase to oxidize lactate to pyruvate. In embodiments where the biofuel cell includes a Pt-alloy cathode, harvesting energy from oxygen may include reducing oxygen to water. In embodiments, the transfer rate of the electrons during energy harvesting may be enhanced by including certain materials within the anodes and cathodes, including for example, hierarchal Ni microstructures (h-Ni), reduced graphene oxide (rGO) films, and a bimediator modified carbon nanotube (CNT) network, including, for example, Meldola's Blue-tetrathiafulvalene modified carbon nanotubes (MDB-TTF-CNT). In embodiments, the pi-pi interaction between the CNTs and rGO significantly enhance the electron transfer rate between the LOx and electrodes, and the TTF-MDB redox mediator may decrease the overpotential of the lactate oxidation reaction. In embodiments, biosensor 100 may also include a capacitor. In embodiments, biosensor 100 may include more than one capacitor. In embodiments, the biofuel cell may be coupled to a capacitor. In embodiments, the energy harvested from the energy molecule may be stored in a capacitor. In embodiments, energy needed to power the biosensor may be channeled from a capacitor by and through the various circuitry of the biosensor disclosed herein.

In embodiments, biosensor 100 of FIG. 1 may be used to detect a target molecule in a biological sample. In embodiments, a biological sample may include an excreted bodily fluid, such as, for example, sweat, urine, tears, blood, salvia, and secretions from the male and female sex organs. Target molecules may include proteins (including viral proteins), antibodies, electrolytes, vitamins, amino acids, metabolized drugs, among other molecules and/or compounds. In some embodiments, a target molecule may include, for example, tryptophan, tyrosine, phenylalanine, dopamine, vitamin C, vitamin B6, vitamin B12, uric acid, mycophenolic acid, caffeine, methionine, cortisol, noradrenaline, or adrenaline. In embodiments, a target molecule may include, for example, leucine, iso-leucine, valine, busulfan, cyclophosphamide, creatinine, urea, $NH_4^+$, glucose, hydrogen ions, or other ions. The lists of electroactive and non-electroactive molecules are not meant to be exhaustive. It is to be understood that additional molecules not listed here, may also be detected according to the various systems and methods disclosed herein.

In various embodiments, a target molecule may include an amino acid. Amino acids that may be detected using embodiments of the disclosure include: alanine; glycine; isoleucine; leucine; proline; valine; phenylalanine; tryptophan; tyrosine; aspartic acid; glutamic acid; arginine; histidine; lysine; serine; threonine; cysteine; methionine; asparagine; and glutamine.

In various embodiments, a target molecule may include antibodies against viral nucleocapsid proteins or other virus-specific identifiers (i.e., epitope). For example, monoclonal antibodies against the SARS-CoV-2 nucleocapsid protein may be detected. Other monoclonal antibodies that are designed to detect other epitopes of the virus or other viruses may also be used as a target molecule. In some embodiments, other virus-specific target molecules, including molecules secreted by the virus, building block molecules of the virus, and genetic elements of the virus may also be a target molecule and be detected using technology disclosed herein.

In various embodiments, a target molecule may include a vitamin or provitamin (i.e., vitamin precursors). For example, vitamins and provitamins that may be detected include: thiamine (vitamin B1); riboflavin (vitamin B2); niacin (vitamin B3); choline (vitamin B4); pantothenic acid (vitamin B5); pyridoxine (vitamin B6); biotin (vitamin H, vitamin B7, or vitamin B8); folic acid (vitamin B9 or folate); and cobalamin (vitamin B12); ascorbic acid (vitamin C); retinol (vitamin A); calciferol (vitamin D); tocopherol (vitamin E); phylloquinone (vitamin K1); menaquinone (vitamin K2); β-carotene (vitamin A); 7-dehydrocholesterol (vitamin D); and cholecalciferol (vitamin D).

In various embodiments, the target molecule may include, for example, a hormone. Hormones that may be detected include: cholesterol; cortisol; progesterone; testosterone; corticosterone; aldosterone; β-estradiol; insulin; estrogen; thyroxin; gonadotropin-releasing hormone (GnRH); corticotropin-releasing hormone; melatonin; human growth hormone (HGH); adrenocorticotropic hormone; prolactin; and angiotensin. In some embodiments, a target molecule may include a protein used for diagnosis purposes, including for detecting and monitoring various illnesses (e.g., cancer). For example, a target molecule may include tumor markers for detecting and monitoring cancer, including: serum carcinoembryonic antigen (CEA); serum lipid-associated sialic acid (LASA); serum cancer antigen 19-9 (CA 19-9); cancer antigen 125 (CA 125); alpha fetoprotein (AFP); lactase dehydrogenase (LDH); and human chorionic gonadotropin (hCG). The list of target molecules is not meant to be exhaustive. It is to be understood that additional target molecules not listed here, may also be detected according to the various systems and methods disclosed herein.

In certain embodiments, biosensor 100 may be used to detect and measure quantity of a target molecule in a biological sample, and/or determine the vital signs of a user. For example, medical, veterinary, research staff, law enforcement, or other interested personnel can use the disclosed technology to detect the presence and/or measure the quantity of a target molecule in a biological sample. Furthermore, the same interested personnel may use the disclosed technology to determine certain vital signs and/or temperature of a subject wearing biosensor 100. By identifying certain target molecules including, for example, drug metabolites, and/or vital signs, including respiratory rate and heartrate, interested personnel can determine if a subject (e.g., a human, animal, or organism) has taken a certain drug and/or may observe whether a subject is in compliance in taking prescription medications. Moreover, by identifying certain target molecules, including certain metabolites and amino acids, and by identifying certain vital signs, an interested personnel can determine if a subject is experiencing a certain medical issue, or diagnose a certain medical issue. Embodiments of the technology disclosed herein enable analysis locally at the biosensor without the need for separate equipment, resulting in a less complex system that is smaller and portable. This makes it easier for interested personnel and subjects to view the biosensor data at the device, eliminating the need to utilize other equipment, e.g., enabling field tests for detection of illicit drugs in a subject, or compliance with a drug regiment by the subject. Moreover, embodiments herein allow for continuous on-body use of the biosensor without the need for a battery or external charging device.

Figure 12:
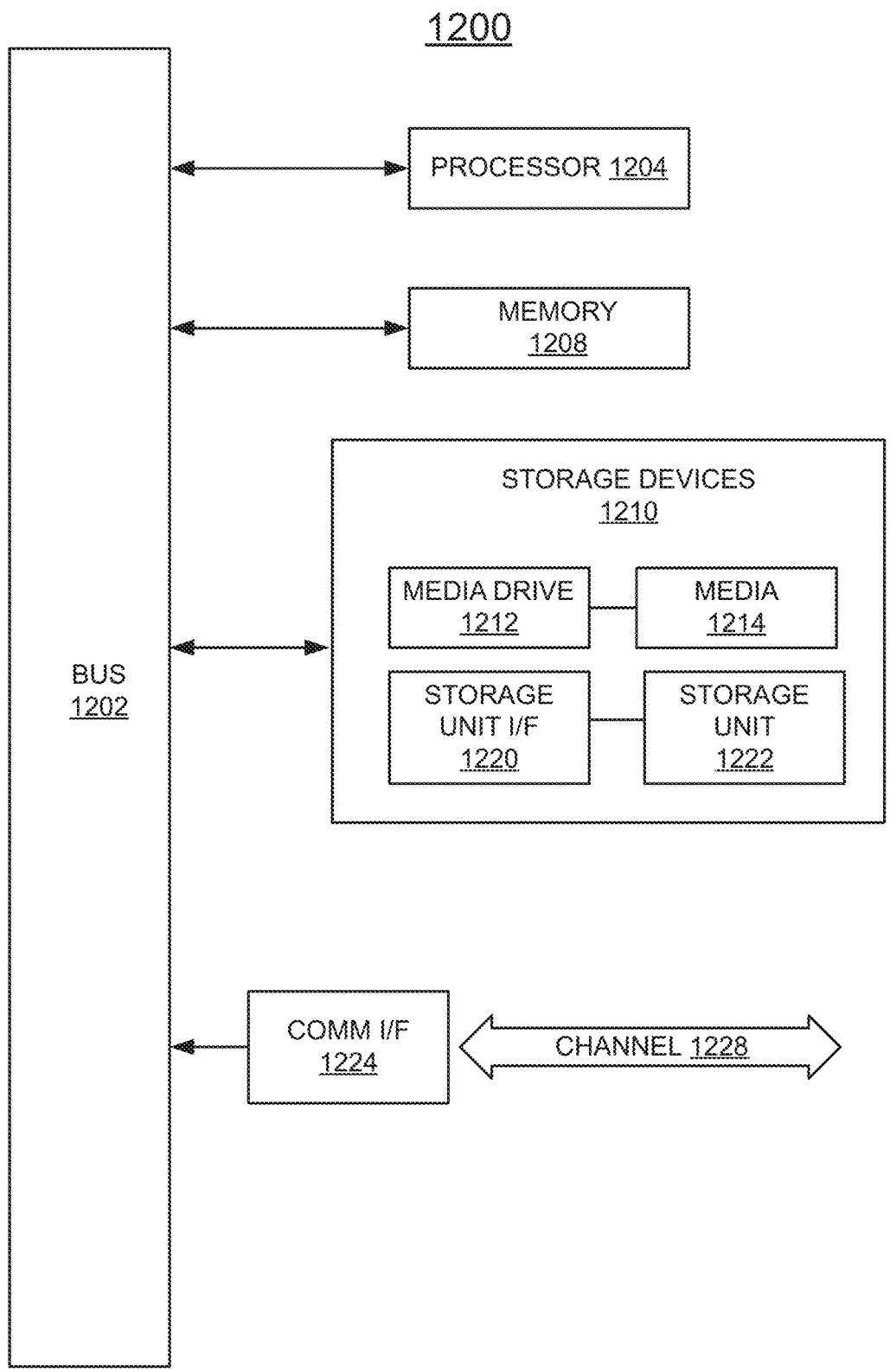
FIG. 12 illustrates a computer component that can be utilized in implementing architectures and methods, in accordance with various implementations of the disclosure.

FIG. 12 illustrates example computing component 1200, which may, in some instances, include a processor/controller resident on a computer system (e.g., biosensor 100). Computing component 1200 may be used to implement various features and/or functionality of embodiments of the systems, devices, and methods disclosed herein. With regard to the above-described embodiments set forth herein in the context of systems, devices, and methods described with reference to FIGS. 1 through 11, including embodiments involving biosensor 100, one of skill in the art will appreciate additional variations and details regarding the functionality of these embodiments that may be carried out by computing component 1200. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component references a module, and/or may be implemented utilizing any form of hardware, software, or a combination thereof. For example, one or more processors, controllers, ASICs, PLAs, PALs, CPLDs, FPGAs, logical components, software routines or other mechanisms may be implemented to make up a component. In embodiment, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components of the application are implemented in whole or in part using software, in one embodiment, these software elements can be implemented to operate with a computing or processing component capable of carrying out the functionality described with respect thereto. One such example computing component is shown in FIG. 12. Various embodiments are described in terms of this example computing component 1200. After reading this description, it will become apparent to a person skilled in the relevant art how to implement the application using other computing components or architectures.

Referring now to FIG. 12, computing component 1200 may represent, for example, computing or processing capabilities found within a self-adjusting display, desktop, laptop, notebook, and tablet computers; hand-held computing devices (tablets, PDA's, smart phones, cell phones, palmtops, etc.); workstations or other devices with displays; servers; or any other type of special-purpose or general-purpose computing devices as may be desirable or appropriate for a given application or environment. Computing component 1200 might also represent computing capabilities embedded within or otherwise available to a given device. For example, a computing component might be found in other electronic devices such as, for example, navigation systems, portable computing devices, and other electronic devices that might include some form of processing capability.

Computing component 1200 might include, for example, one or more processors, controllers, control components, or other processing devices, such as a processor 1204. Processor 1204 might be implemented using a general-purpose or special-purpose processing engine such as, for example, a microprocessor, controller, or other control logic. In the illustrated example, processor 1204 is connected to a bus 1202, although any communication medium can be used to facilitate interaction with other components of computing component 1200 or to communicate externally.

Computing component 1200 might also include one or more memory components, simply referred to herein as main memory 1208. For example, preferably random access memory (RAM) or other static or dynamic memory, might be used for storing information and instructions to be executed by processor 1204. Main memory 1208 might also be used for storing temporary variables or other intermediate information during execution of instructions to be executed by processor 1204. Computing component 1200 might likewise include a read only memory ("ROM") or other static storage device coupled to bus 1202 for storing static information and instructions for processor 1204.

The computing component 1200 might also include one or more various forms of information storage mechanism 1210, which might include, for example, a media drive 1212 and a storage unit interface 1220. The media drive 1212 might include a drive or other mechanism to support fixed or removable storage media 1214. For example, a hard disk drive, a solid state drive, a magnetic tape drive, an optical disk drive, a compact disc (CD) or digital video disc (DVD) drive (R or RW), or other removable or fixed media drive might be provided. Accordingly, storage media 1214 might include, for example, a hard disk, flash drive, an integrated circuit assembly, USB, magnetic tape, cartridge, optical disk, a CD or DVD, or other fixed or removable medium that is read by, written to or accessed by media drive 1212. As these examples illustrate, the storage media 1214 can include a computer usable storage medium having stored therein computer software or data.

In alternative embodiments, information storage mechanism 1210 might include other similar instrumentalities for allowing computer programs or other instructions or data to be loaded into computing component 1200. Such instrumentalities might include, for example, a fixed or removable storage unit 1222 and an interface 1220. Examples of such storage units 1222 and interfaces 1220 can include a program cartridge and cartridge interface, a removable memory (for example, a flash memory or other removable memory component) and memory slot, a PCMCIA slot and card, and other fixed or removable storage units 1222 and interfaces 1220 that allow software and data to be transferred from the storage unit 1222 to computing component 1200.

Computing component 1200 might also include a communications interface 1224. Communications interface 1224 might be used to allow software and data to be transferred between computing component 1200 and external devices. Examples of communications interface 1224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 1224 might typically be carried on signals, which can be electronic, electromagnetic (which includes optical) or other signals capable of being exchanged by a given communications interface 1224. These signals might be provided to communications interface 1224 via a channel 1228. This channel 1228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 1208, storage unit 1220, media 1214, and channel 1228. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 900 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The details of some embodiments of the systems and methods of the present disclosure are set forth in this description and in some cases, in other portions of the disclosure. Other features, objects, and advantages of the disclosure will be apparent to one of skill in the art upon examination of the present disclosure, description, figures, examples, and claims. It is intended that all such additional systems, methods, devices, features, and advantages be included within this description (whether explicitly or by reference), be within the scope of the present disclosure, and be protected by one or more of the accompanying claims.

EXAMPLES

Example 1: Fabrication of Biofuel Cells

In embodiments, to prepare the biofuel cell anodes, a graphene oxide (GO) suspension may be first prepared following a modified Hummer's method. Briefly, a mixture of 1 g graphite flake and 23 ml H2SO4 may be stirred over 24 hours, and then 100 mg NaNO3 may be added into the mixture. Subsequently, 3 g KMnO4 may be added to the mixture below 5 t in the ice bath. Following stirring at 40° C. for another 30 min, 46 ml $H_2O$ may then be added at 80° C. In embodiments, 140 ml H2O and 10 ml H2O2 (30%, w/v) may then be introduced into the mixture to complete the reaction. The GO may then be washed and filtered with 1 M HCl. The self-supported h-Ni may then be cut into 2-mm-diameter circles using a CO2 laser cutter and cleaned by ultrasonication in 4 M HCl for 30 nun until the color changed from black to silver. After drying, the h-Ni substrates may be immersed into a GO suspension with a concentration of 2.0 mg ml-1 in water for 1 hour. The h-Ni substrates may then be transferred into to 5 ml ascorbic acid (10 mg ml-1) overnight and heated at 75° C. for 2 hours. After cooling down to room temperature, the rGO/h-Ni composite electrodes may then be rinsed with water. The freestanding CNTs may then be immersed into 2 mM MDB

TABLE 1

Examples of Biofuel Cell Arrays

| No. | Bioanode | Cathode | Biofluid | Biofuel | Power output | OCP (V) | Ref |
|---|---|---|---|---|---|---|---|
| 1 | Pyranoase dehydrogenase/graphite | BOx/AuNPs/Au | Blood | Glucose | 73 $\mu W\ cm^{-2}$ | 0.56 | 49 |
| 2 | LDH/buckypaper | BOx/buckypaper | Tear | Lactate | 8.14 $\mu W\ cm^{-2}$ | 0.41 | 50 |
|   |   |   | Sweat |   | 0.26 $\mu W\ cm^{-2}$ | 0.58 | 51 |
| 3 | Cellobiose dehydrogenase/Au/NPd/Au | BOx/AuNPs/Au | Saliva | Glucose | 0.2 $\mu W\ cm^{-2}$ | 0.56 |   |
|   |   |   | Tear |   | 1 $\mu W\ cm^{-2}$ | 0.57 | 52 |
| 4 | Lox/NQ-CNT | CNT-$Ag_2O$ | Sweat | Lactate | 1.1 $mW\ cm^{-2}$ | 0.5 | 32 |
| 5 | CNT/TTP/LOx/chitosan | Platinum black | Sweat | Lactate | 44 $\mu W\ cm^{-2}$ | 0.5* | 34 |
| 6 | LOx/TTP-TCNO/CNT | Platinum black | Sweat | Lactate | 100 $\mu W\ cm^{-2}$ | 0.64 | 53 |
| 7 | LOx/TTF-MDB-CNT/rGO/h-Ni | Pt—Cu/MDB-CNT | Sweat | Lactate | 3.5 $mW\ cm^{-2}$ | 0.65 | This work |

BOx, bilirubin oxidase: LDH, lactate dehydrogenase; NPs, nanoparticles; NQ, 1,4-naphthoQuinone; TCNO: tetracyanoquinodimethane; OCP: open circuit potential.
Physiological range of the biofuels, Glucose: blood, 4.4-7.8 mM; saliva, 0.02-02.06 mm; TEAR, 0.2-0.9 Mm. Lactate: sweat, 5-60 mM.
*Acquired from provided figure.

TABLE 2

Proposed Mechanism of TTF-MDB Bimediator in Biofuel Cell

TTF and MDB can act as electron-transfer relay systems between bioanode and the flavin adenine dinucleotide (FAD)/FADH (the redox active centers of lactate oxidase protected by the protein shell). Generally, L-lactate is oxidized by the FAD of LOx, generating the reduced form LOx(FADH) as the following process:

L-lactate + LOx(FAD) → pyruvate + LOx(FADH)     (1)

Then, the LOx(FADH) is oxidized by the TTP/MDB mediator:

LOx(FADH) + 2TTF → LOx(FAD) + 2TTF + 2H$^+$     (2)

2TFF → 2TTF$^+$ + 2ē     (3)

LOx(FADH) + MDB$_{red}$ → LOx(FAD) + MDB$_{ox}$ + 2H$^-$     (4)

MDB$_{red}$ → MDB$_{ox}$ + ē     (5)

Electrons transfer from the mediators to the bioelectrode as shown in equation (3) and (5).
Without the additional mediator, the $O_2$ would be the oxidizer for the reduced LOx(FADH):

LOx(FADH) + $O_2$ → LOx(FAD) + $H_2O_2$     (6)

Figure 13A:
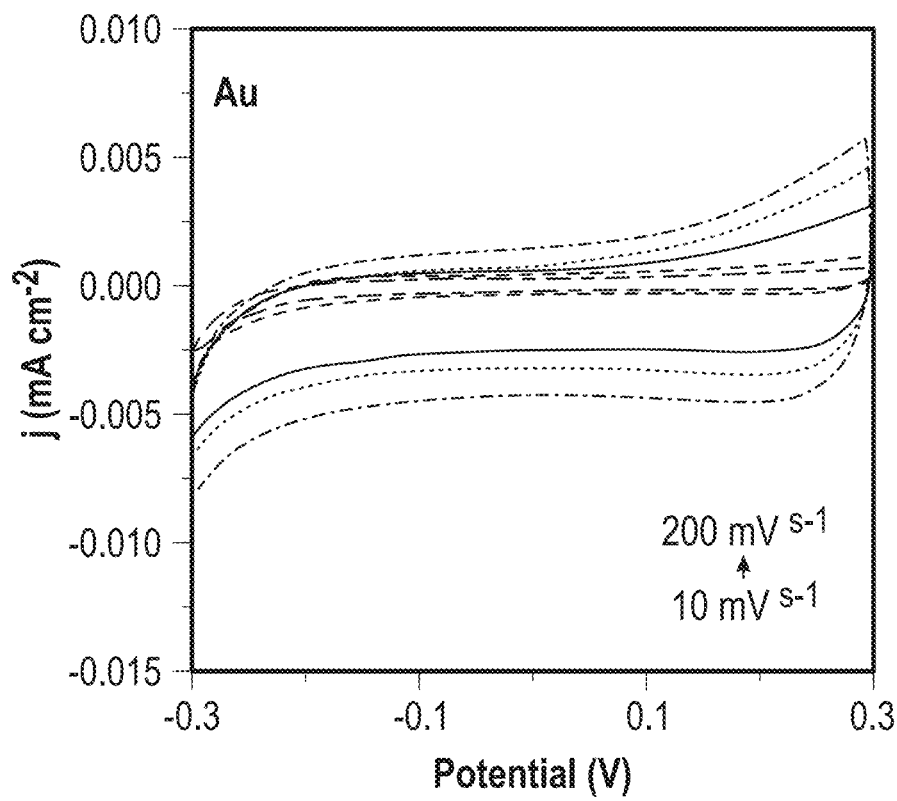
FIG. 13A illustrates, by way of example, biofuel cell optimization and characterization in accordance with various embodiments of the disclosure.
Figure 13B:
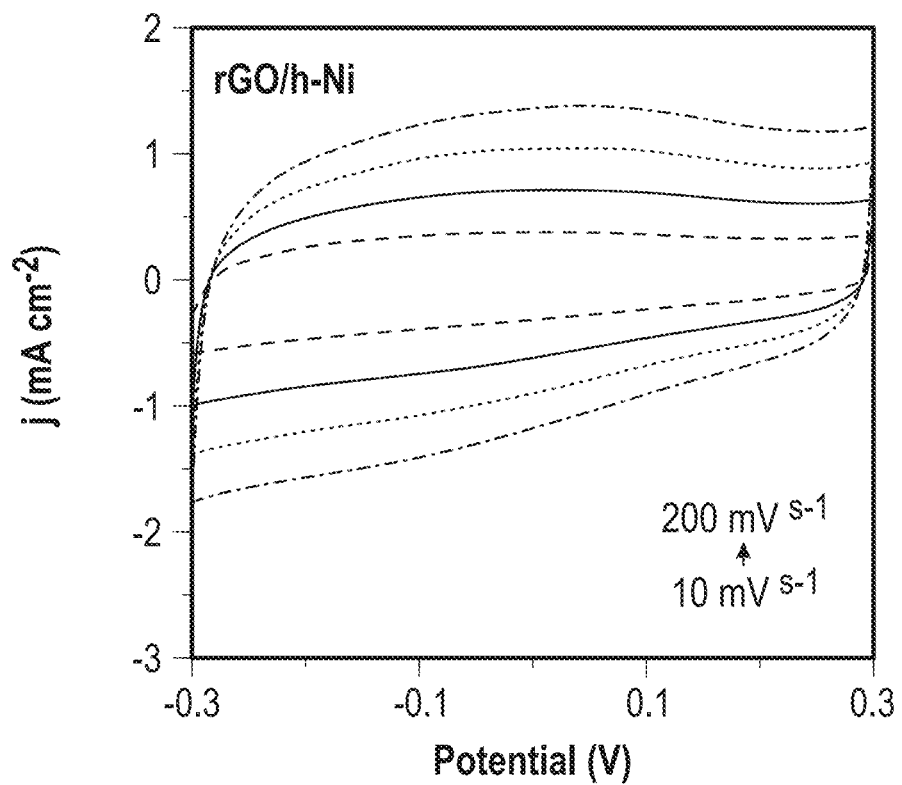
FIG. 13B illustrates, by way of example, biofuel cell optimization and characterization in accordance with various embodiments of the disclosure.
Figure 13C:
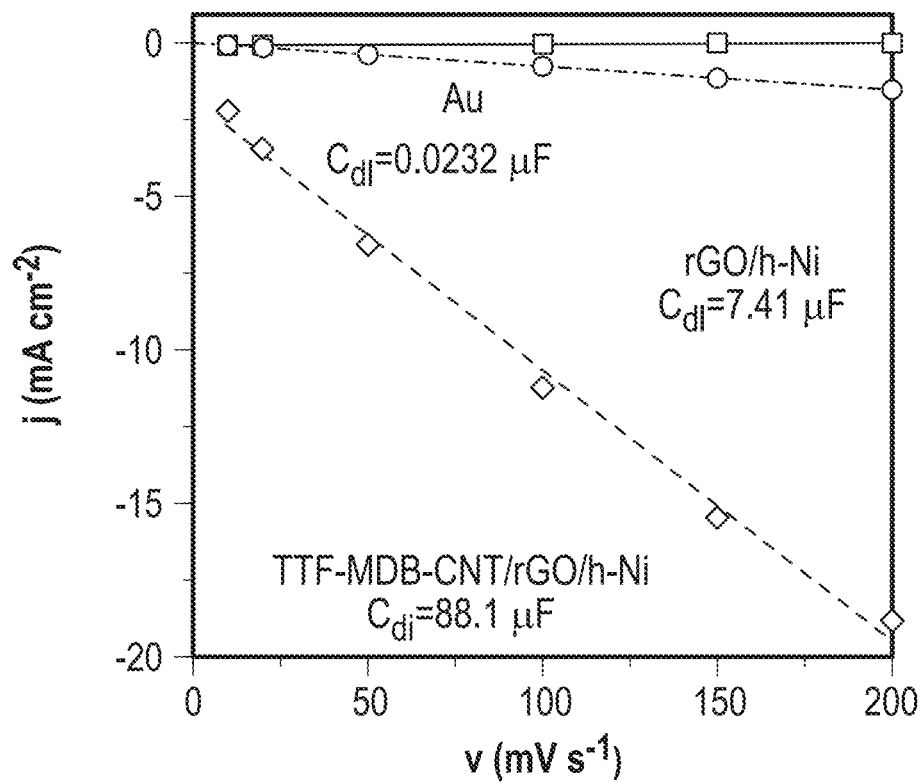
FIG. 13C illustrates, by way of example, biofuel cell optimization and characterization in accordance with various embodiments of the disclosure.

At low potential, the electron transfer rate between the generated $H_2O_2$ and the carbon-based electrode is very low ($H_2O_2$ oxidation requires a high voltage). Instead, the onset potential of the MDB and TTF are −0.2 and 0 V, respectively (as shown in FIG. 2D). Here, bioanode mixed with TTF and MDB has higher current and lower onset potential than either of single mediator.

solution and then heated to 140° C. overnight, followed by rinsing with water for several times. The resulted MDB-CNTs may then be dropcasted onto the rGO/h-Ni electrode to achieve a higher electrochemically active surface area. The MDB-CNTs/rGO/h-Ni composite may be soaked in a 20 mM TTF ethanol/acetone (9:1, v/v) solution. Then anodes may be prepared by immersing TTF-MDB-CNTs/rGO/h-Ni composite into an LOx solution (20 mg ml-1) for 2 hours and dried at 4° C. 2 µl 0.5% Nafion perfluorinated resin solution may be dropcasted on the LOx/TTF-MDBCNTs/rGO/h-Ni anodes to protect the enzymes during the operation. FIGS. 13A-13C illustrate CVs of an Au electrode (e.g., FIG. 13A) and an rGO/h-Ni electrode (e.g., FIG. 13B) at a scan rang of 10 mV s$^{-1}$-200 mV s$^{-1}$. FIG. 13C depicts current densities of Au, rGO/h-Ni, and TTF-MDB-CNT/rGO/h-Ni electrodes at −0.1 V plotted against scan rate (v).

To prepare the biofuel cell cathodes, CNT film may be laser cut into 2-mm diameter disks. The CNT pieces may then be immersed in a 2 mM MDB solution, heated to 140° C. overnight, and then rinsed with water for several times; the MDB-CNT pieces may then be immersed in a 60 mM H2PtCl6 solution with 20 mM doping metal ions like Co, Ni, Cu and Zn, and then immersed in a 0.1 M NaBH4 solution for seconds followed by several water rinsing; 2 µl 0.5% Nafion perfluorinated resin solution may then be drop casted onto the Pt or Pt alloy decorated MDB-CNT composite surfaces.

Figure 14A:
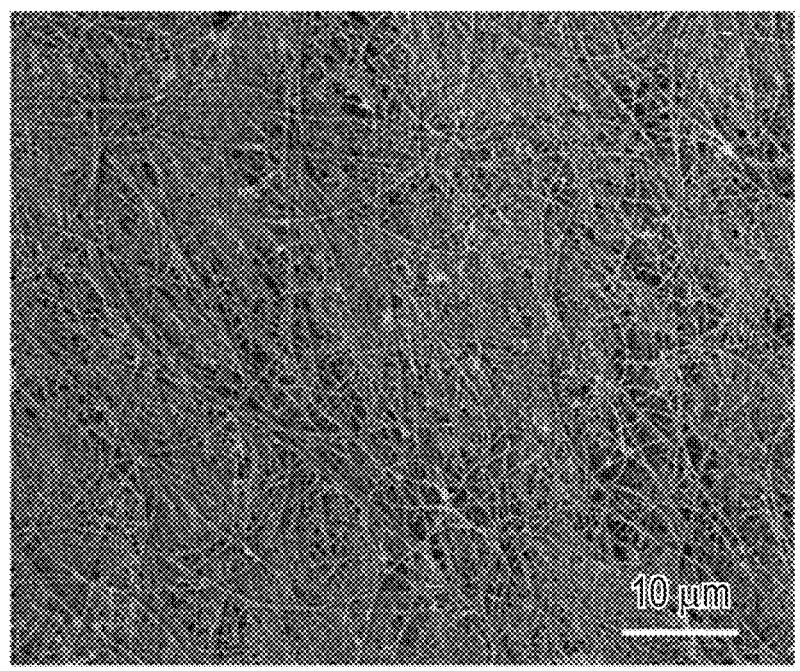
FIG. 14A illustrates, by way of example, biofuel cell optimization and characterization in accordance with various embodiments of the disclosure.
Figure 14A:
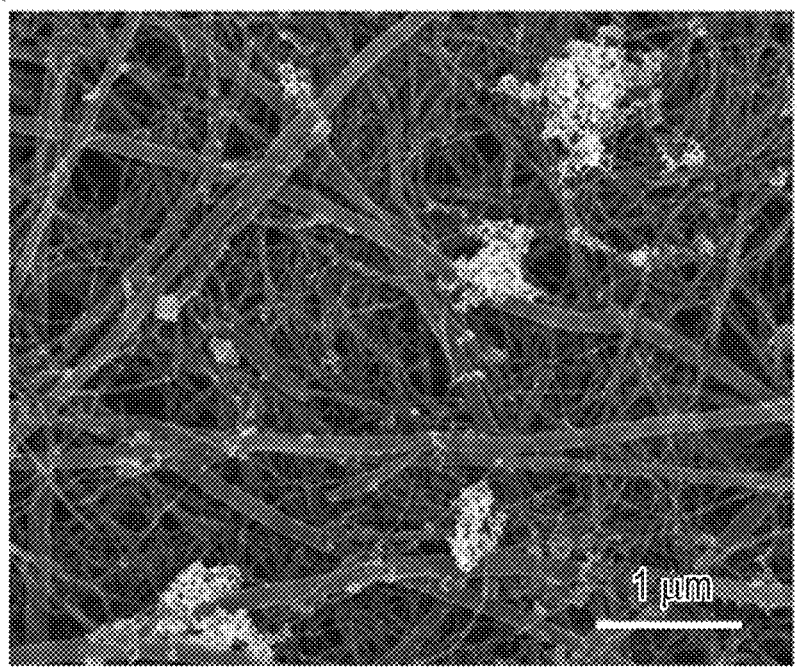
Figure 14B:
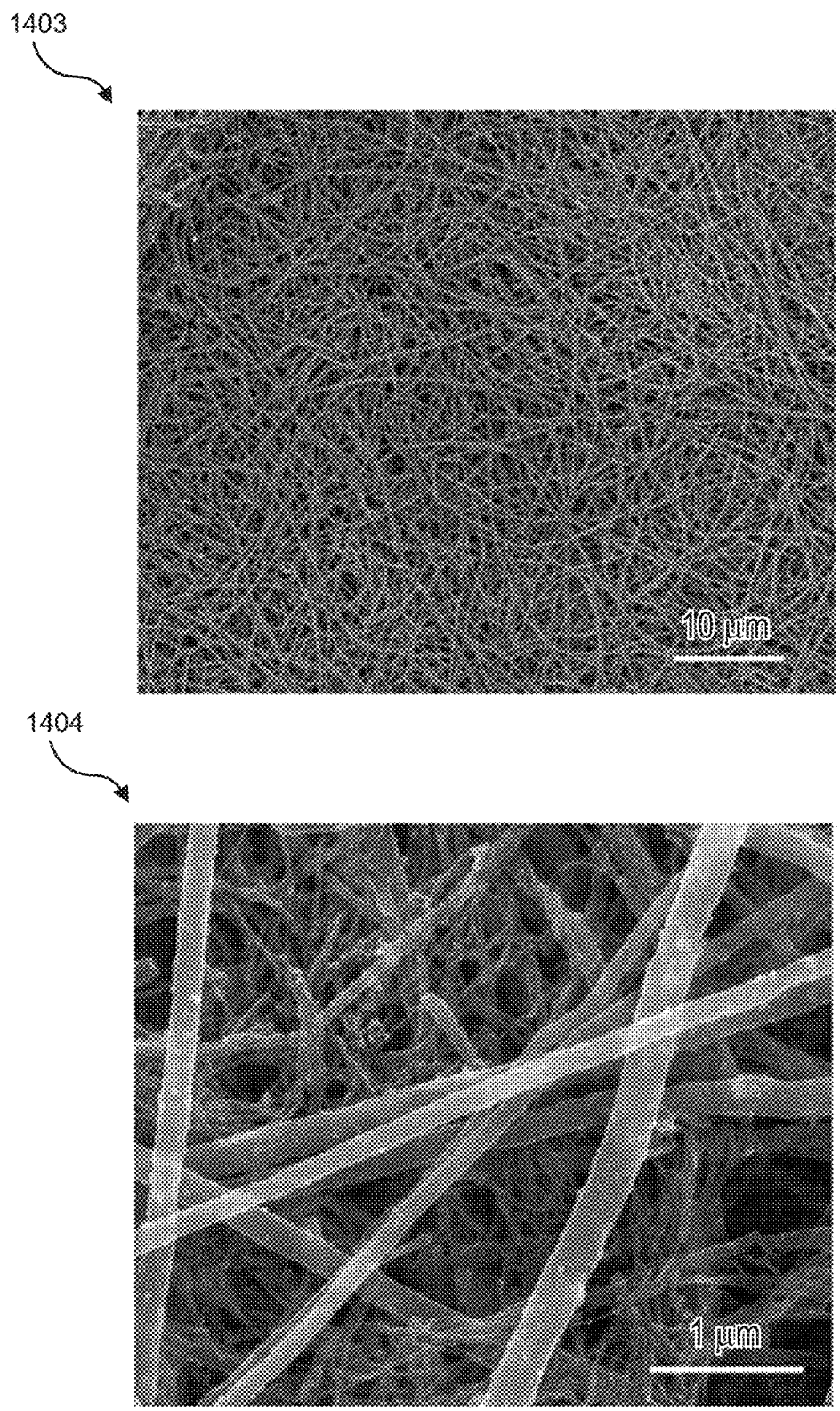
FIG. 14B illustrates, by way of example, biofuel cell optimization and characterization in accordance with various embodiments of the disclosure.
Figure 15A:
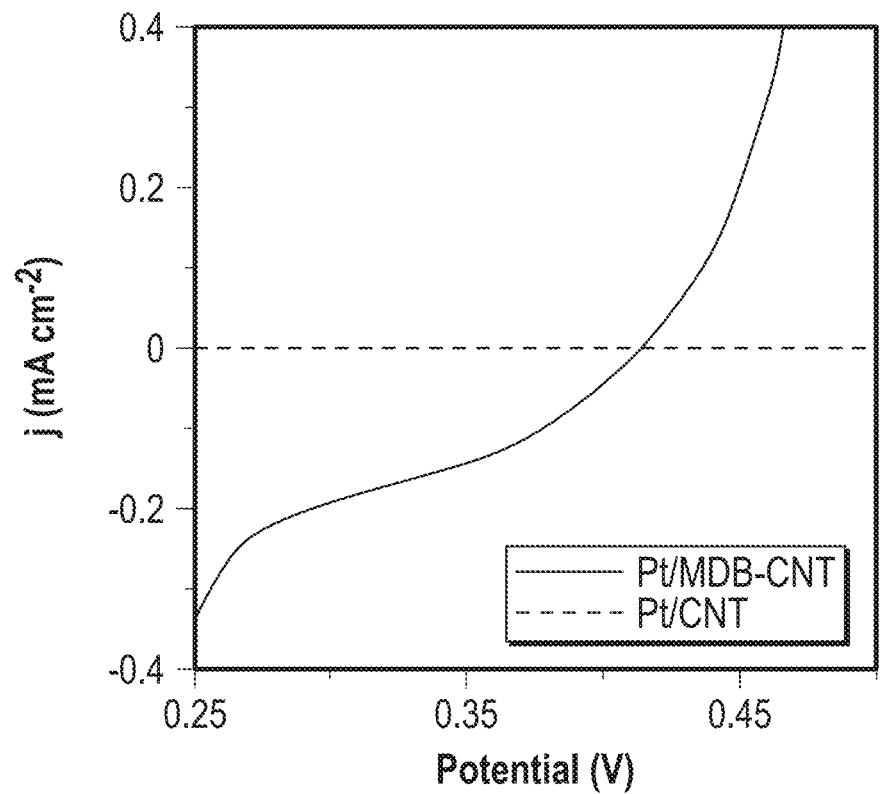
FIG. 15A illustrates, by way of example, biofuel cell optimization and characterization in accordance with various embodiments of the disclosure.
Figure 15B:
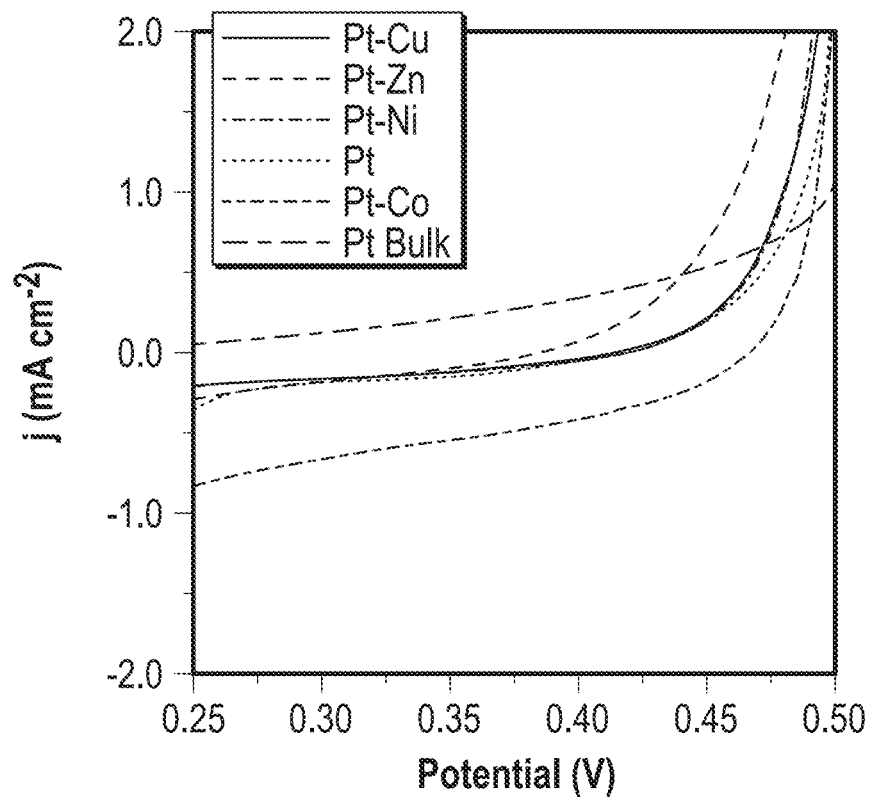
FIG. 15B illustrates, by way of example, biofuel cell optimization and characterization in accordance with various embodiments of the disclosure.

In embodiments, MDB modification may allow for uniform nanoparticle distribution with controlled sizes. FIGS. 14A-14B illustrate the role of MDB in the preparation of the Pt/CNT biofuel cathodes. For example, panels 1401-1404 depict scanning electron microscopy (SEM) images of Pt/CNT (e.g., panels 1401-1402) and Pt/MBD-CNT cathodes (e.g., panels 1403-1404) at different magnifications. FIGS. 15A-15B illustrate characterization of the Pt/CNT and Pt/MBD-CNT cathodes. FIG. 15A depicts, for example, linear sweeping voltammograms (LSVs) that suggest high performance of the Pt/MBD-CNT cathode for oxygen reduction. FIG. 15B depicts, for example, LSVs of bulk Pt, Pt/MBD-CNT, Pt-M/MBD-CNT (where M=Co, Ni, Zn, or Cu).

Figure 16A:
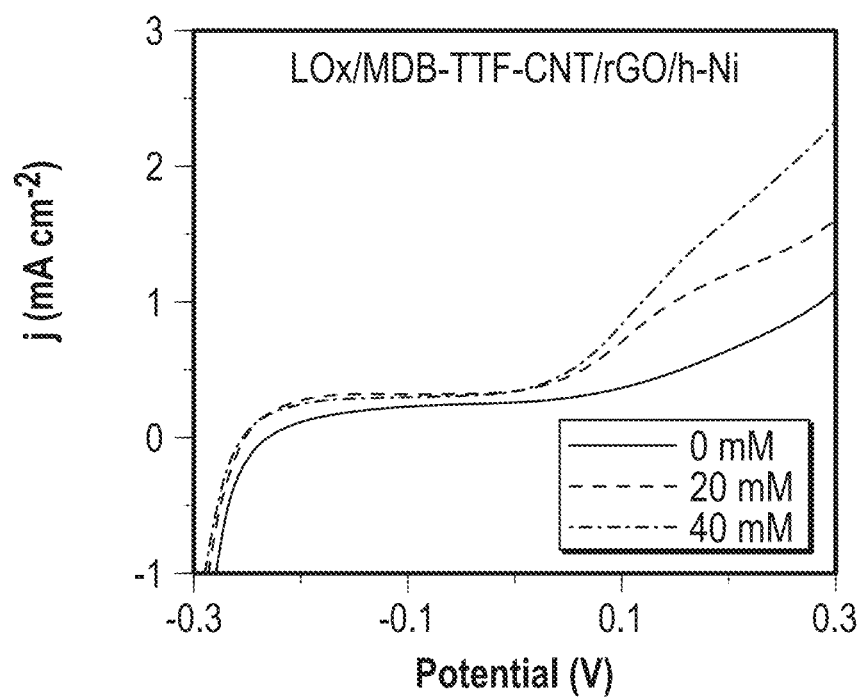
FIG. 16A illustrates, by way of example, biofuel cell optimization and characterization in accordance with various embodiments of the disclosure.
Figure 16B:
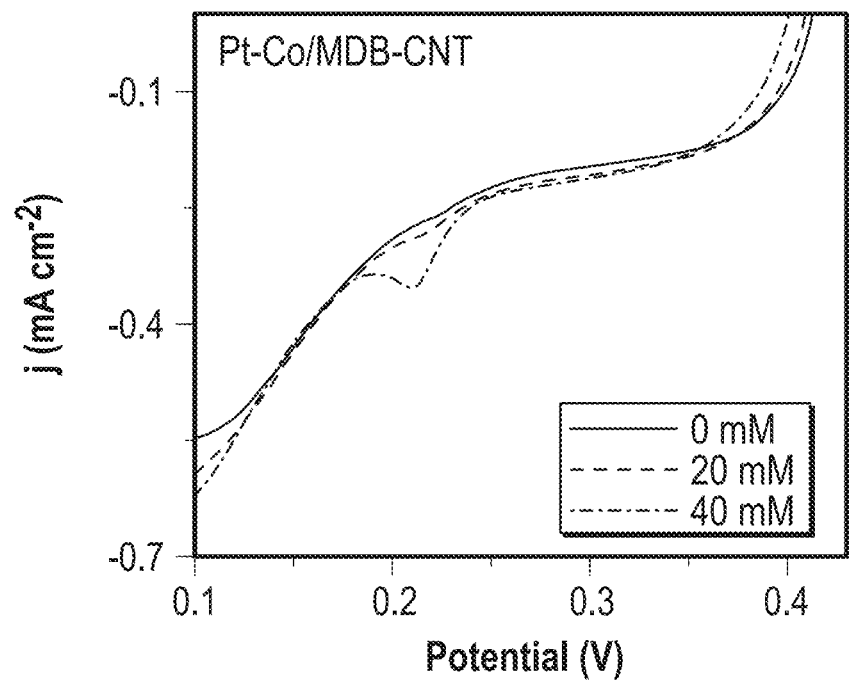
FIG. 16B illustrates, by way of example, biofuel cell optimization and characterization in accordance with various embodiments of the disclosure.
Figure 16C:
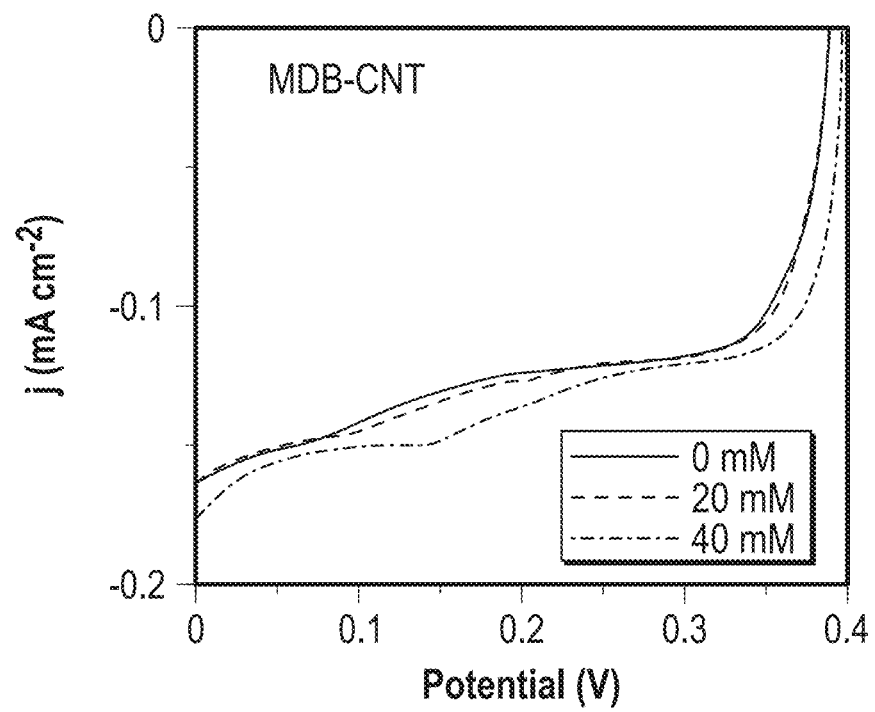
FIG. 16C illustrates, by way of example, biofuel cell optimization and characterization in accordance with various embodiments of the disclosure.
Figure 16D:
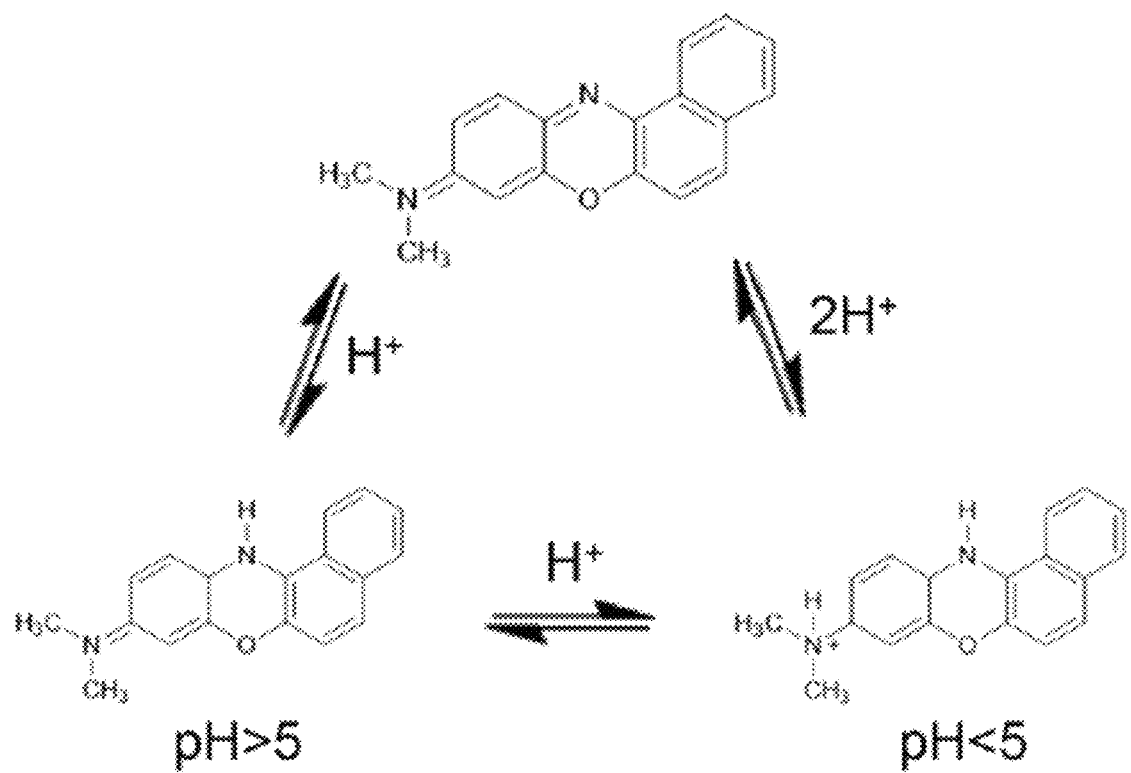
FIG. 16D illustrates, by way of example, biofuel cell optimization and characterization in accordance with various embodiments of the disclosure.

In embodiments, the assembled biofuel cell array shows excellent performance. FIGS. 16A-16D illustrate how the maximum power densities shift as the lactate concentrations change due to the varied redox reaction of MDB at different pHs. For example, FIGS. 16A-16D depict the characterizations of the anodes and cathodes in lactate solutions. LSVs of the LOx/TTF-MDB-CNT/rGO/h-Ni (e.g., FIG. 16A), Pt—Co/MDB-CNT (e.g., FIG. 16B and MDB-CNT (e.g., FIG. 16C) anodes and cathodes in 0, 20, and 40 mM lactate solutions at a scan rate of 5 mV s$^{-1}$. FIG. 16D illustrates the forms of the MDB under different pHs.

Example 2: Characterization of the Pt—Co Nanoparticle Decorated

Biofuel Cell Cathode for Enhanced Stability

Figure 17A:
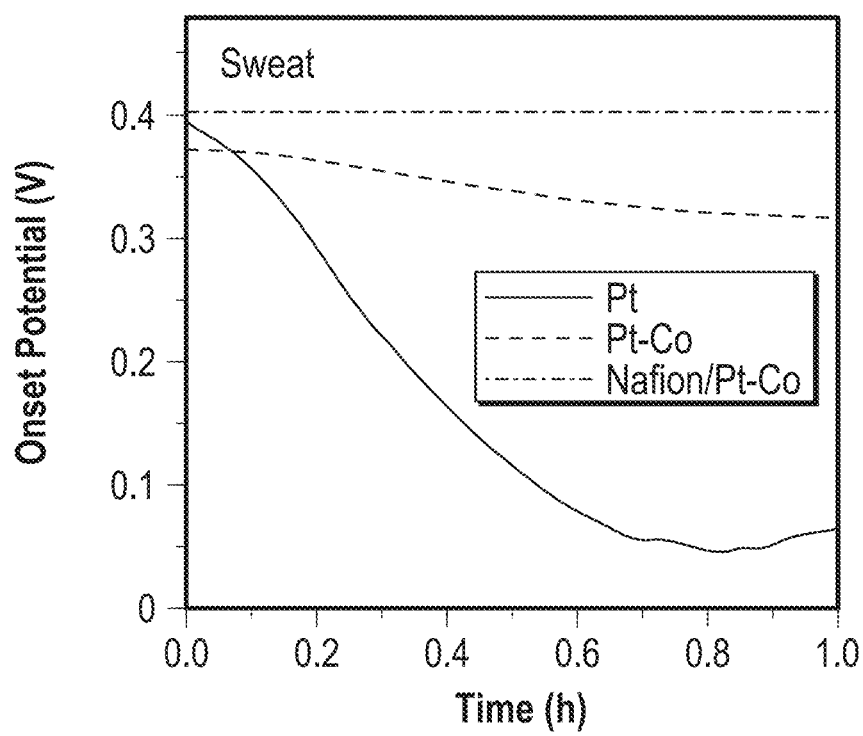
FIG. 17A illustrates, by way of example, biofuel cell optimization and characterization in accordance with various embodiments of the disclosure.
Figure 17B:
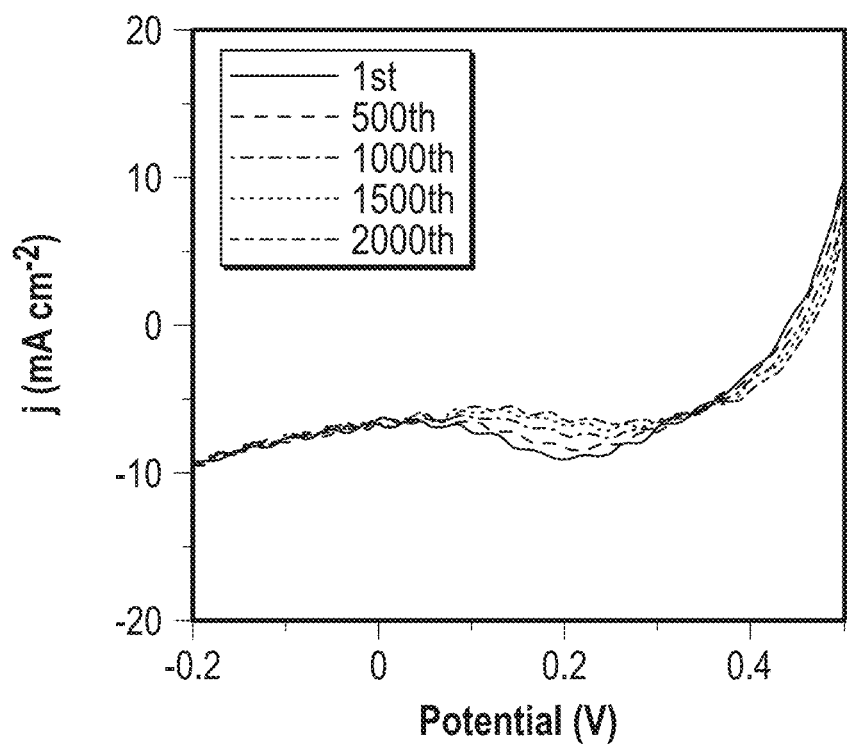
FIG. 17B illustrates, by way of example, biofuel cell optimization and characterization in accordance with various embodiments of the disclosure.
Figure 17C:
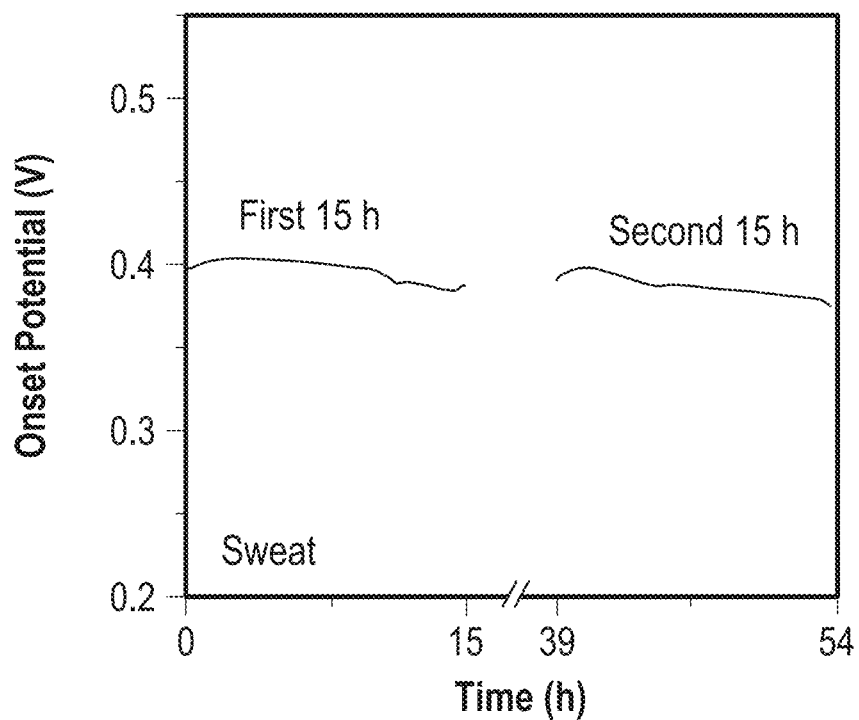
FIG. 17C illustrates, by way of example, biofuel cell optimization and characterization in accordance with various embodiments of the disclosure.

To enhance the long-term stability of the Pt particles, transition metal dopants (e.g., Co) may be introduced through electroless co-deposition. The Co dopants could enhance the cohesive energy and thus stabilize the nanoparticles, leading to significantly reduced biofouling in the biological sample and higher onset potential for oxygen reduction. FIG. 17A illustrates that in sweat samples, for example, the Pt—Co/CNT shows a relatively stable onset potential compared to that of Pt/CNT. In embodiments, to further improve the long-term stability of the cathode in a biological sample, a permselective Nafion layer may be modified onto the Pt—Co/CNT. The Nafion/Pt-Co/CNT show stable performance over 2000 cycles of CV scans (e.g., FIG. 17B) and a negligible fluctuation in the onset potential in sweat sample for over 30 hours (e.g., FIG. 17C).

Example 3: Fabrication Biosensor Platforms

Figure 18:
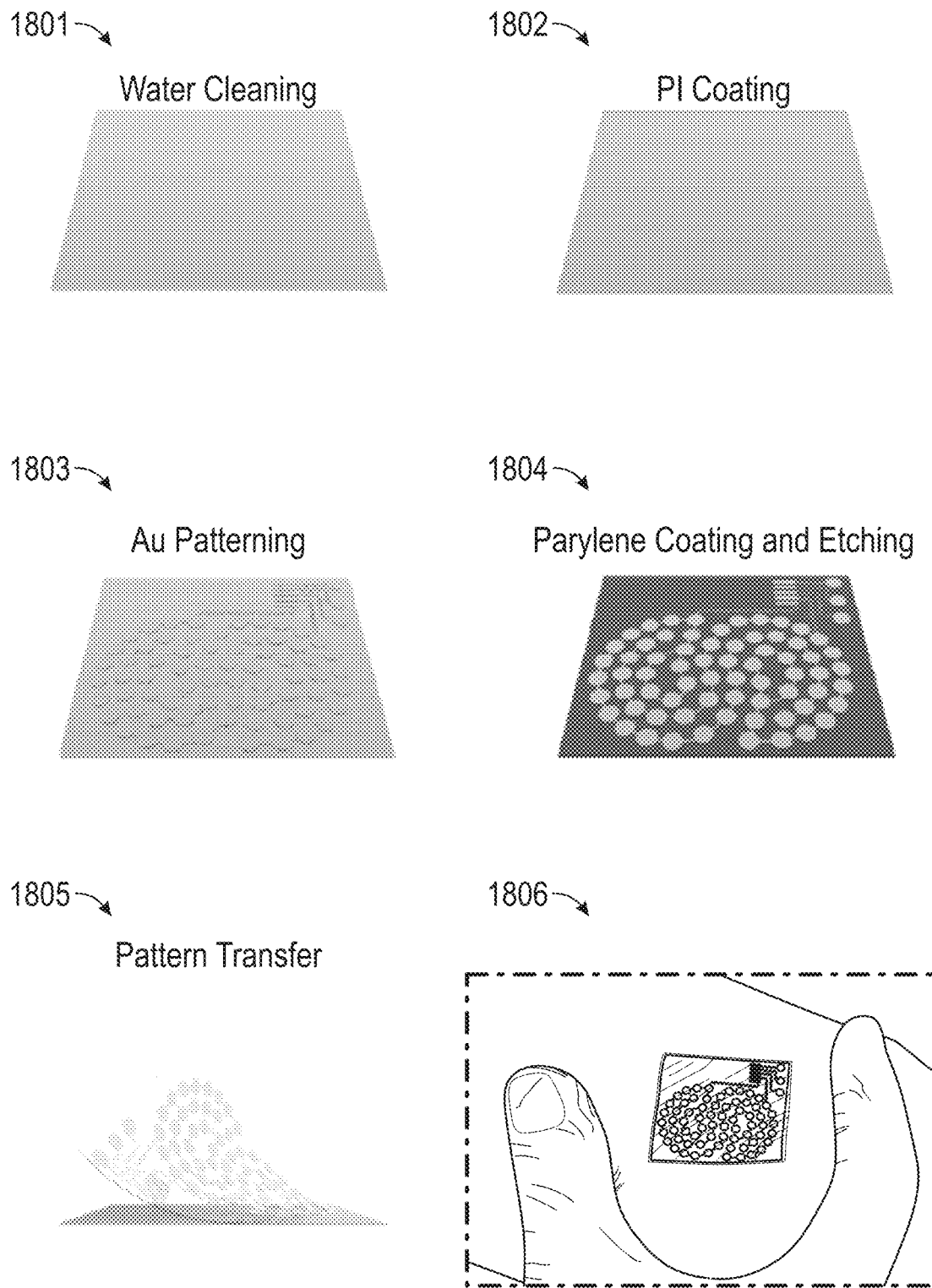
FIG. 18 illustrates, by way of example, architectures that may be used in accordance with various embodiments of the disclosure.
Figure 19:
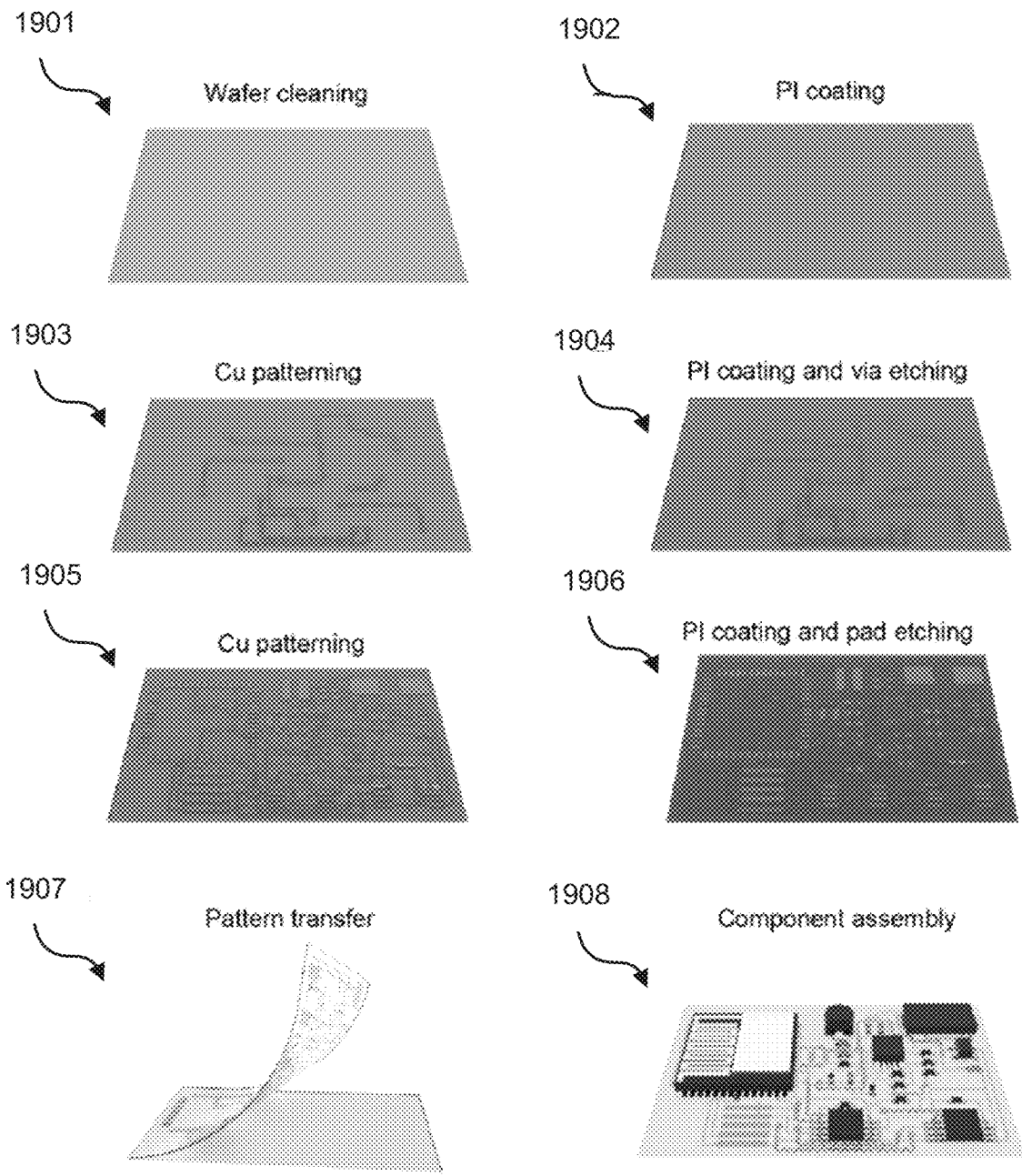
FIG. 19 illustrates, by way of example, architectures that may be used in accordance with various embodiments of the disclosure.

In embodiments, an auto-powered biosensor may be fabricated into a synthetic skin and continuously worn. FIGS. 18 and 19 illustrate by way of example, the assembly of a platform that may be used to create the various components of an auto-powered biosensor capable of forming synthetic skin, including the multimodal sensing layer and other electrical circuitry patterns, according to various embodiments herein. For example, upon cleaning, a silicon handling wafer polyimide (PI-2611) may be spin-coated on the wafer at a speed of about 2000 rpm for 30 s (e.g., frame 1802). The polyimide may then be cured at 350° C. for 1 hour at a ramping speed of about 4° C. min-1. The resulting polyimide substrate thickness is about 9 µm. Photolithography (Microchemicals GmbH, AZ 9260) may then be used to define the inner connection wires. The photoresist may then be spincoated on the wafer at a speed of 2400 rpm for 30 s and measured to be around 10 µm thick. For surface treatment, reactive ion etching (Oxford Plasmalab 100 ICP/RIE, O2 80 sccm, SF6 5 sccm, 70 W, 20 mTorr) may be used for 2 minutes to enhance surface adhesion of polyimide layers. E-beam evaporation of Cu or Au (1.5 µm, at a speed of 2.5 A s-1) may be deposited on the polyimide, followed by lift-off in acetone for minutes. An insulating layer of polyimide (PI-2610) may then be spin-coated on the surface with a speed of 5000 rpm for 30 s, and then may be cured at 350° C. for 30 minutes with a ramping speed of 4° C. min-1. The resulting intermediate polyimide layer thickness is about 1 µm. Another photolithography step was used to define via connections between Cu layers. The wafer may then be selectively dry-etched using inductively coupled plasma (Oxford Plasmalab 100 ICP/RIE, O2 50 sccm, 150 W, 80 mTorr, 9 minutes) to form via pattern. Photolithography may then be used to define outer connection wires. The wafer may then be surface treated with reactive ion etching using the same recipe described above prior to metal evaporation. E-beam evaporation of Cu or Au (2.5 µm, at a speed of 2.5 A s-1) may then be performed and followed by lift-off in acetone. Another encapsulation layer of polyimide (PI-2610) (1 µm thick) may then be spin-coated and followed by fully curing. Photolithography may then be performed to define openings of sensors and BFC patterns and then dry etching was performed using inductively coupled plasma (Oxford Plasmalab 100 ICP/RIE, O2 50 sccm, 150 W, 80 mTorr, 9 minutes).

After wiring system patterning, polyimide may then be spin-coated on the silicon handling wafer with a thickness of 9 µm. Photolithography (Microchemicals GmbH, AZ 9260) may be used to define the shapes of biofuel cells and sensor arrays. The polyimide may then be surface treated with reactive-ion etching to enhance surface adhesion (Oxford Plasmalab 100 ICP/RIE, O2 80 sccm, SF6 5 sccm, 70 W, 20 mTorr). E-beam evaporation of Cr/Au (20/100 nm, at a speed of 0.2 A/s and 0.5 A/s respectively) may then be performed, followed by lift-off in acetone. A thin layer of parylene (ParaTech LabTop 3000 Parylene coater) may then be deposited (1 µm) and followed by photolithography and reactive ion etching (Oxford Plasmalab 100 ICP/RIE, O2 30 sccm, 100 W, 50 mTorr, 3 minutes) to expose openings for further treatments.

Frames 1801-1806 of FIG. 18 depict, for example, the steps of wafer cleaning (e.g., frame 1801); spin coating of PI on the wafer (e.g., frame 1802); electrode patterning using photolithography, electron beam evaporation and lift-off in acetone (e.g., frame 1803); parylene insulting layer patterning (e.g., frame 1804); and biofuel cell patch release from the wafer (e.g., frame 1805). Frame 1806 depicts, for example, a biofuel cell patch on human skin.

Frames 1901-1908 of FIG. 19, depict, for example, the steps of wafer cleaning (e.g., frame 1901); spin-coating of PI (9 µm) on the handling wafer (e.g., frame 1902); Cu patterning (1.5 µm) using photolithography, electron-beam evaporation, and lift-off (e.g., frame 1903); insulating PI layer (1 µm) coating and via etching (e.g., frame 1904); Cu patterning using photolithography, electron-beam evaporation (2.5 µm) and lift-off in acetone (e.g., frame 1905); insulating PI layer (1 µm) coating and selective etching of the connecting pads (e.g., frame 1906); patch release from the wafer (e.g., frame 1907); and assembling of the electronic components on the soft electronic patch (e.g., frame 1908).

Example 4: System Level Interrogation of a Biosensor

Figure 20:
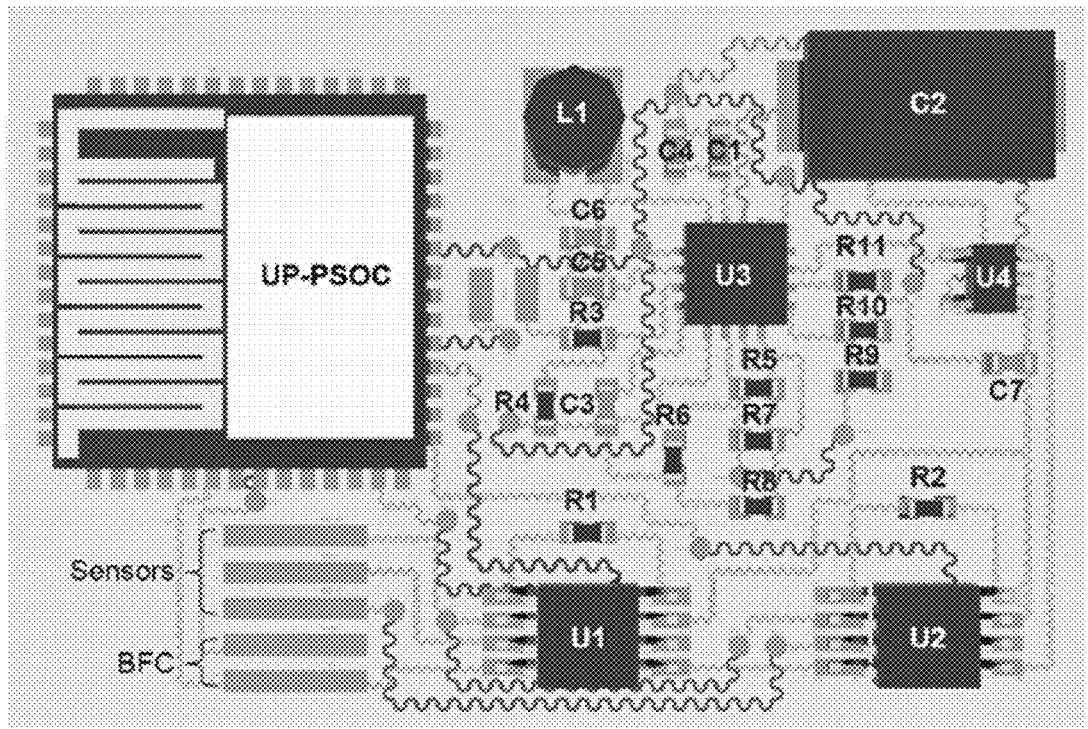
FIG. 20 illustrates, by way of example, circuitry that may be used in accordance with various embodiments of the disclosure.

In certain embodiments, a fully integrated biosensor may include a multimodal sensing layer that includes a biofuel cell array and a sensing array comprising at least one electrode, a boost converter, instrumentation amplifiers, and a programmable system on chip (PSoC) module (integrated with a Bluetooth® Low Energy (BLE) module, a microcontroller, and a temperature sensor). FIG. 20 illustrates, for example, an electronic system that may be employed by a biosensor according to the various implementations disclosed herein. In embodiments, the DC-DC boost converter amplifies the signal potential with a small power loss (~20%) (e.g., FIG. 9, 902). The output signal (3.3 V) may continuously charge a capacitor (660 µF) that may temporarily store the energy and powers biosensors and other electronic components. The BLE module may run in bursts of activity, periodically waking up from deep sleep to acquire measurements with the embedded successive-approximation analog-to-digital converter then wirelessly broadcasting the data to the user interfaces. In embodiments, BLE advertising may be selected owing to the small size of the data packets and the low power consumption. For illustrative purposes, a key to the components of FIG. 20 is provided in Table 3.

TABLE 3

| Components | Description | Value and Series No. |
|---|---|---|
| UP-PSOC | EZ-BLE Creator Module | CYBLE-214009-00 |
| U1 | Instrumentation Amplifier | INA 333 |
| U2 | Instrumentation Amplifier | INA 333 |
| U3 | Boost Converter | BQ25504 |
| U4 | Analogue Switch | MAX4715EXK + T |
| C1 | 0402 Capacitor | 4.7 µF |
| C2 | Tantalum Capacitors | 680 µF |
| C3 | 0402 Capacitor | 0.01 µF |
| C4 | 0402 Capacitor | 0.1 µF |
| C5 | 0402 Capacitor | 4.7 µF |
| C6 | 0402 Capacitor | 0.1 µF |
| C7 | 0402 Capacitor | 0.1 µF |
| R1 | 0402 Resistor | ∞ |

TABLE 3-continued

| Components | Description | Value and Series No. |
|---|---|---|
| R2 | 0402 Resistor | ∞ |
| R3 | 0402 Resistor | 4.99 MΩ |
| R4 | 0402 Resistor | 15 MΩ |
| R5 | 0402 Resistor | 4.32 MΩ |
| R6 | 0402 Resistor | 5.6 MΩ |
| R7 | 0402 Resistor | 3.65 MΩ |
| R8 | 0402 Resistor | 6.2 MΩ |
| R9 | 0402 Resistor | 2.37 MΩ |
| R10 | 0402 Resistor | 3.65 MΩ |
| R11 | 0402 Resistor | 3.92 MΩ |

Figure 21A:
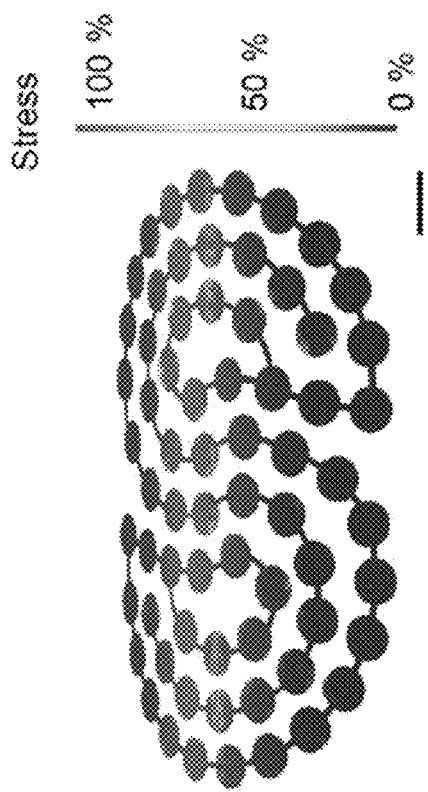
FIG. 21A illustrates, way of example, characterization of a multimodal sensing layer in accordance with various embodiments of the disclosure.
Figure 21A:
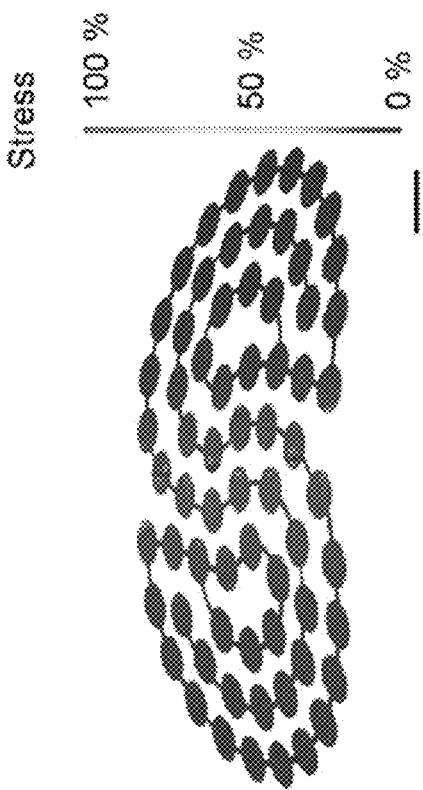
Figure 21B:
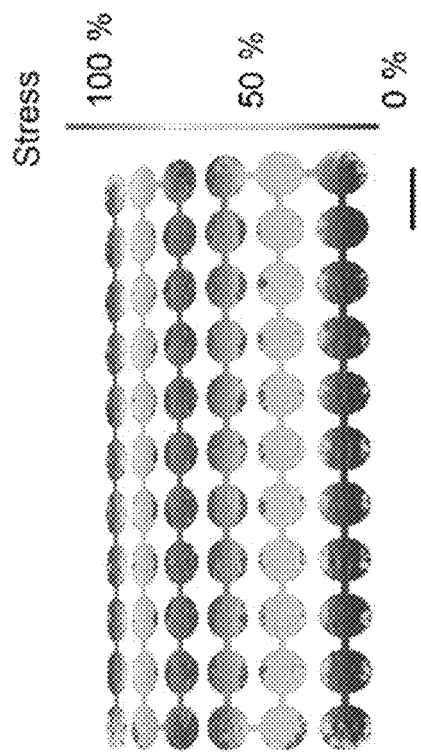
FIG. 21B illustrates, way of example, characterization of a multimodal sensing layer in accordance with various embodiments of the disclosure.
Figure 21B:
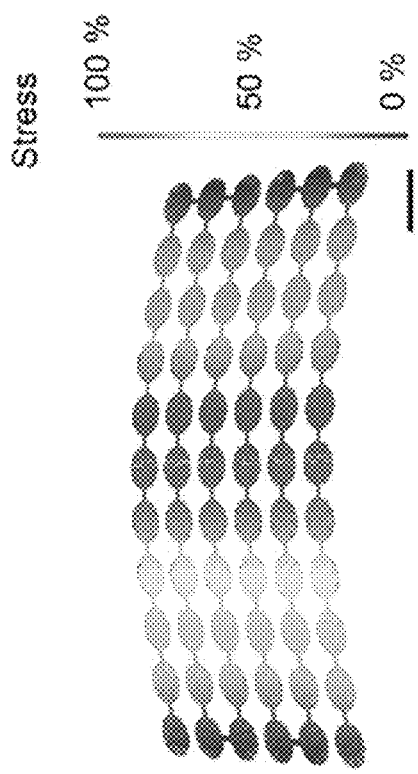

In embodiments, components of the biosensor may be patterned on an ultra-soft PI substrate through standard/nanofabrication to comply with the wearer's skin elasticity. A serpentine structure may be used to minimize the overall size of the multimodal sensing layer, reduce strain, and achieve uniform strain distribution during mechanical deformation. FIGS. 21A-21B illustrate a mechanical deformation study of the biofuel cell array of the multimodal sensing layer. For example, FIG. 21A depicts a numerical simulation of stress distributions of the biofuel cell array in a serpentine configuration vs. the straight-line configuration of FIG. 21B.

Example 5: Power Consumption

Figure 22:
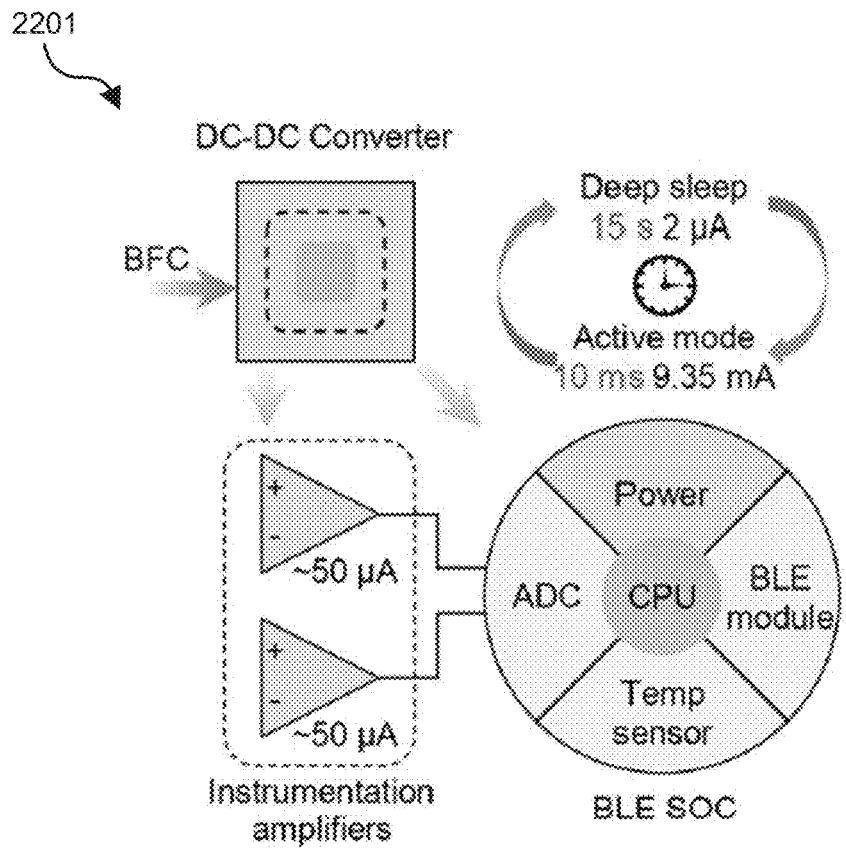
FIG. 22 illustrates, by way of example, validation of an auto-powered biosensor in accordance with various embodiments of the disclosure.
Figure 22:
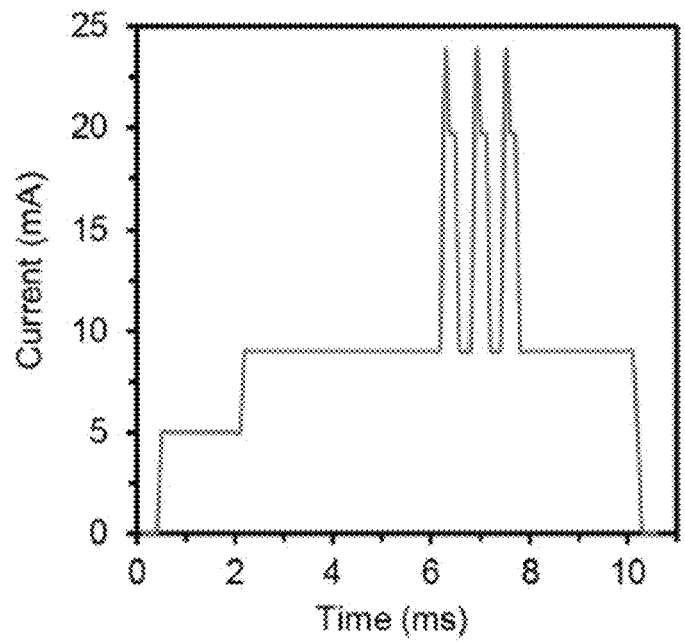
Figure 23A:
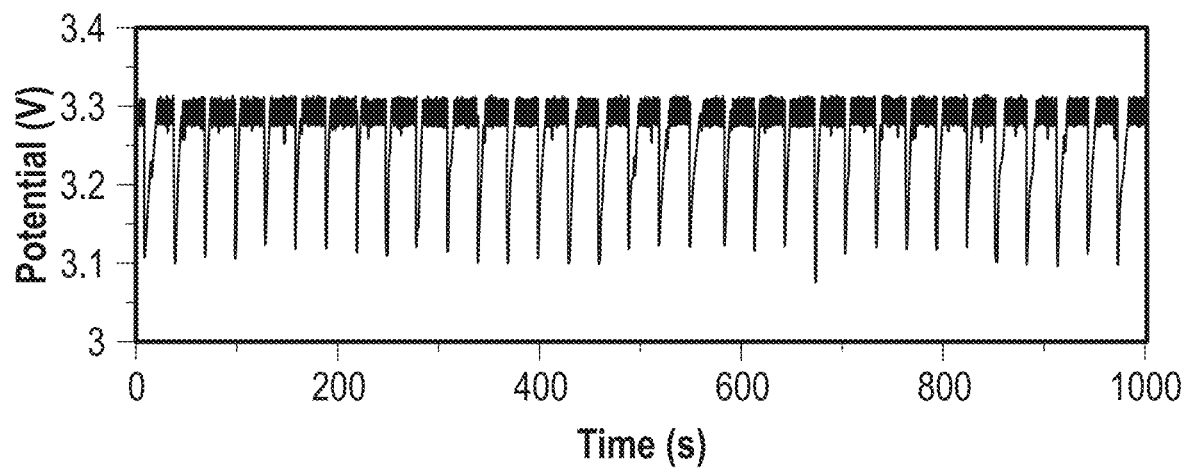
FIG. 23A illustrates, by way of example, validation of an auto-powered biosensor in accordance with various embodiments of the disclosure.
Figure 23B:
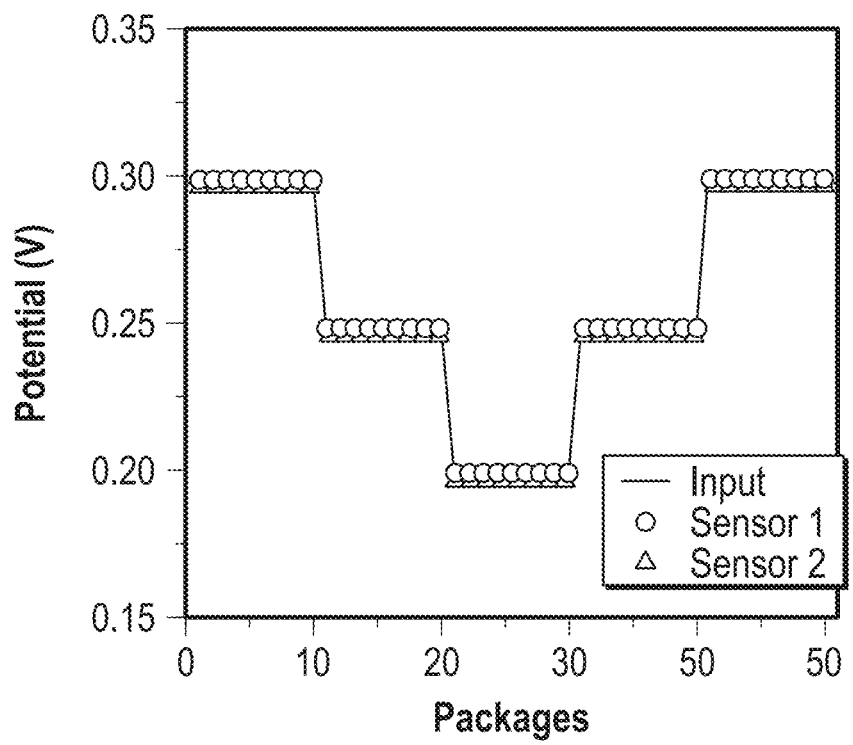
FIG. 23B illustrates, by way of example, validation of an auto-powered biosensor in accordance with various embodiments of the disclosure.
Figure 23C:
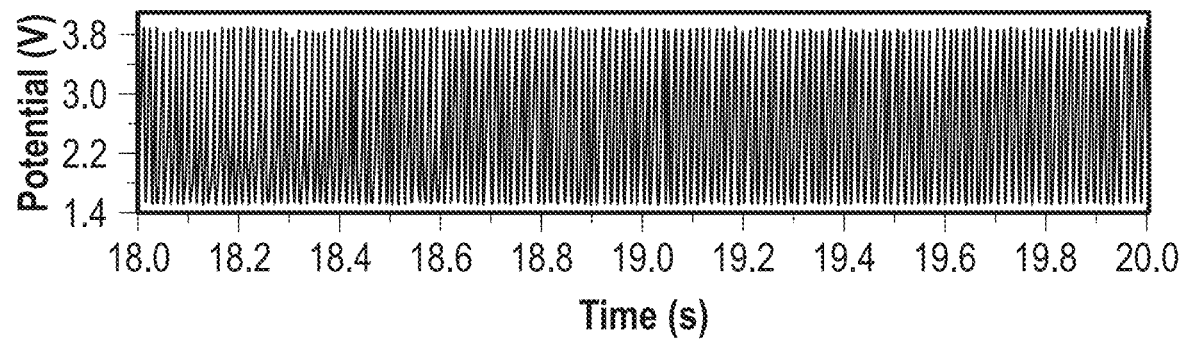
FIG. 23C illustrates, by way of example, validation of an auto-powered biosensor in accordance with various embodiments of the disclosure.
Figure 23D:
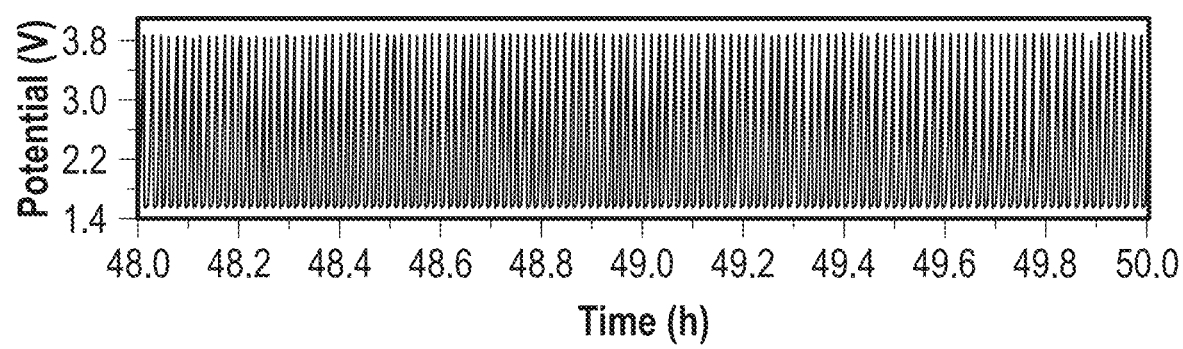
FIG. 23D illustrates, by way of example, validation of an auto-powered biosensor in accordance with various embodiments of the disclosure.
Figure 24A:
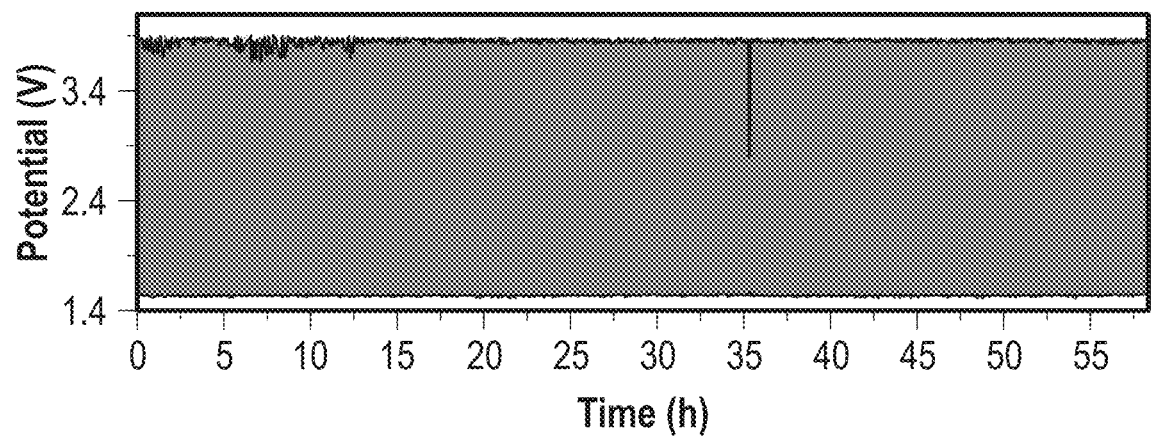
FIG. 24A illustrates, by way of example, validation of an auto-powered biosensor in accordance with various embodiments of the disclosure.
Figure 24B:
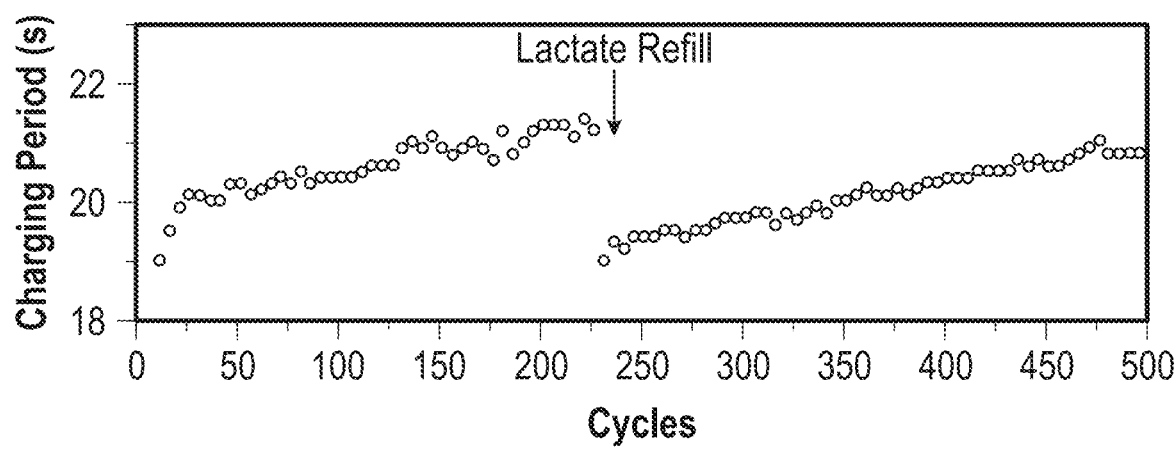
FIG. 24B illustrates, by way of example, validation of an auto-powered biosensor in accordance with various embodiments of the disclosure.
Figure 25A:
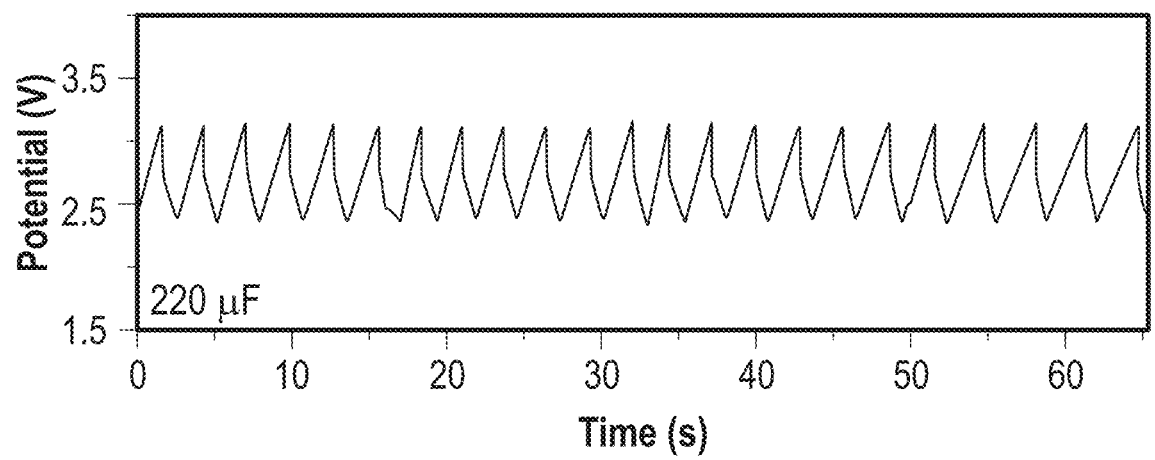
FIG. 25A illustrates, by way of example, validation of an auto-powered biosensor in accordance with various embodiments of the disclosure.
Figure 25B:
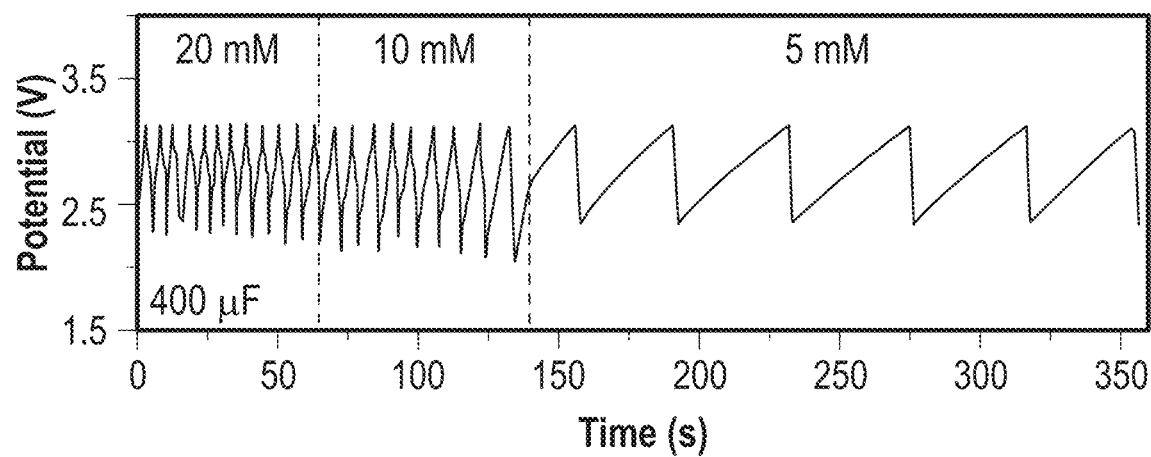
FIG. 25B illustrates, by way of example, validation of an auto-powered biosensor in accordance with various embodiments of the disclosure.

In embodiments, during deep sleep mode, a biosensor that may be prepared according to the various embodiments disclosed herein may draw a total current of about 100 µA at 3.3 V, primarily from two instrumental amplifiers. FIG. 22 illustrates, by way of example, power consumption panel 2201, wherein energy harvested from the biofuel cell (here, "BFC") is supplied to the DC-DC converter. A biosensor may be programmed to wake up periodically from deep sleep for about 10 minutes to acquire and send data to a mobile device and use an average power consumption of about 9.35 mA. For example, power consumption panel 2202 illustrates the power consumption of a PSoC module during a wakeup operation. In embodiments, the capacitor may discharge when the biosensor wakes up and may be recharged within a few seconds by the biofuel cells. In 20 mM lactate, dynamic changes in the potential of the capacitor on a biosensor are demonstrated, for example, in FIG. 23A. Wirelessly received BLE data in the user interface shows good agreement with the dual-channel sensor inputs (e.g., FIG. 23B). Excellent long-term stability of the biofuel cell-based electrical charging/discharging process is demonstrated by the continuous charging activity for about 60 hours, as shown in FIGS. 23C and 23D. A capacitor may be charged from 1.5 to 3.8 V continuously and repeatedly, and the charging periods could remain stable when fresh lactate fuel is supplied. FIGS. 24A and 24B illustrate the long-term stability of the biofuel cells to charge a capacitor. For example, FIG. 24A depicts the performance of the biofuel cells to charge a capacitor (220 µF) for nearly 60 hours in a 20 mM lactate solution. Figure FIG. 24B depicts, for example, the period to charge the capacitor (220 µF) from 1.8 to 3.8 V. These results demonstrate that by using a smaller capacitor (220 or 400 µF), a biosensor may be continuously powered in lactate solutions (between about 5 to about 20 mM) without the need of deep sleep mode. For example, FIGS. 25A and 25B illustrate continuous operation of a biosensor with small capacitors in 5 to 20 mM lactate. FIG. 25A depicts, for example, real-time capacitor potential of a biosensor during continuous operation in 20 mM lactate (capacitor at 220 µF). FIG. 25B depicts, for example, real-time capacitor potential of a biosensor measured during continuous operation in 20, 10, and 5 mM lactate (capacitor at 400 μF).

Example 6: Packaging of a Biosensor

In embodiments, packaging and assembly of a biosensor according to various embodiments disclosed herein may include setting the electrical circuitry pattern on polydimethylsiloxane (PDMS) and connect it with the multimodal sensing layer pattern (including the biofuel cell/sensor array) by a conductive silver paint. The PDMS may then be coated on the multimodal sensing layer and electronic circuitry patterns. In embodiments, after the electrodes are modified on the multimodal sensing layer, it may be combined with the laser-cut microfluidics layer, which may be assembled with two medical tape layers and a single PDMS layer in the middle.

In embodiments, the core of the biosensor sampling and data processing transmission system is the CYBLE-214009-00 BLE module. The microcontroller provided onboard BLE capability and 12-bit ADC resolution, as well as a minimal power consumption of 1.3 μA in deep sleep. The open-circuit potential (OCP) of the biofuel cells could hardly reach 1 V, which is significantly lower than the regular electronics needed. Thus, in embodiments, a soft integrated electronic patch, containing energy boost converter for increasing the applied voltage, multiplexed sensing channels and Bluetooth® broadcast was combined with the wearable biofuel cells. In embodiments, the a boost converter (e.g., BQ25504 Boost Converter TI) forms the core of the circuitry used to obtain energy from the biofuel cells.

Example 7: Fabrication of Various Sensors

In embodiments, a shared reference electrode for potentiometric sensing may include the following steps: Ag may be electrodeposited on the Au electrodes with a potentiostat method (−0.25 V for 600 s) in a solution containing 0.25 M AgNO3, 0.75 M Na2S2O3 and 0.43 M NaHSO3; the Ag/AgCl electrode may be obtained by dropping the 0.1 M FeCl3 solution on top of Ag surface for 60 s; then a PVB reference cocktail may be prepared by dissolving 79.1 mg PVB, 50 mg NaCl, 1 mg F127 and 0.2 mg MWCNT in 1 ml methanol; 6.6 μl reference cocktail may then be modified on the Ag/AgCl electrode and left overnight.

In embodiments, an $NH_4^+$ selective electrode may be prepared according to the following steps: 100 mg of the $NH_4^+$ selective membrane cocktail consisting of 1% $NH_4^+$ ionophore (nonactin), 33% PVC and 66% DOS (w/w) may be dissolved in 660 μl tetrahydrofuran. The membrane cocktail may then be stored at 4° C. A constant current of 0.2 $mA^{cm-2}$ may then be applied to electrodeposit the poly(3,4-ethylenedioxythiophene) polystyrene sulfonate (PEDOT:PSS) membrane on the Au electrode in the solution containing 0.01 M 3,4-Ethylenedioxythiophene (EDOT) and 0.1 M NaPSS to minimize the potential drift of the ISEs. 6.6μl of the cocktail solution may then be dropcasted over the PEDOT layer to create an $NH_4^+$ selective membrane. The modified electrodes may then be left to dry overnight. To prepare a urea sensing electrode, 3.7 μl of urease solution (10 mg ml-1) may be drop-casted onto the $NH_4^+$ ISE four times, and then 3.3 μl 0.5% Nafion perfluorinated resin solution may be dropped over the sensor area. The modified sensors may then be dried at 4° C. overnight.

In embodiments, a glucose selective electrode may be prepared according to the following steps: differential pulse amperometry (100 cycles in total) may be used to electrodeposit the Pt on the Au electrode. −0.4 V potential may then be applied for 1 s and 1.0 V may be used as the cleaning voltage for 0.5 s. 1.1μl 1% Nafion (prepared by dilution of Nafion perfluorinated resin solution in water) and then may be dropped on the Pt surface; 2 μl CS-GOx mixture (3:1, v/v) may be modified on the electrode. In embodiments, the potentiometric glucose sensors may then be dried at 4° C. overnight; then another 1.1 μl 1% Nafion (1%) may be dropped, covering the enzymes to form the sandwich structure. For the pH sensor, the polyaniline (PANT) may be electropolymerized on the Au electrodes in a solution containing 0.1 M aniline and 0.1 HCl using cyclic voltammetry from −0.2 to 1 V for 50 cycles at a scan rate of 50 $mV^{s-1}$.

In embodiments, for the in-vitro sensor characterizations, analyte solutions may be prepared in McIlvaine buffer solutions (pH 6.0 for urea, glucose and $NH_4^+$). The $NH_4^+$ ion-selective sensors and urea sensors may be placed in a solution containing 0.1 M NH4Cl and 20 mM urea for 1 hour before measurements. The glucose sensors and pH sensors may be placed in a solution containing 100 μM glucose and $H_2O$ for 1 hour, separately. This conditioning process may greatly help to minimize the potential drift.

In embodiments, a strain sensor (e.g., CNT-PDMS elastomer) may be prepared according to the following steps: 7% CNTs (w/w) may be added to SYLGARD™ a 184 Silicone Elastomer Base and toluene mixture (1:4 v/v) at room temperature. The mixture may then be poured into a culture dish. Following toluene evaporated, uncured CNT-PDMS may then be mixed with a curing agent (10:1) and poured onto the mask made by tape and then scraped flat with a glass slide. Following mask removal, the CNT-PDMS may then be baked at 80° C. for 1 hour. Uncured Ecoflex may then be spin-coated on it and cured at 80° C. for 1 hour. The silver paste may then be utilized to link the pad on the patterned CNTPDMS with thin wires. Another layer of Ecoflex may then be spin-coated for encapsulation and protection. The strain sensors may then be connected to a biosensor through external wires.

Example 8: Characterization of the Various Sensors

The systems and methods disclosed herein hold great promise for sensing different target molecules in a biological sample, including for example, the different analytes in sweat. Indeed, several target molecules found in human sweat, including for example, urea, glucose, pH and $NH_4^+$ contain meaningful information about an individual's physiological status. The multimodal sensing layer disclosed herein includes at least one electrode that may be used to detect a target molecule. In various embodiments, more than one electrode may be configured into an array designed to detect more than one target molecules (e.g., a sensing array).

Figure 26A:
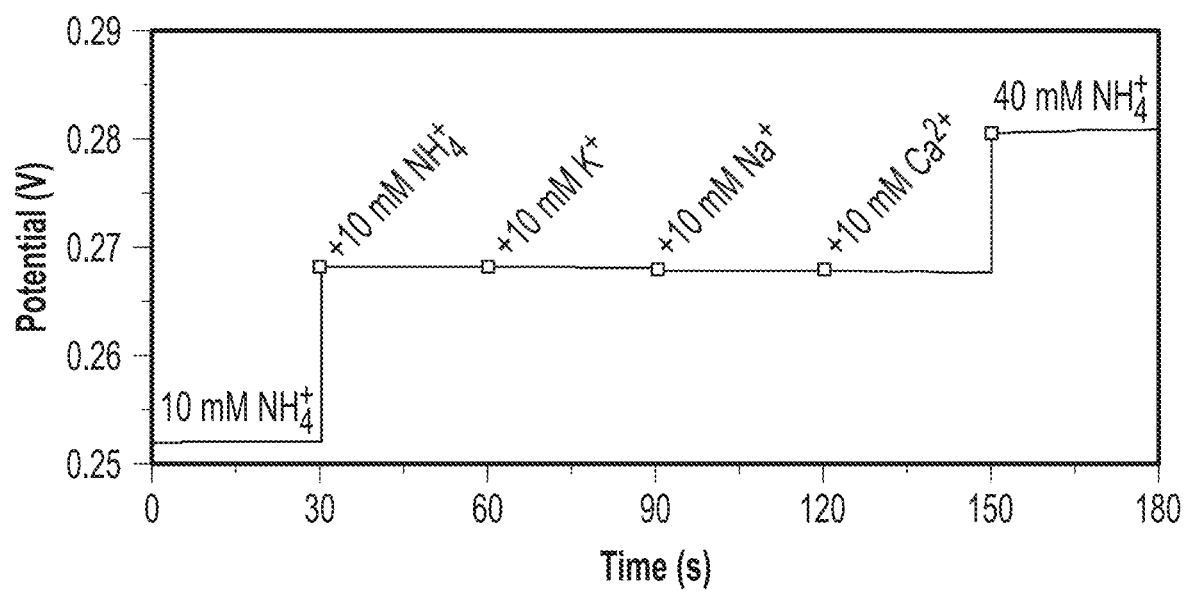
FIG. 26A illustrates, by way of example, sensor selectivity in accordance with various embodiments of the disclosure.
Figure 26B:
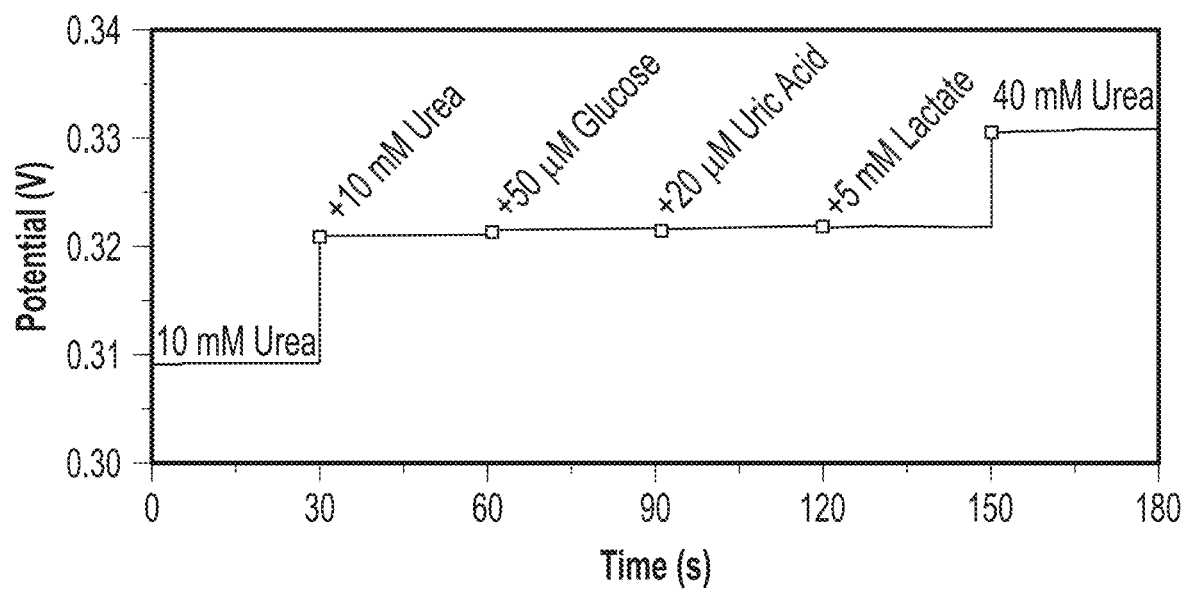
FIG. 26B illustrates, by way of example, sensor selectivity in accordance with various embodiments of the disclosure.
Figure 27A:
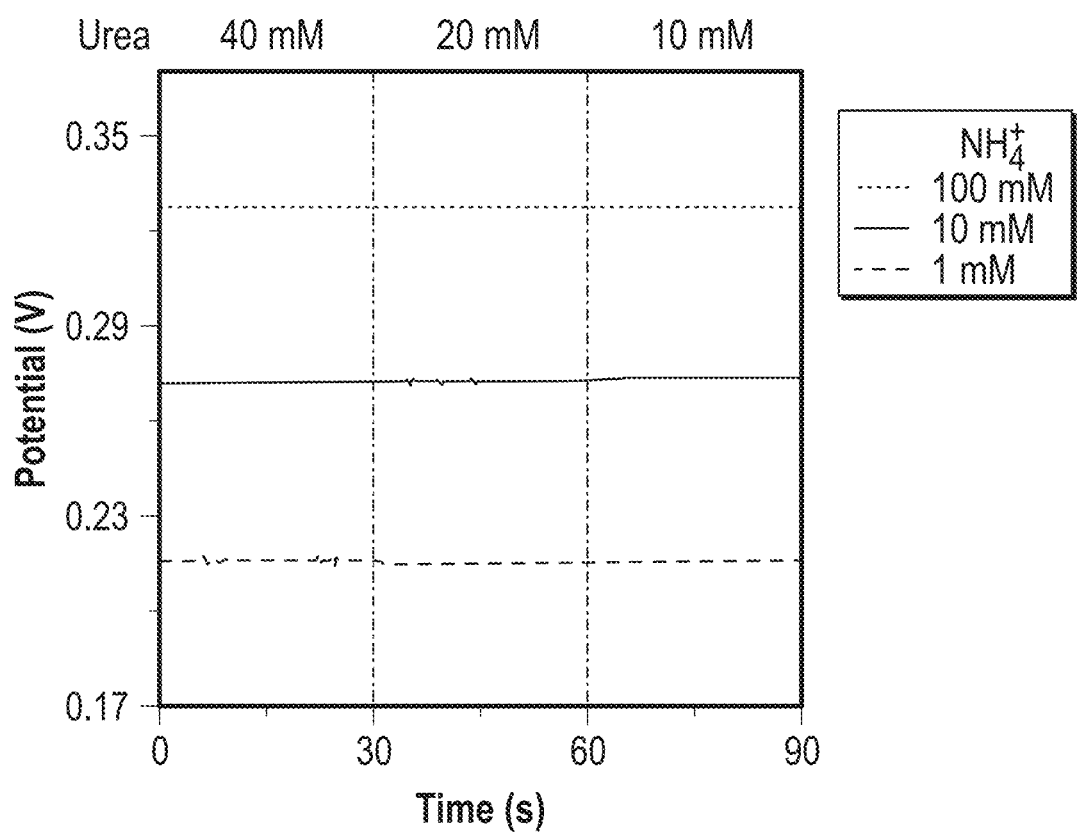
FIG. 27A illustrates, by way of example, sensor selectivity in accordance with various embodiments of the disclosure.
Figure 27B:
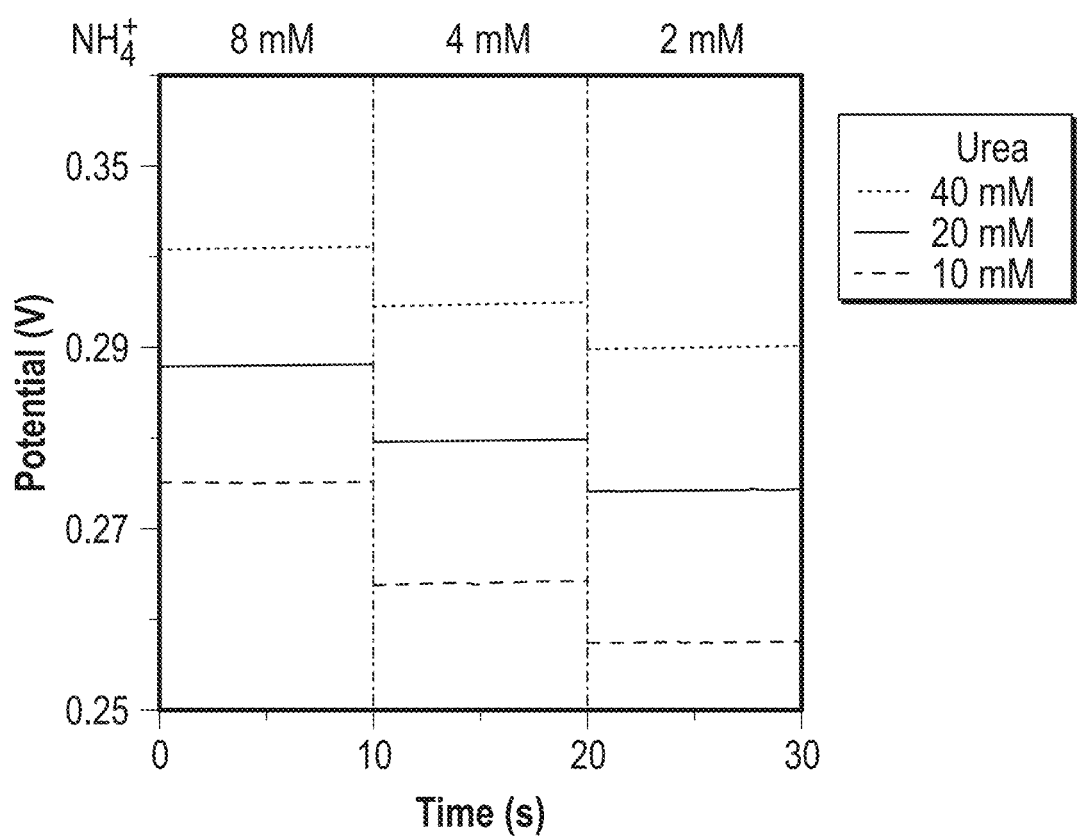
FIG. 27B illustrates, by way of example, sensor selectivity in accordance with various embodiments of the disclosure.

In embodiments, the $NH_4^+$ and urea sensor array may be designed on a soft electrochemical patch based on the $NH_4^+$ ion-selective electrodes (ISE). Compared to the $NH_4^+$ sensor, the urea sensor may contain an additional enzymatic layer where urease converts urea to carbon dioxide and ammonia; the increased $NH_4^+$ product reflects the urea level. A linear relationship between potential output and logarithmic concentrations of the target analytes is obtained, with near-Nerstian sensitivities of 60.3 mV and 60.0 mV per decade of concentration for $NH_4^+$ and urea sensors, respectively. FIGS. 26A and 26B illustrate the selectivity of the various sensor arrays. FIG. 26A, for example, depicts the selectivity of the $NH_4^+$ sensor, while FIG. 26B depicts the selectivity of the urea sensor. The dependence of urea and $NH_4^+$ concentrations on the sensor response is illustrated in FIG. 27A and FIG. 27B. Considering that $NH_4^+$ level has a significant influence on urea sensor reading, it is essential to simultaneously monitor both the urea and $NH_4^+$ with real-time calibration for accurate sweat analysis.

Figure 27C:
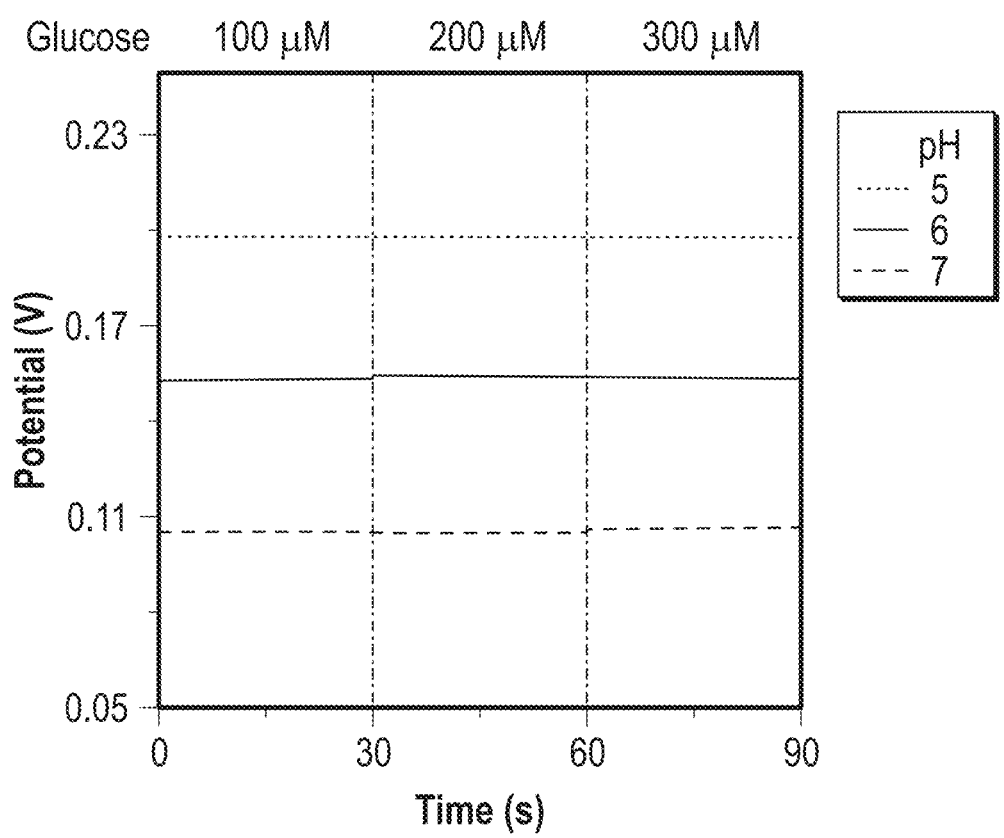
FIG. 27C illustrates, by way of example, sensor selectivity in accordance with various embodiments of the disclosure.
Figure 27D:
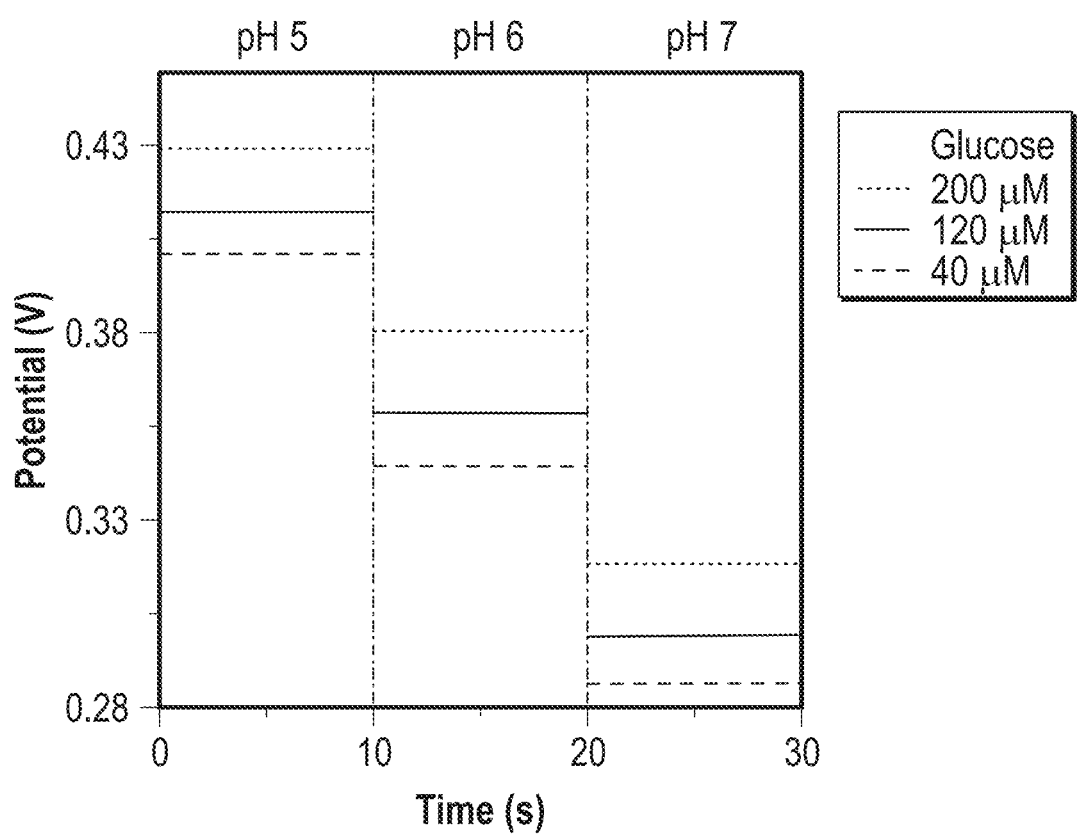
FIG. 27D illustrates, by way of example, sensor selectivity in accordance with various embodiments of the disclosure.

In embodiments, the glucose and pH sensor array may be prepared using a similar potentiometric sensing approach. For example, a sandwich structure—Nafion/chitosan (CS)-glucose oxidase (GOx)/Nafion—may be coated on the platinum deposited electrode to form highly sensitive and selective glucose sensor; an electropolymerized polyaniline film may serve as the hydrogen ion-selective film for pH sensing. FIG. 5 at frames 503 and 504 illustrate the responses of the glucose and pH sensors in 40-200 μM glucose and pH 4-8 solutions, respectively. A linear response between the potential output of glucose sensor and glucose concentrations (in physiologically relevant range 0-150 μM) may be obtained with a sensitivity of 0.1 mV μM-1. A near-Nerstian sensitivity of 55.3 mV per pH may be observed for the pH sensor. Considering that the glucose sensor response is heavily dependent on the solution pH, multiplexed glucose and pH sensing with real-time calibration may also be crucial to obtain high sensing accuracy (e.g., FIG. 27C and FIG. 27D).

Figure 28A:
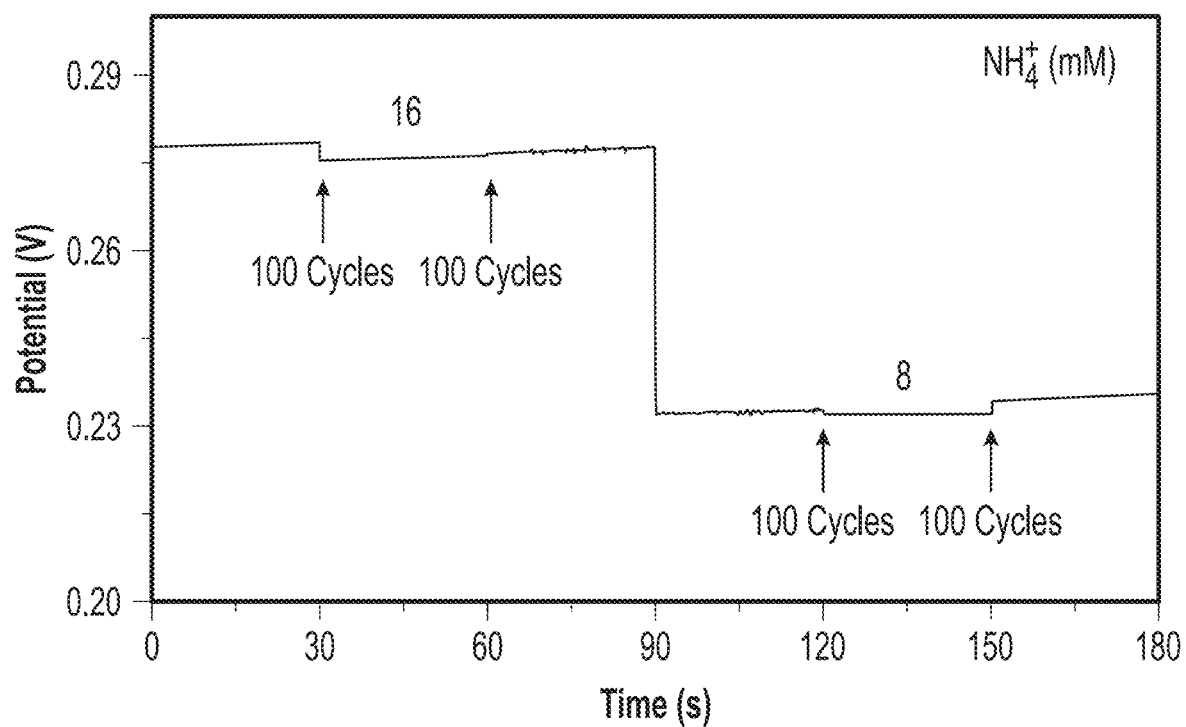
FIG. 28A illustrates, by way of example, sensor stability in accordance with various embodiments of the disclosure.
Figure 28B:
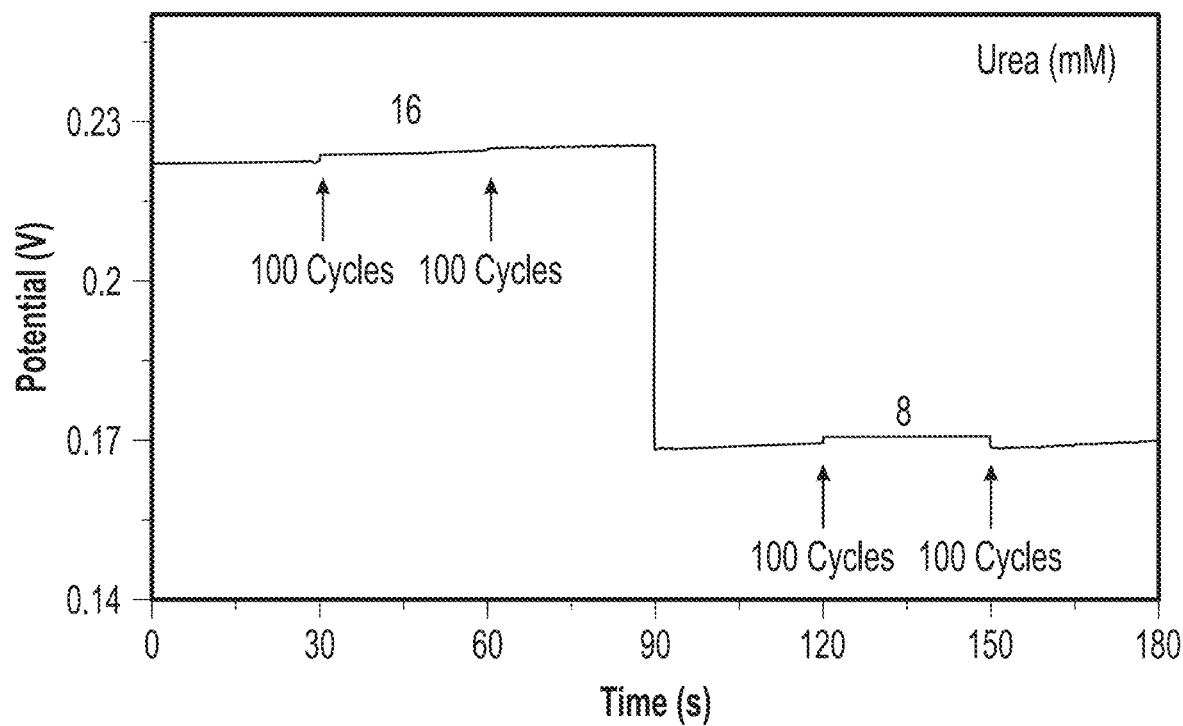
FIG. 28B illustrates, by way of example, sensor selectivity in accordance with various embodiments of the disclosure.
Figure 29A:
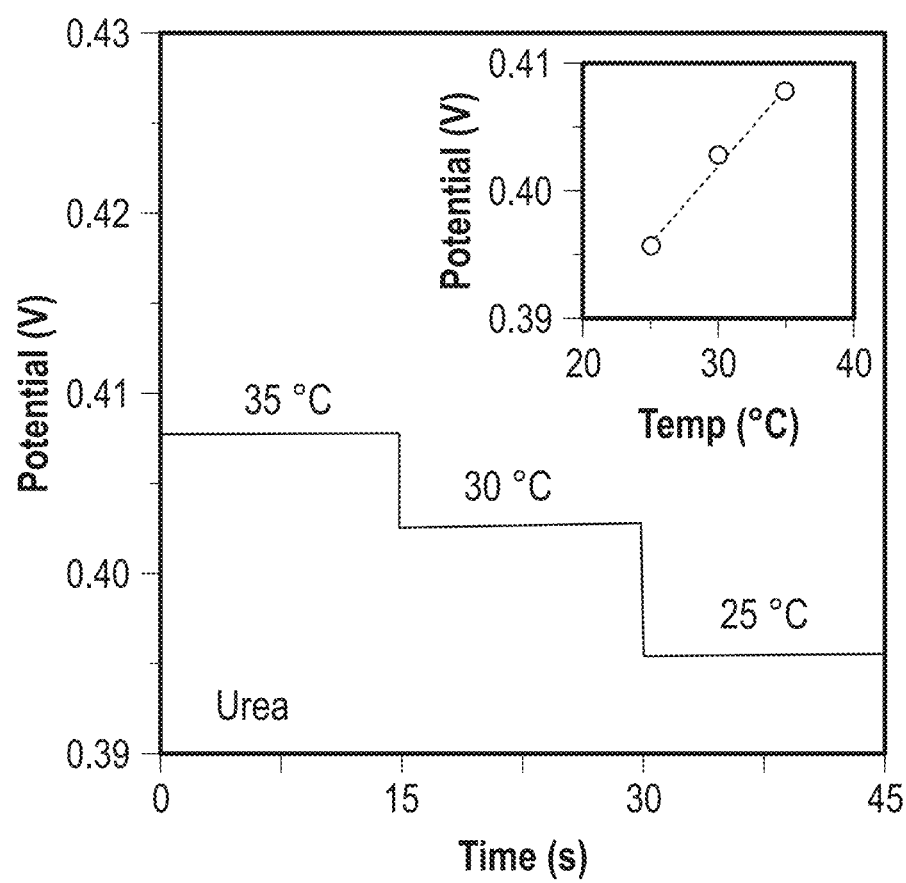
FIG. 29A illustrates, by way of example, sensor selectivity in accordance with various embodiments of the disclosure.
Figure 29B:
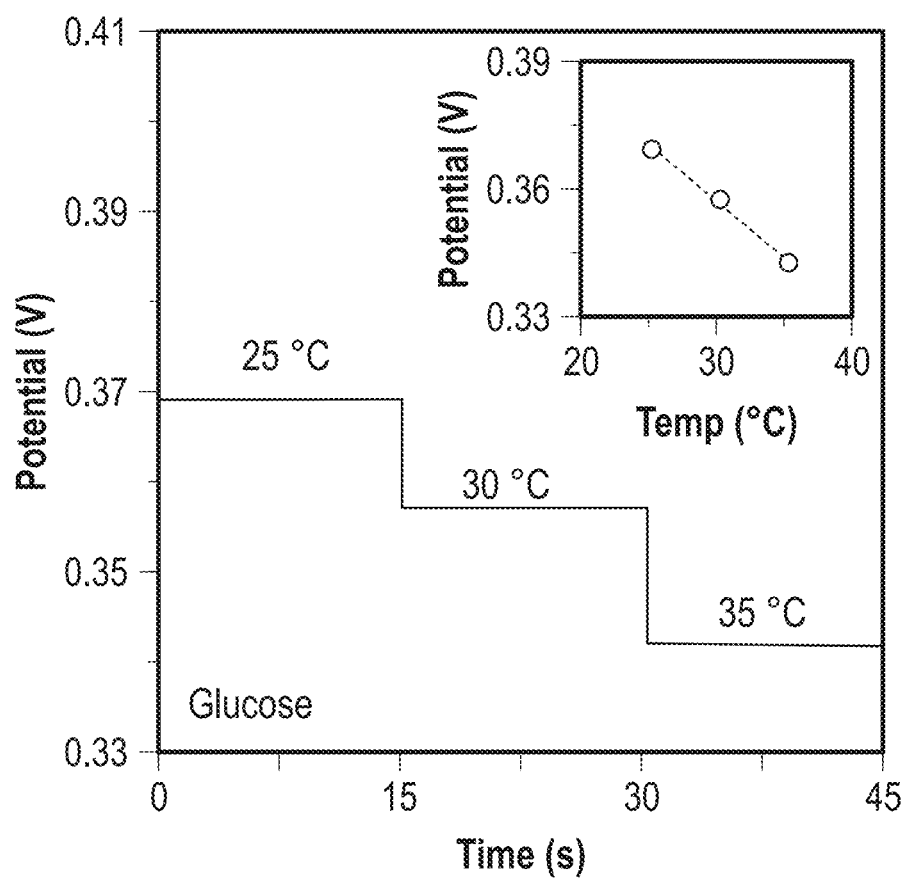
FIG. 29B illustrates, by way of example, sensor stability in accordance with various embodiments of the disclosure.

All sensors show excellent long-term electrochemical and mechanical stabilities during continuous operation, indicating their promise for wearable use (e.g., FIG. 28A and FIG. 28B). Indeed, considering that skin temperature has a direct influence on the enzymatic sensors (glucose and urea sensors as shown in FIG. 29A and FIG. 29B), the on-chip temperature sensor in the BLE module may provide the skin temperature information for real-time calibration.

Figure 30:
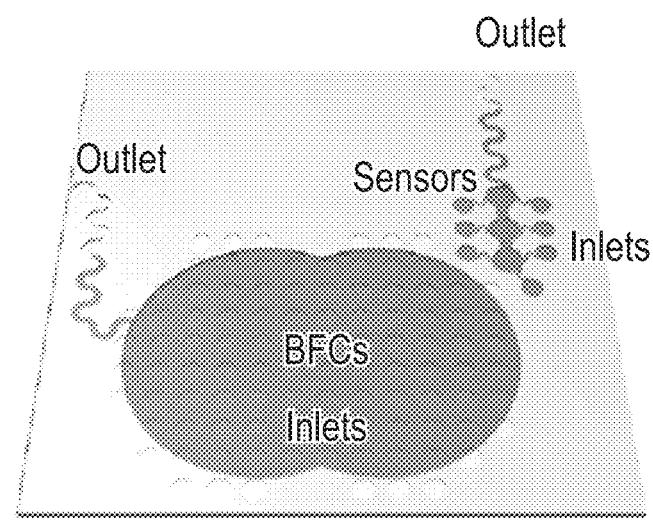
FIG. 30 illustrates, by way of example, various architectures of a multimodal sensing layer that may be used in accordance with embodiments of the disclosure.
Figure 30:
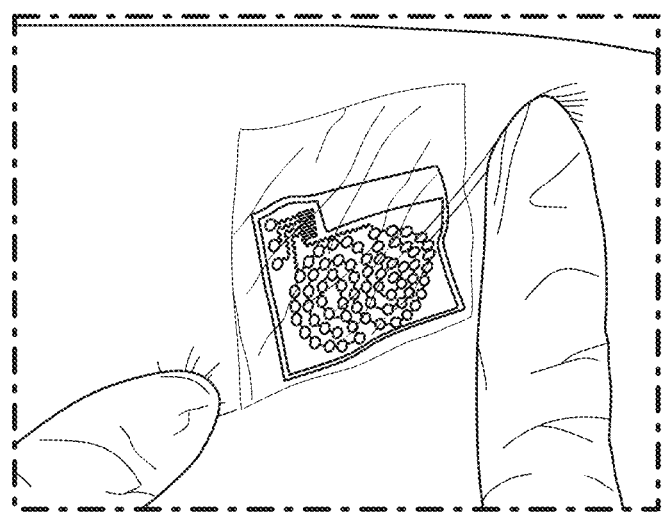

In embodiments, the integration of a microfluidic module may greatly enhance the sweat sampling process and lead to a higher temporal resolution for wearable sensing and more stable power output from the biofuel cells. The laser-patterned microfluidics layer may be assembled in a sandwich structure (M-tape/PDMS/M-tape) and may contain two reservoirs to minimize the influence of the biofuel cell byproducts on the sensing accuracy. FIG. 30 illustrates, for example, a schematic design 3001 for the microfluidics layer of a biosensor, and its application on human skin at photograph 3002. In-vitro flow test shows that when the $NH_4^+$ level in the input solution is switched from 5 to 10 Mm at a physiologically measured sweat rate of 0.05 ml h-1, it takes about 4 minutes for the $NH_4^+$ sensor to reach new stable reading, indicating the small time delay for the on-body continuous monitoring. In embodiments, the biosensor may be mechanically flexible and may conformally laminate on a curved substrate.

Example 9: On-Body System Validation

Figure 31A:
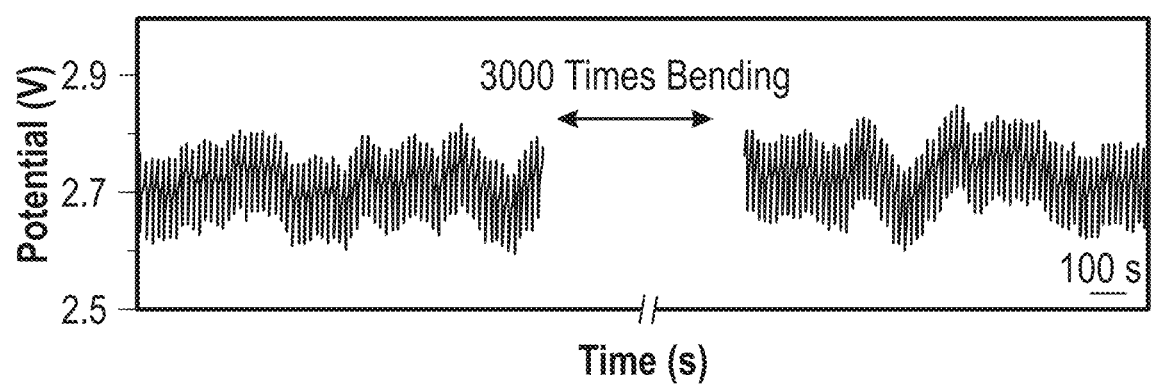
FIG. 31A illustrates, by way of example, validation of an auto-powered biosensor in accordance with various embodiments of the disclosure.
Figure 31B:
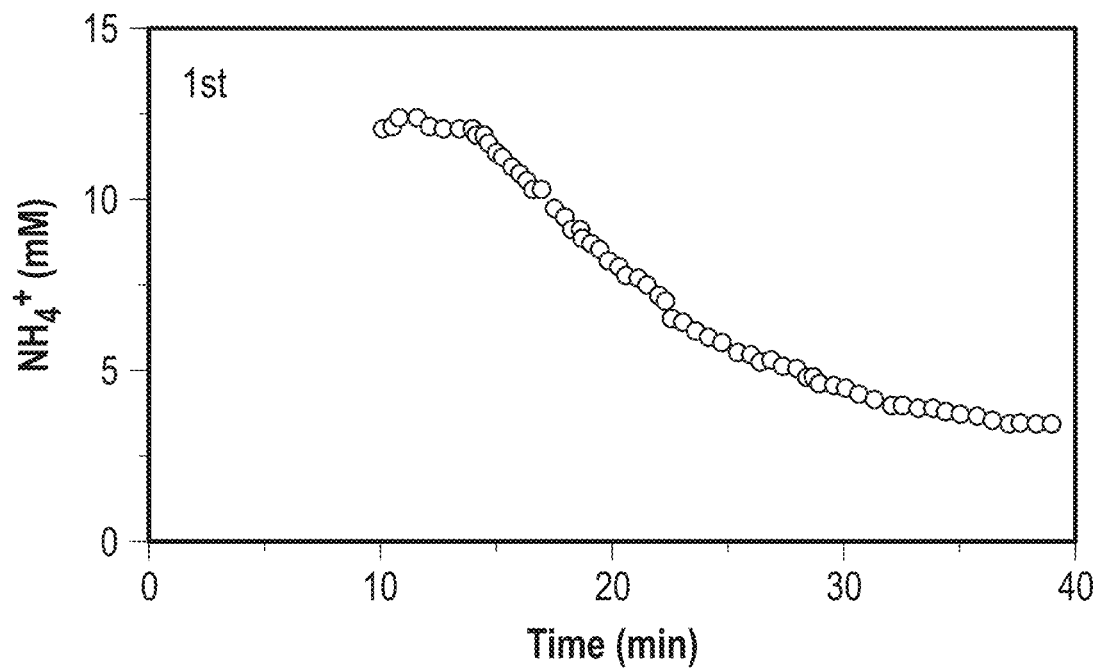
FIG. 31B illustrates, by way of example, validation of an auto-powered biosensor in accordance with various embodiments of the disclosure.
Figure 31C:
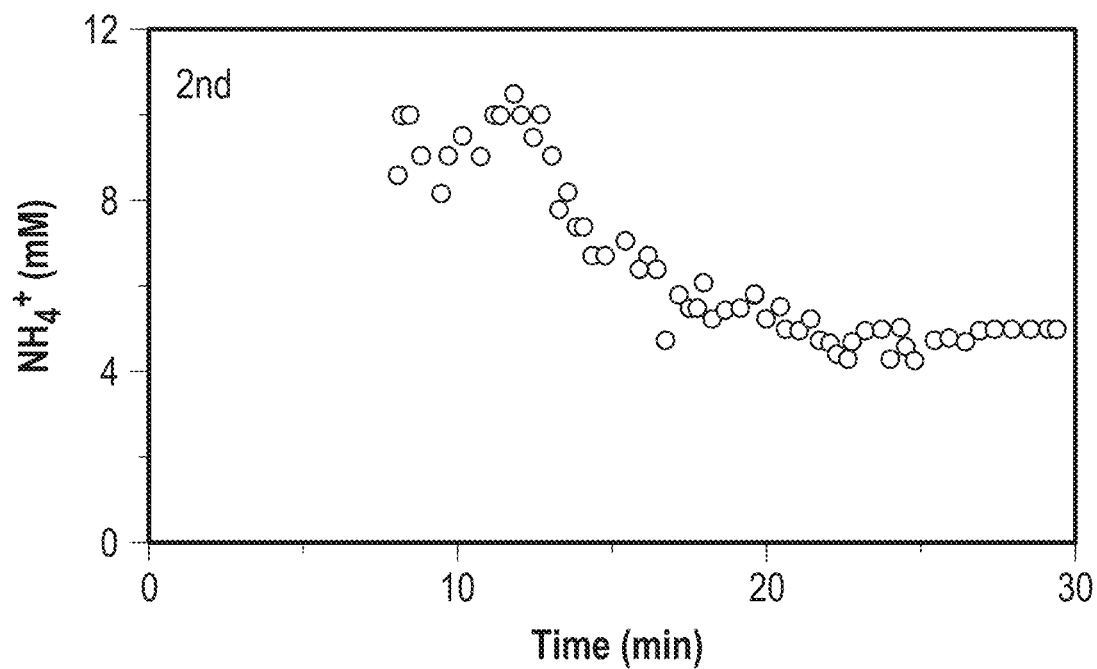
FIG. 31C illustrates, by way of example, validation of an auto-powered biosensor in accordance with various embodiments of the disclosure.

An auto-powered biosensor according to various embodiments disclosed herein may mimic skin in its strength and elasticity, and resistance to heat and moisture. On-body validation of the biosensor was conducted on healthy human subjects toward continuous metabolic monitoring during a constant-load stationary biking exercise. During the biking process, the urea and $NH_4^+$ levels in sweat decrease rapidly and then stabilize over time. A similar trend may be observed for sweat glucose while a stable pH response throughout the exercise is obtained. Indeed, the biosensor shows good reusability, stability, and biocompatibility during long-term usage. For example, FIGS. 31A-31C illustrate the biocompatibility of a biosensor manufactured and used according to various embodiments of the disclosure. FIG. 31A depicts, for example, the charging performance of the biosensor (680 μF capacitor) in 20 mM lactate before and after 3000 times bending cycles (radius of bending curvature: 1.5 cm). FIG. 31B and FIG. 31C depict, for example, repeated use (e.g., $1^{st}$ and $2^{nd}$) of a biosensor for sweat $NH_4^+$ level analysis on a subject's forehead during the same day. As depicted, the biosensor was peeled off the user's skin after the first cycling test (e.g., FIG. 31B) and then 4 hours later, was reapplied and used for the second cycling test (e.g., FIG. 31C).

In addition to on-body validation, the use of the biosensor in metabolic and nutritional management was evaluated through controlled dietary challenges. As compared to the initial levels, sweat urea and $NH_4^+$ levels measured 2-hour after a standardized protein intake increase significantly in all three subjects. In contrast, decreased trends are obtained during the 2-hour period from all the subjects without protein intake. In oral glucose tolerance test (OGTT), sweat glucose levels increased dramatically for all subjects after the glucose intake and decreased after 2 hours for subjects without intake. These data indicate the biosensor may have potential in auto-powered personalized physiological and metabolic monitoring.

Figure 32:
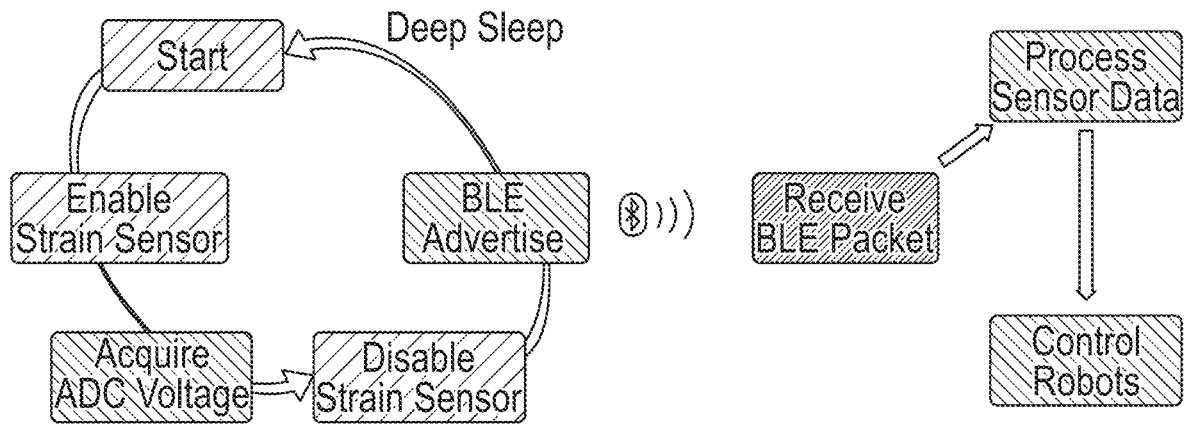
FIG. 32 illustrates, by way of example, various circuitry architectures that may be used in accordance with embodiments of the disclosure.
Figure 33:
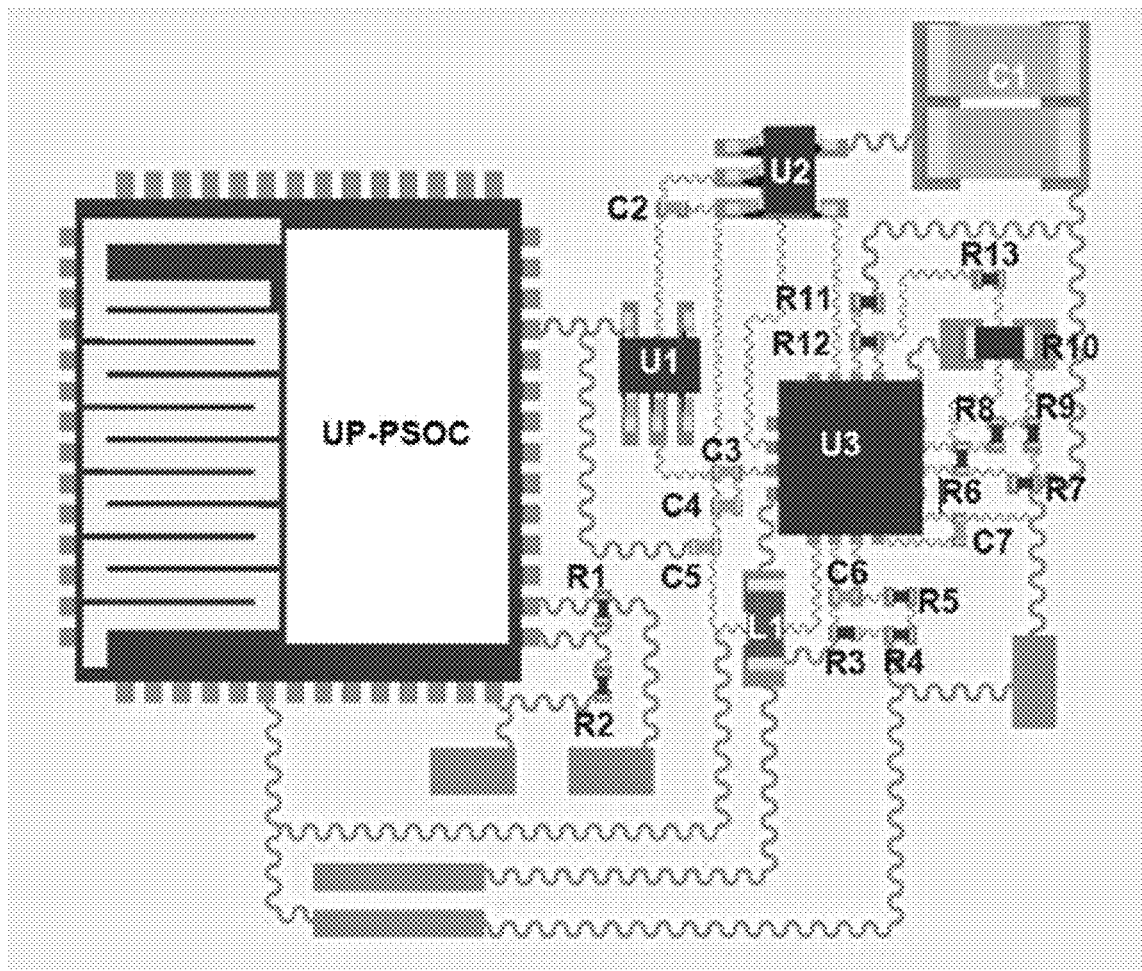
FIG. 33 illustrates, by way of example, various circuitry architectures that may be used in accordance with embodiments of the disclosure.
Figure 34A:
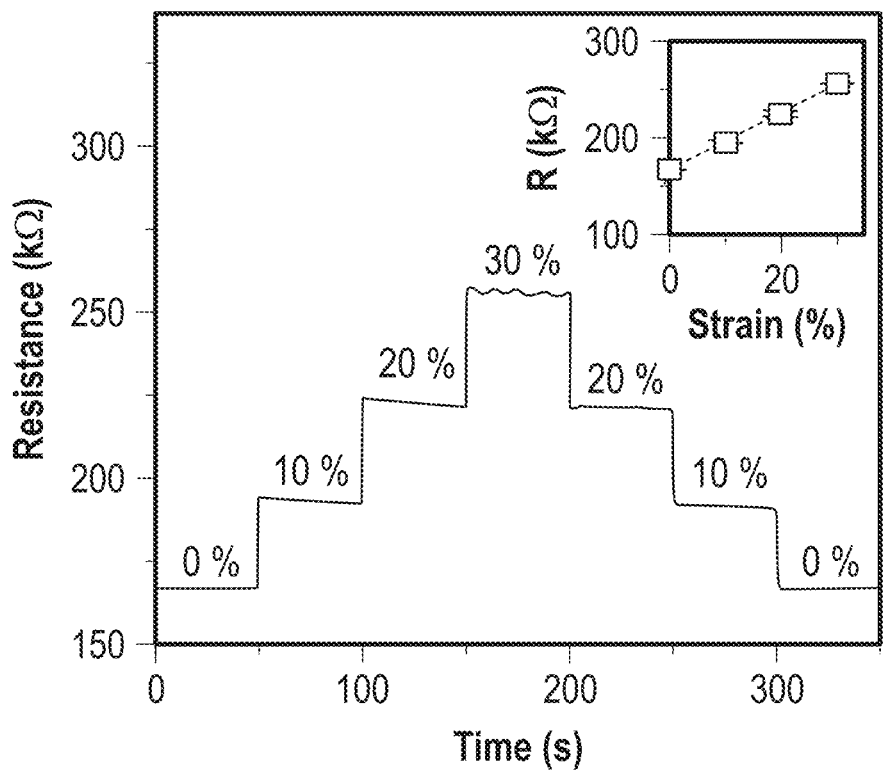
FIG. 34A illustrates, by way of example, validation of a multimodal sensing layer that may be used in accordance with various embodiments of the disclosure.
Figure 34B:
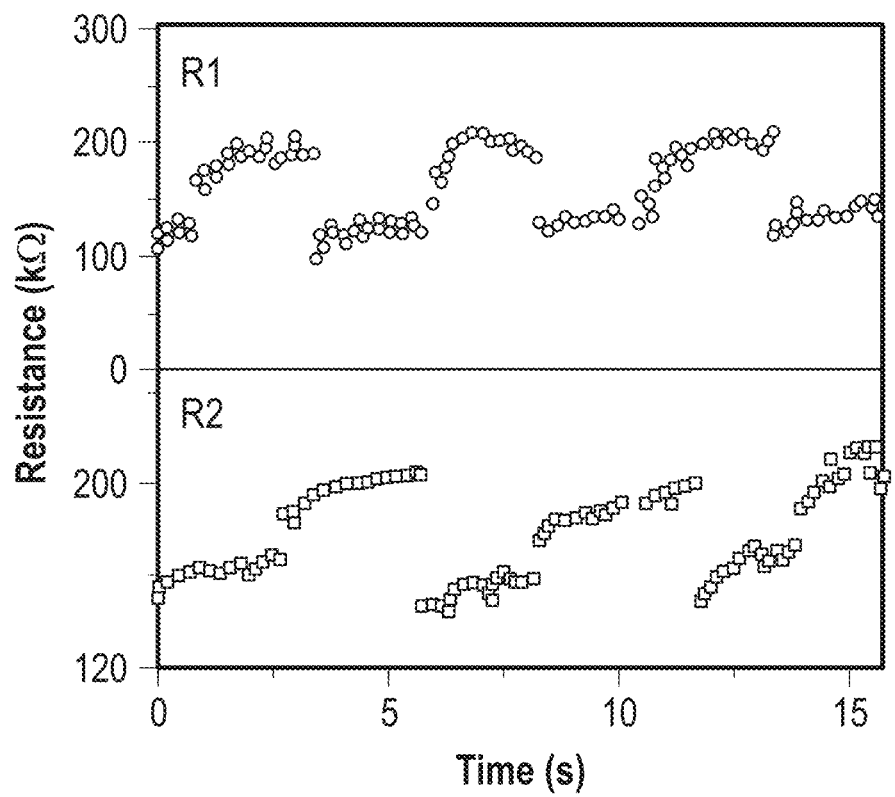
FIG. 34B illustrates, by way of example, validation of a multimodal sensing layer that may be used in accordance with various embodiments of the disclosure.

Example 10: Evaluation of Biosensor as a Human-Machine Interface for Robotic Assistance In embodiments, when integrated with soft strain sensors, the systems and methods disclosed herein may function as a human-machine interface toward robotic applications (e.g., FIGS. 32 and 33). For illustrative purposes, a key for the components of FIG. 33 is provided in Table 4. In embodiments, a strain sensor may be designed based on CNTs/PDMS elastomer, wherein the resistance of the sensors increases linearly with applied strain (e.g., FIG. 34A). In embodiments, two strain sensors may be placed on the hand and the elbow, respectively, and connected to the biosensor. In embodiments, the bending of the finger and elbow may be monitored from the resistance change of the strain sensors (e.g., FIG. 34B). In embodiments, each resistive type strain sensor as part of a voltage divider consumes a total of about 5 μA. In embodiments, the biosensor may also be used for robotic assistance in the rehabilitation settings. Indeed, by incorporating more physical sensors for electroencephalogram (EEG) and electromyography (EMG) recording along with the continuous metabolic monitoring, the multimodal biosensor could facilitate the design and optimization of novel prostheses that bring the human in the loop of prosthesis control to enable real-time user-specific responses to human intent and behavior.

TABLE 4

| Components | Description | Value and Series No. |
| --- | --- | --- |
| UP-PSOC | EZ-BLE Creator Module | CYBLE-214009-00 |
| U1 | Voltage Regulators | TPS71721 |
| U2 | Analogue Switch | MAX4715EXK + T |
| U3 | Boost Converter | BQ25504 |
| L1 | Fixed Inductors | MLZ1608 |
| C1 | 0402 Capacitor | 220 μF*2 |
| C2 | 0202 Capacitor | 0.1 μF |
| C3 | 0202 Capacitor | 4.7 μF |
| C4 | 0202 Capacitor | 0.1 μF |
| C5 | 0202 Capacitor | 0.1 μF |
| C6 | 0202 Capacitor | 4.7 μF |
| C7 | 0202 Capacitor | 0.1 μF |
| R1 | 0202 Resistor | 200 kΩ |

TABLE 4-continued

| Components | Description | Value and Series No. |
|---|---|---|
| R2 | 0202 Resistor | 200 kΩ |
| R3 | 0202 Resistor | 10 kΩ |
| R4 | 0202 Resistor | 4.99 kΩ |
| R5 | 0202 Resistor | 4.99 kΩ |
| R6 | 0202 Resistor | 4.32 kΩ |
| R7 | 0202 Resistor | 5.6 kΩ |
| R8 | 0202 Resistor | 3.6 kΩ |
| R9 | 0202 Resistor | 6.2 kΩ |
| R10 | 0202 Resistor | 0 kΩ |
| R11 | 0202 Resistor | 4.03 kΩ |
| R12 | 0202 Resistor | 3 kΩ |
| R13 | 0202 Resistor | 3 kΩ |

It is understood that the present invention is not limited to the specific details of these examples. While a preferred embodiment of the invention has been shown and described in considerable detail, it should be understood that many changes can be made in the structure without departing from the spirit or scope of the invention. Accordingly, it is not desired that the invention should be limited to the exact structure shown and described in the examples provided.

What is claimed is:

1. A biosensor capable of self-power, the biosensor comprising:
   a microfluidics layer;
   a multimodal sensing layer comprising an electrode and a biofuel cell; and
   a logic circuit comprising a processor and a non-transitory memory with computer executable instructions embedded thereon;
   wherein the microfluidics layer comprises multiple microchannels transversely oriented to obtain a biological sample, the biological sample comprising a target molecule and an energy molecule;
   the multimodal sensing layer is fluidically coupled to the microfluidics layer to receive the biological sample from the microchannels;
   the electrode configured to detect a measurement of an electrical property corresponding to a target molecule present in the biological sample;
   the biofuel cell comprises a lactate oxidase immobilized anode and a Pt-alloy cathode and is configured to harvest energy from the energy molecule present in the biological sample to power the biosensor;
   wherein the lactate oxidase immobilized anode comprises hierarchical Ni microstructures (h-Ni), reduced graphene oxide (rGO) films, and bimediator modified carbon nanotubes (CNTs); and
   the logic circuit is electrically coupled to the electrode and the computer executable instructions cause the processor to identify the electrical property detected with the electrode when the target molecule is present in the biological sample.

2. The biosensor of claim 1, wherein the biological sample comprises one or more of sweat, tears, blood, urine, and saliva.

3. The biosensor of claim 2, wherein the biological sample comprises sweat.

4. The biosensor of claim 1, wherein the electrical property is an electrical current.

5. The biosensor of claim 1, wherein the electrical property is an electrical voltage.

6. The biosensor of claim 1, wherein the electrical property is an electrical impedance.

7. The biosensor of claim 1, wherein the computer executable instructions cause the processor to generate an indication identifying the presence of the target molecule based on the electrical property detected with the electrode.

8. The biosensor of claim 7, wherein the computer executable instructions further cause the processor to wirelessly transmit to the user the indication identifying the presence of the target molecule.

9. The biosensor of claim 8, wherein wireless transmission of the indication to the user identifying the presence of the target molecule comprises Bluetooth® communication.

10. The biosensor of claim 1, further comprising a moisture resistant layer.

11. A method for powering a biosensor comprised of a microfluidics layer comprising multiple microchannels transversely oriented to obtain a biological sample, a multimodal sensing layer fluidically coupled to the microfluidics layer and comprising an electrode and a biofuel cell, and a logic circuit, the method comprising:
   receiving, a biological sample comprising an energy molecule, such that the biological sample can be channeled through the microfluidics layer to the multimodal sensing layer; and
   harvesting, with the biofuel cell, energy from an energy molecule present in the biological sample;
      wherein the biofuel cell comprises a lactate oxidase immobilized anode and a Pt-alloy cathode and is configured to harvest energy from the energy molecule present in the biological sample to power the biosensor;
   wherein the lactate oxidase immobilized anode comprises hierarchical Ni microstructures (h-Ni), reduced graphene oxide (rGO) films, and bimediator modified carbon nanotubes (CNTs).

12. The method of claim 11, wherein harvesting energy with the biofuel cell comprises catalyzing lactate to pyruvate.

13. The method of claim 11, wherein harvesting energy with the biofuel cell comprises reducing oxygen to water.

14. The method of claim 11, wherein the biological sample comprises one or more of sweat, tears, blood, urine, and saliva.

15. The method of claim 11, wherein the target molecule is lactate.

16. The method of claim 12, wherein harvesting energy with the biofuel cell comprises catalyzing lactate to pyruvate.

17. The method of claim 16, wherein harvesting energy with the biofuel cell comprises reducing oxygen to water.

18. The method of claim 16, wherein the biological sample comprises one or more of sweat, tears, blood, urine, and saliva.

19. The method of claim 16, wherein the biological sample comprises sweat.

* * * * *